(12) United States Patent
Li et al.

(10) Patent No.: US 12,268,682 B2
(45) Date of Patent: Apr. 8, 2025

(54) ANTICANCER DRUG FL118 FORMULATION FOR TREATMENT OF HUMAN CANCER

(71) Applicant: CANGET BIOTEKPHARMA, LLC, Buffalo, NY (US)

(72) Inventors: Fengzhi Li, Buffalo, NY (US); Xiang Ling, Buffalo, NY (US); Jianqun Liao, Buffalo, NY (US)

(73) Assignee: Canget Bio Tekpharma, LLC, Buffalo, NY (US)

( * ) Notice: Subject to any disclaimer, the term of this patent is extended or adjusted under 35 U.S.C. 154(b) by 628 days.

(21) Appl. No.: 17/629,537

(22) PCT Filed: Jul. 22, 2020

(86) PCT No.: PCT/US2020/043153
§ 371 (c)(1),
(2) Date: Jan. 24, 2022

(87) PCT Pub. No.: WO2021/016401
PCT Pub. Date: Jan. 28, 2021

(65) Prior Publication Data
US 2022/0249464 A1    Aug. 11, 2022

Related U.S. Application Data

(60) Provisional application No. 62/876,835, filed on Jul. 22, 2019.

(51) Int. Cl.
| | | |
|---|---|---|
| A61K 31/4745 | (2006.01) |
| A61K 9/00 | (2006.01) |
| A61K 9/20 | (2006.01) |
| A61K 9/48 | (2006.01) |
| A61K 39/00 | (2006.01) |
| A61K 40/11 | (2025.01) |
| A61K 40/31 | (2025.01) |
| A61K 40/42 | (2025.01) |
| A61K 45/06 | (2006.01) |
| A61K 47/40 | (2006.01) |
| A61P 35/00 | (2006.01) |
| A61P 37/00 | (2006.01) |

(52) U.S. Cl.
CPC ........ *A61K 31/4745* (2013.01); *A61K 9/0053* (2013.01); *A61K 9/2018* (2013.01); *A61K 9/4858* (2013.01); *A61K 40/11* (2025.01); *A61K 40/31* (2025.01); *A61K 40/4202* (2025.01); *A61K 40/4215* (2025.01); *A61K 40/4222* (2025.01); *A61K 45/06* (2013.01); *A61K 47/40* (2013.01); *A61P 35/00* (2018.01); *A61P 37/00* (2018.01)

(58) Field of Classification Search
None
See application file for complete search history.

(56) References Cited

U.S. PATENT DOCUMENTS

| | | |
|---|---|---|
| 2006/0257475 A1 | 11/2006 | Economou et al. |
| 2016/0008397 A1 | 1/2016 | Krams et al. |
| 2018/0170944 A1 | 6/2018 | Li |

FOREIGN PATENT DOCUMENTS

| | | | |
|---|---|---|---|
| WO | WO-2012058666 A2 * | 5/2012 | ........ A61K 31/475 |
| WO | WO-2015148415 A2 * | 10/2015 | ........ A61K 31/4745 |

OTHER PUBLICATIONS

International Search Report and Written Opinion corresponding to International Patent Application No. PCT/US2020/043153, mailed Oct. 19, 2020.
Holthof et la., "Preclinical evidence for an effective therapeutic activity of FL118, a novel survivin inhibitor, in patients with relapsed/refractory multiple myeloma." Haematologica, vol. 105, No. 2, Feb. 2020.

* cited by examiner

*Primary Examiner* — Noble E Jarrell
(74) *Attorney, Agent, or Firm* — McAndrews, Held & Malloy, Ltd.

(57) ABSTRACT

Described herein, are the extended and newly discovered novel formulations of FL118 for cancer treatment to preclude, eliminate or reverse cancer phenotypes and treatment resistance.

15 Claims, 44 Drawing Sheets

CANGET_P0003: Figure 1

CANGET_P0003: Figure 2

CANGET_P0003: Figure 4

CANGET_P0003: Figure 5

CANGET_P0003: Figure 7

CANGET_P0003: Figure 8

CANGET_P0003:

CANGET_P0003: Figure 10

CANGET_P0003:

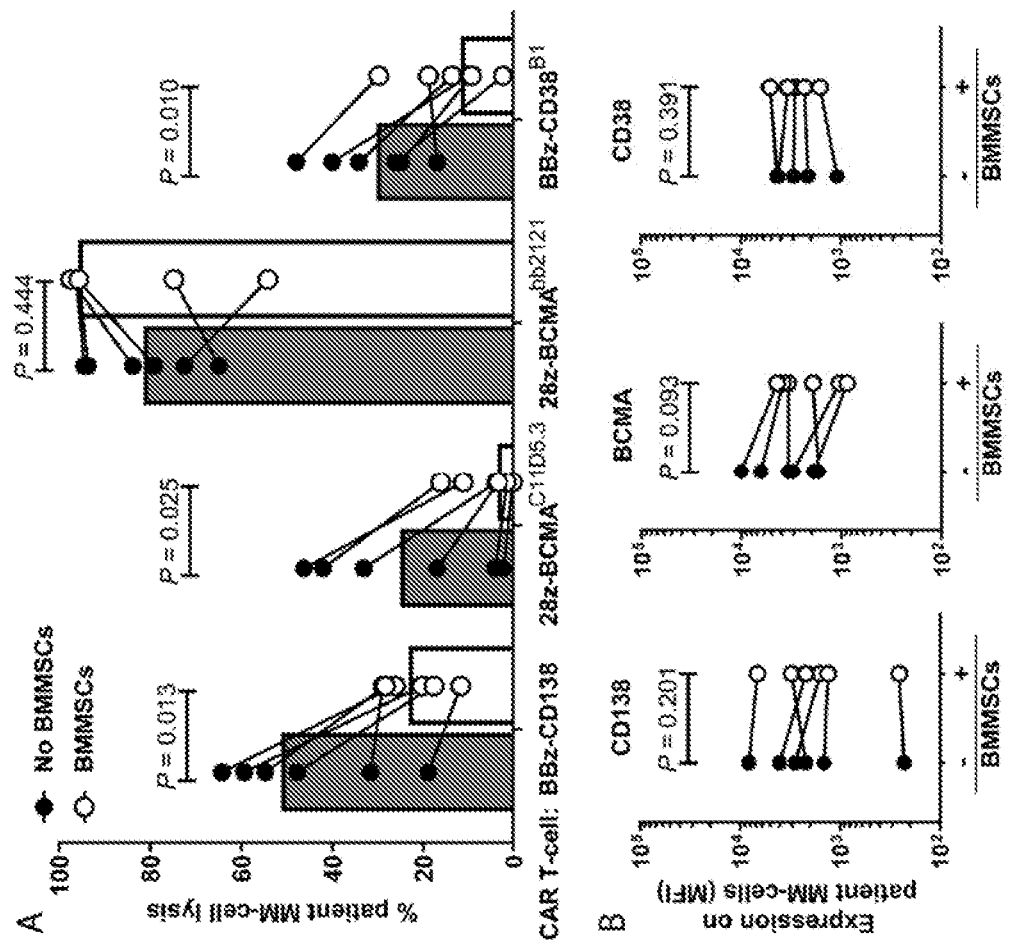
CANGET_P0003: Figure 12

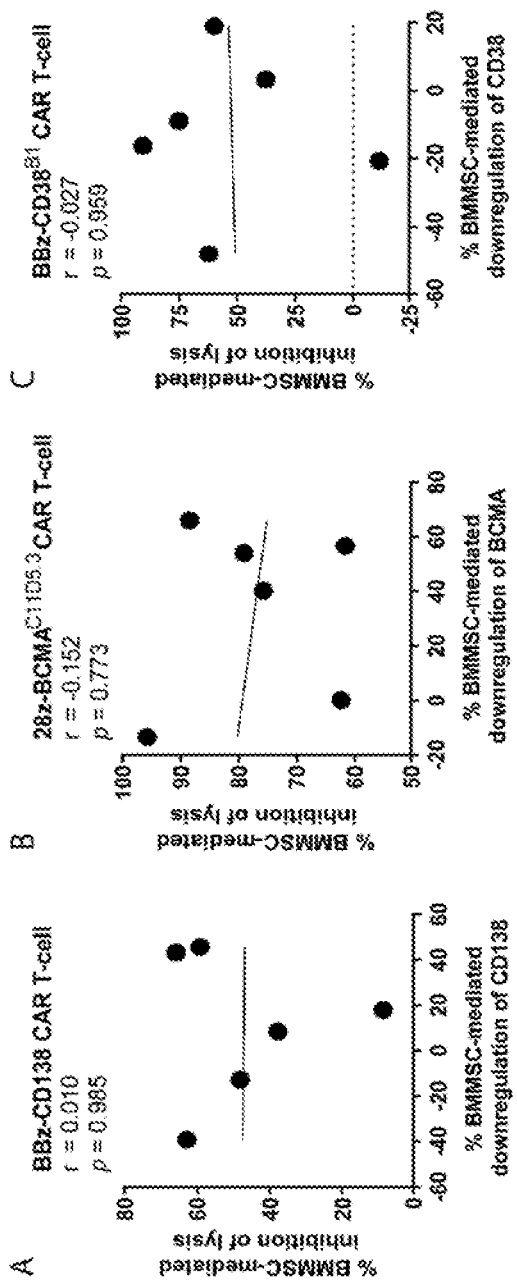
CANGET_P0003: Figure 13

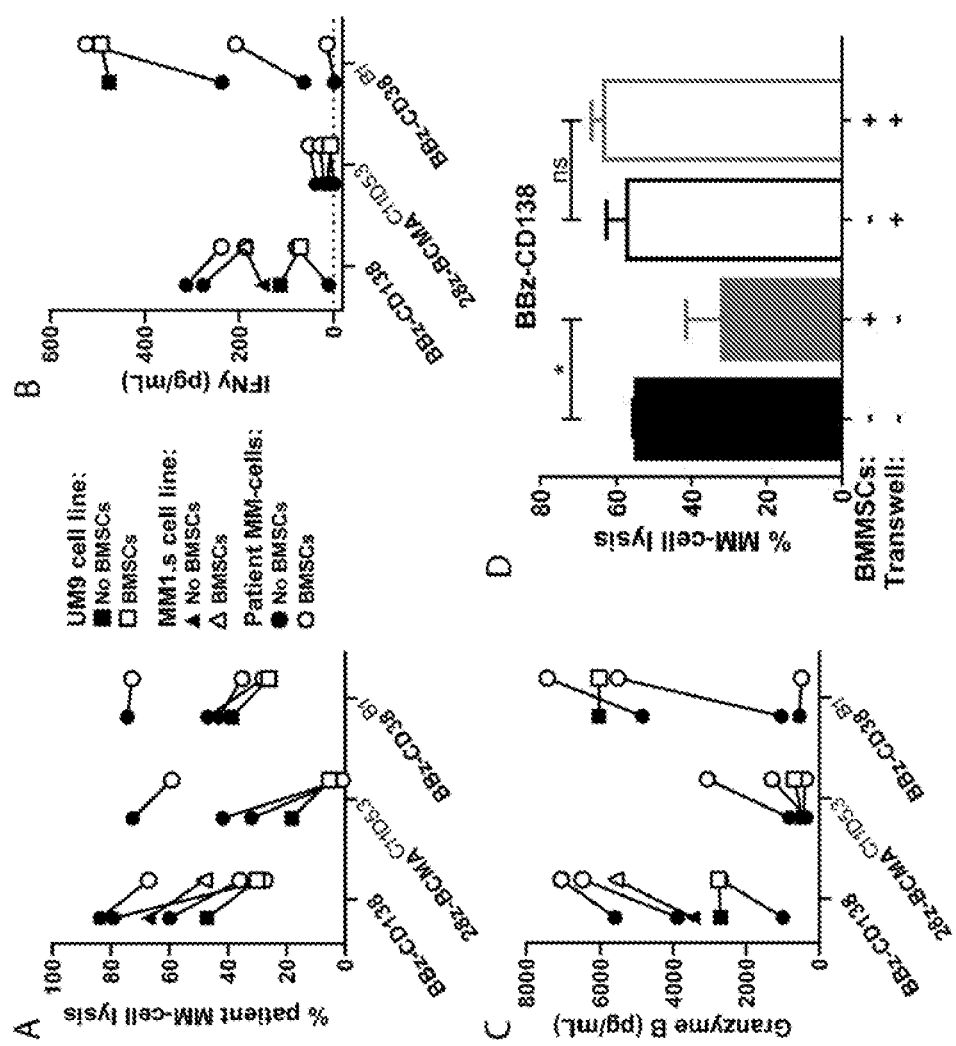
CANGET_P0003: Figure 14

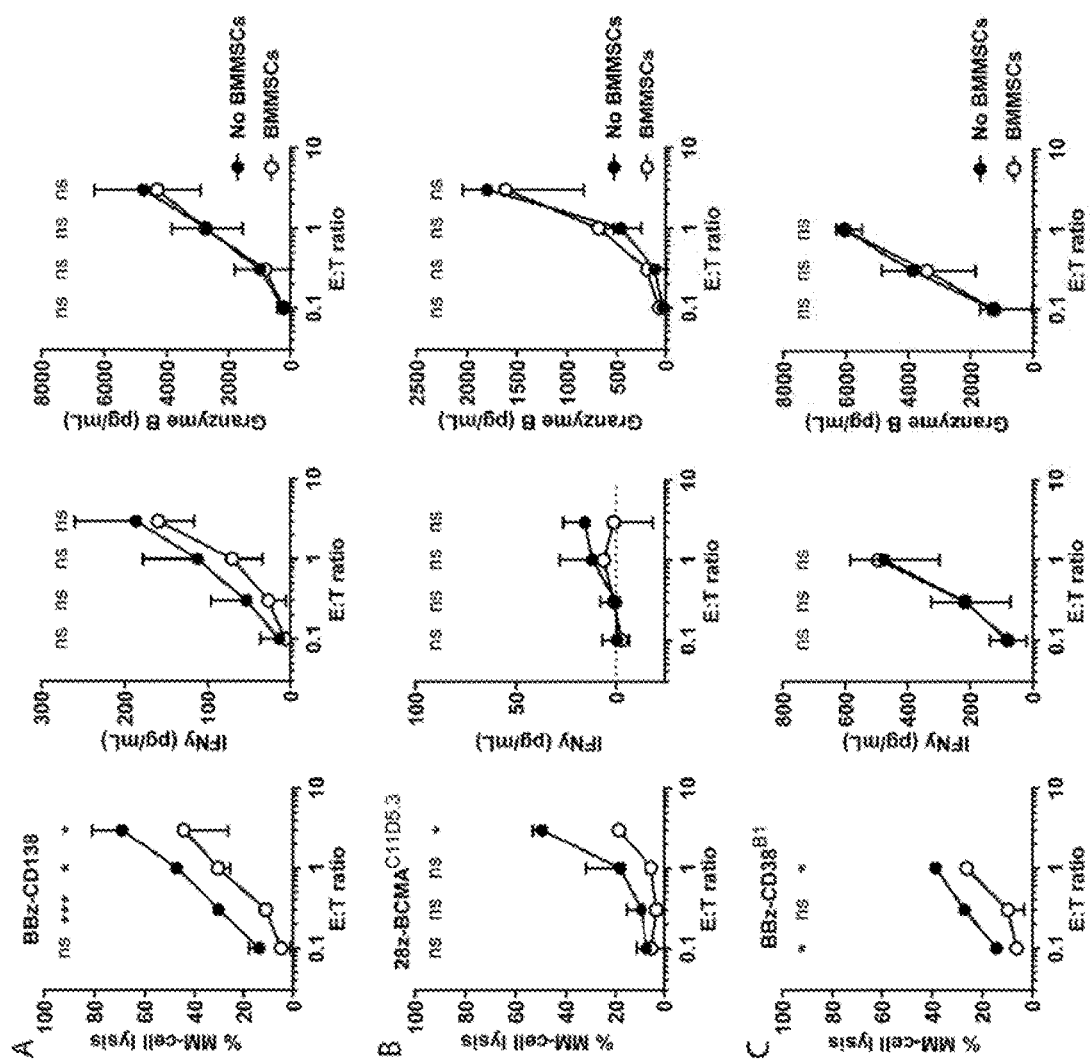
CANGET_P0003: Figure 15

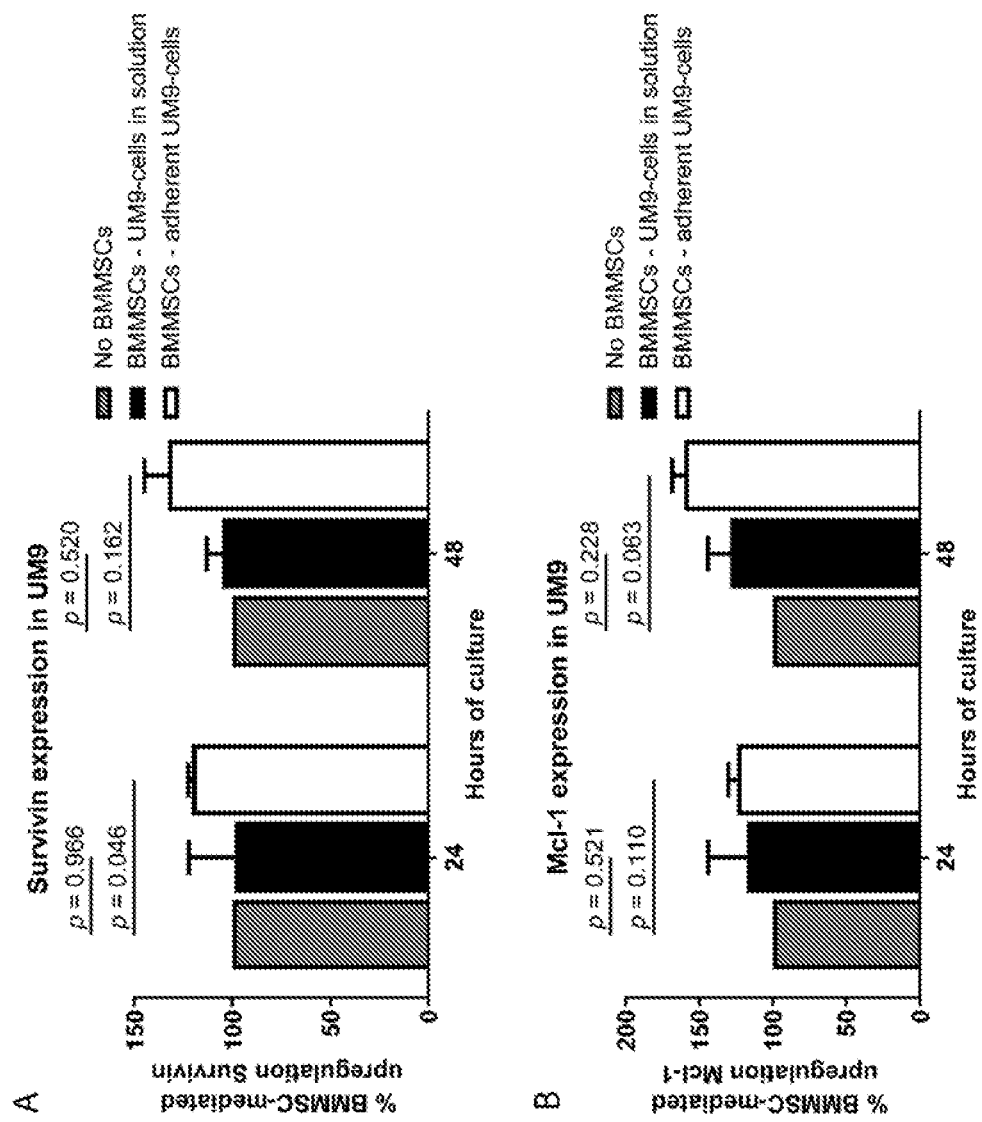
CANGET_P0003: Figure 16

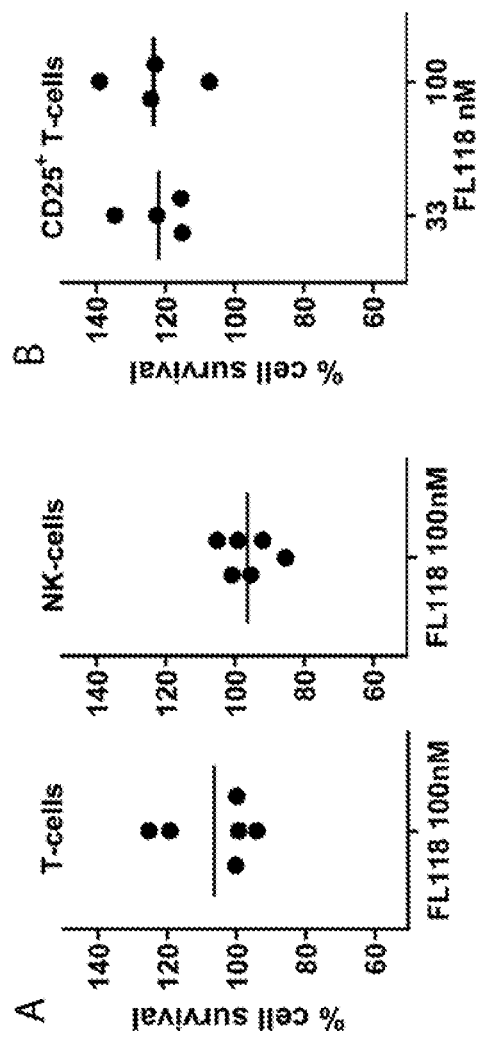
CANGET_P0003: Figure 17

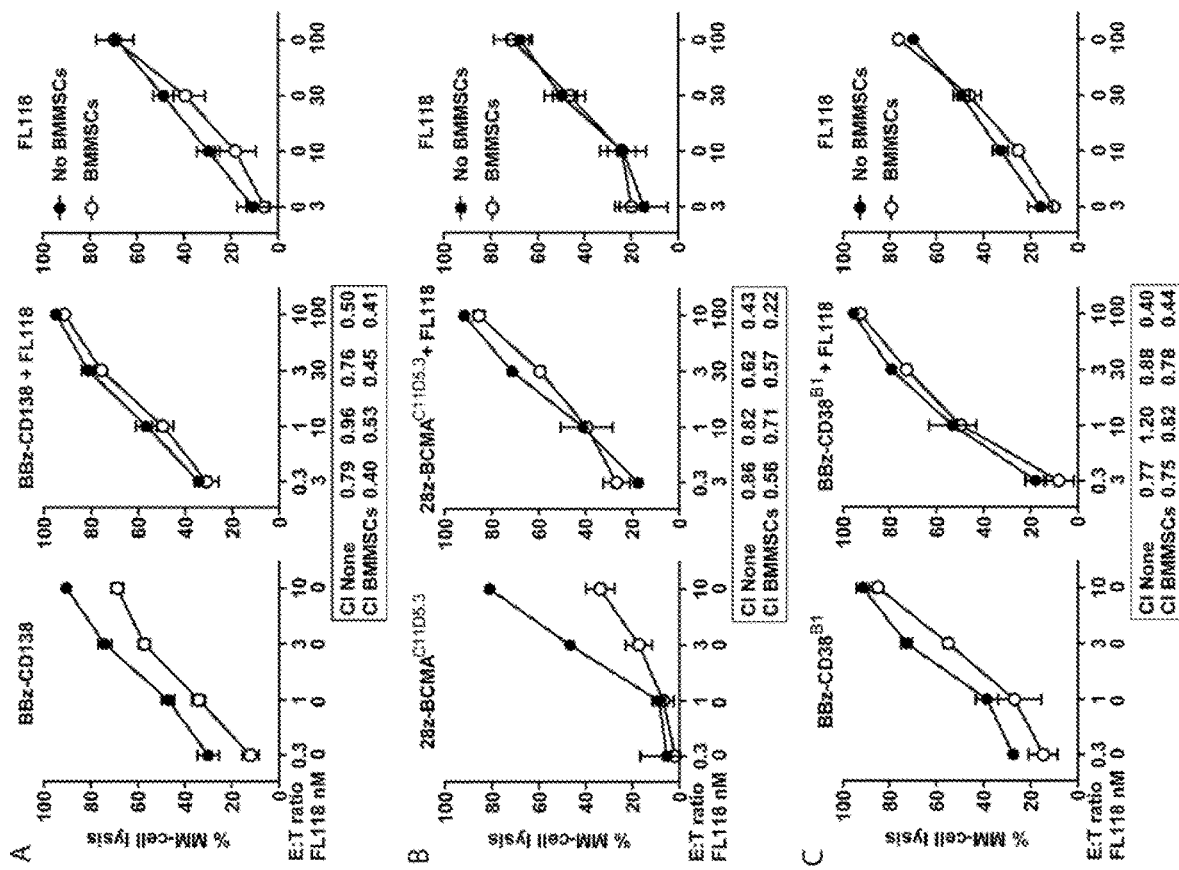
CANGET_P0003: Figure 18

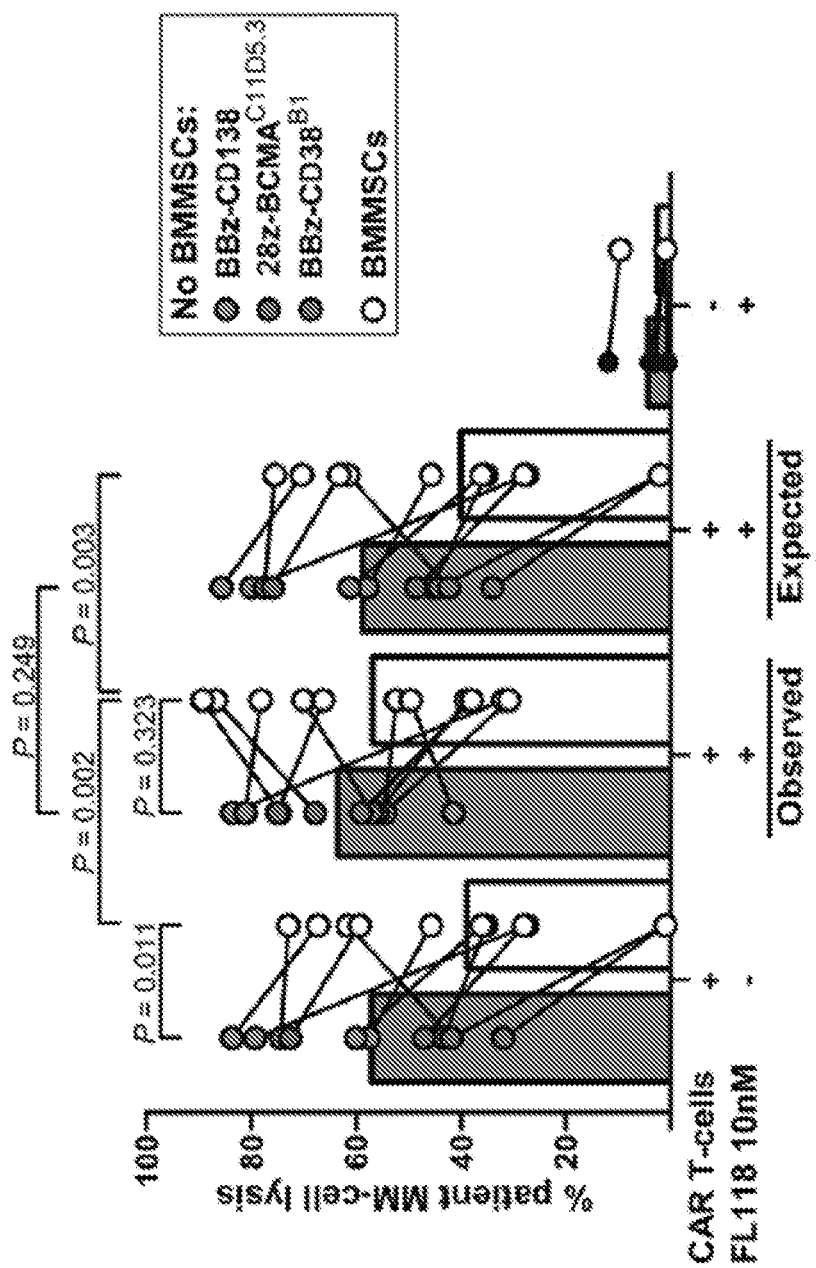

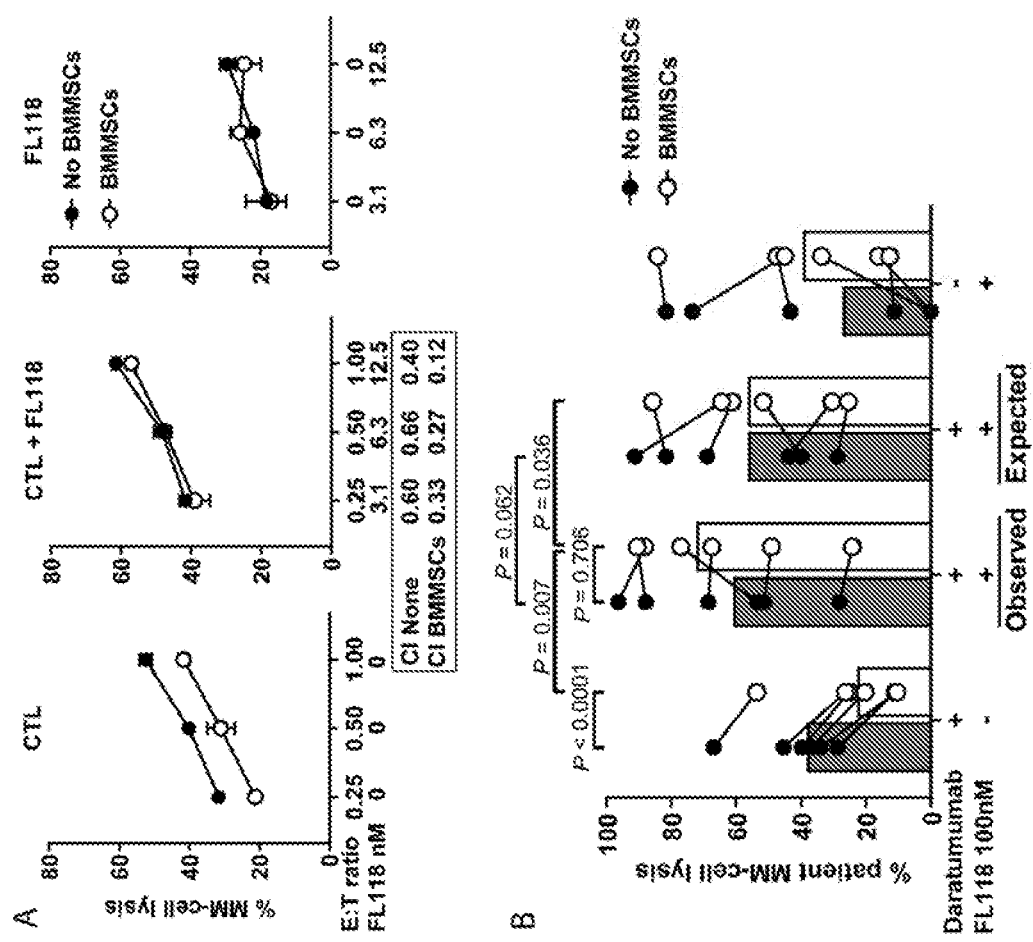
CANGET_P0003: Figure 20

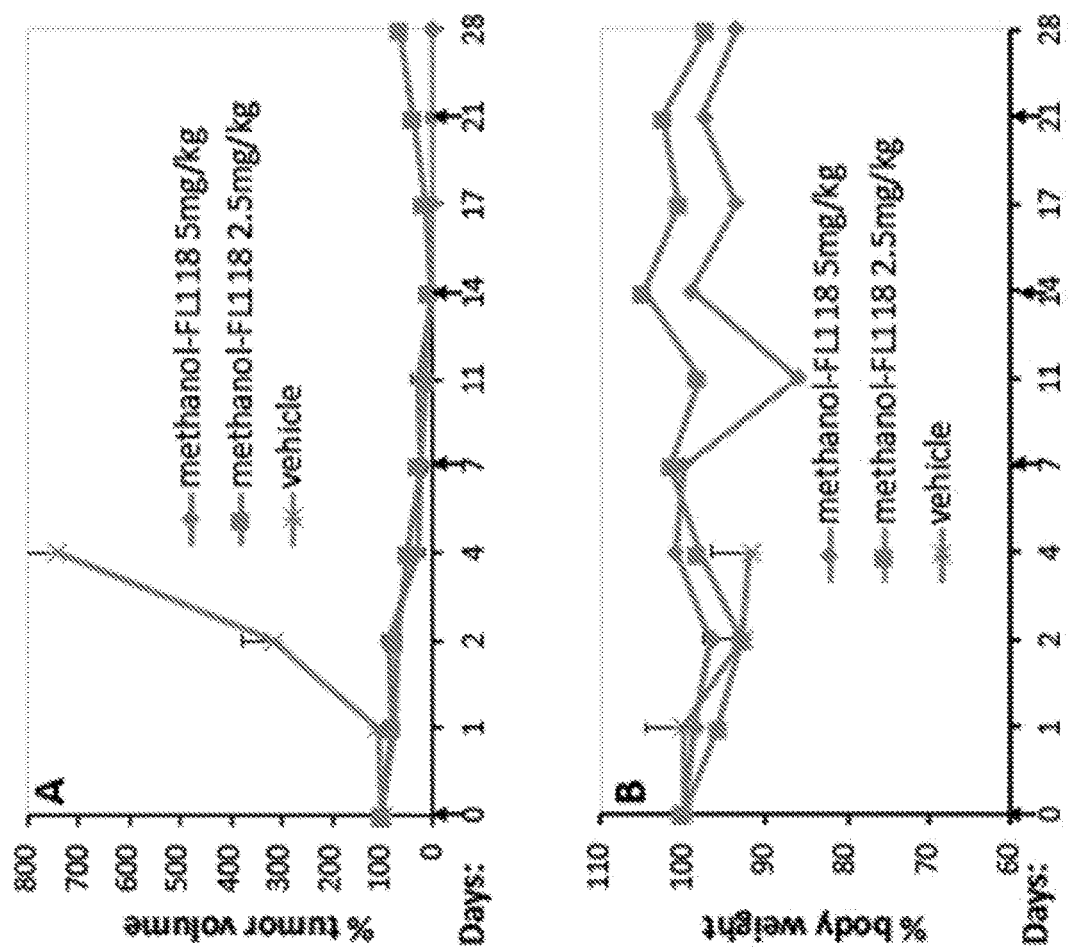
CANGET_P0003: Figure 21

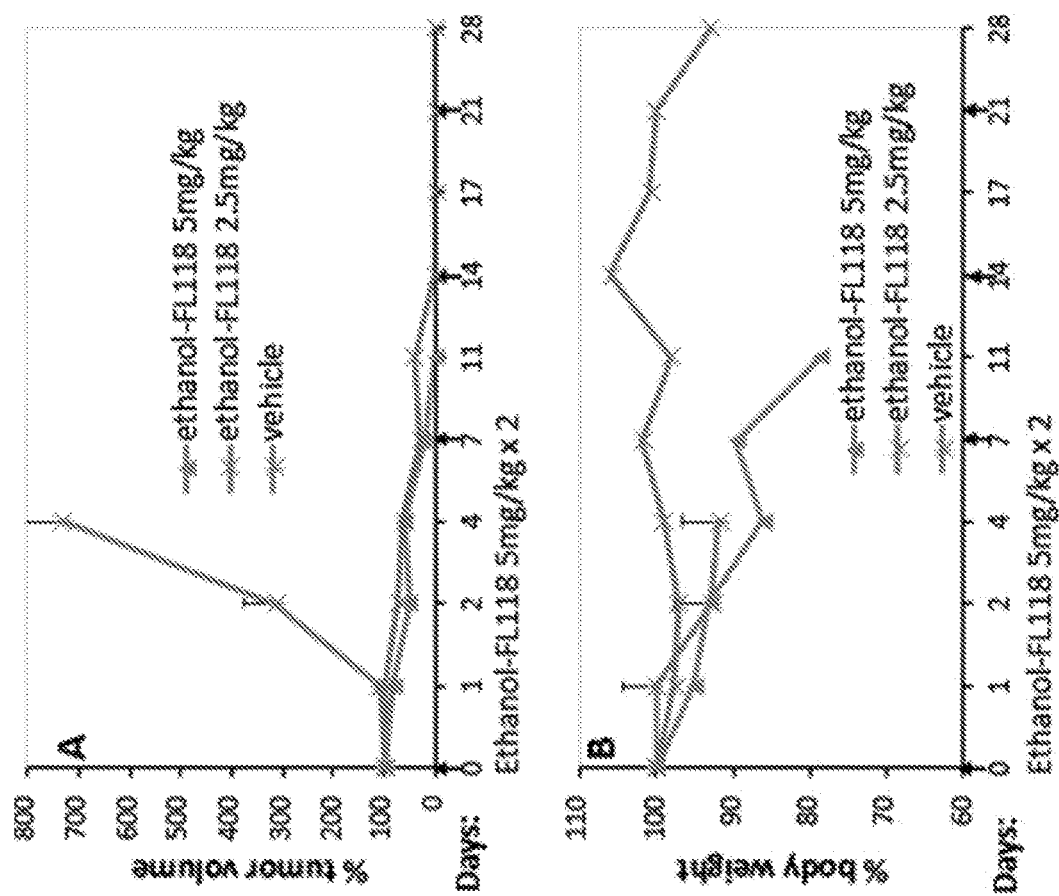
CANGET_P0003: Figure 22

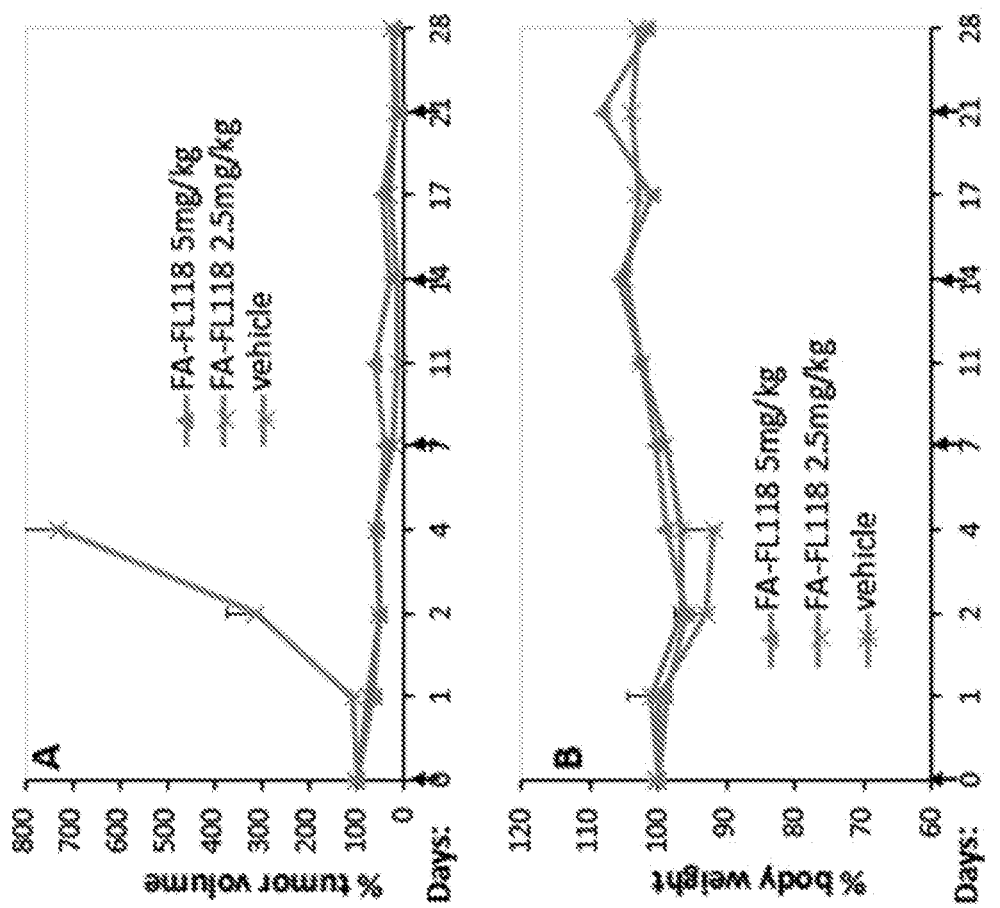
CANGET_P0003: Figure 23

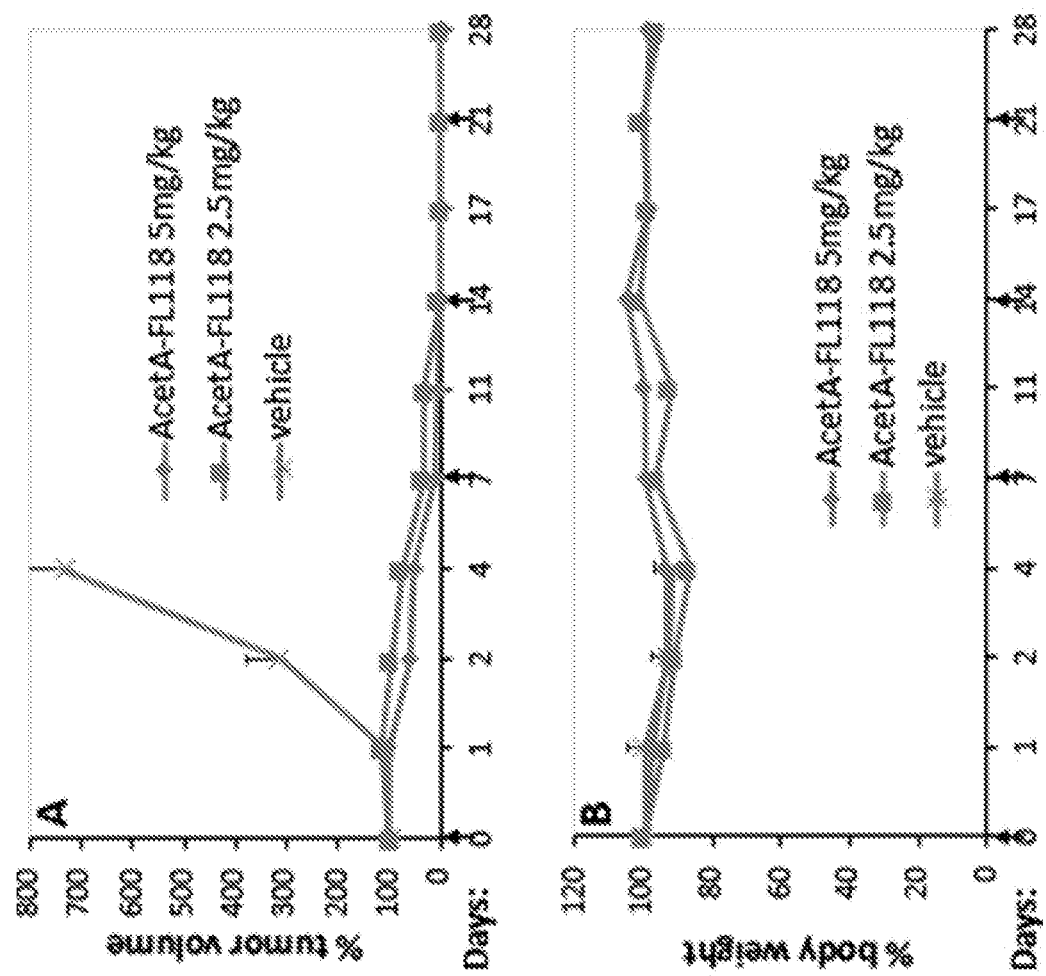
CANGET_P0003: Figure 24

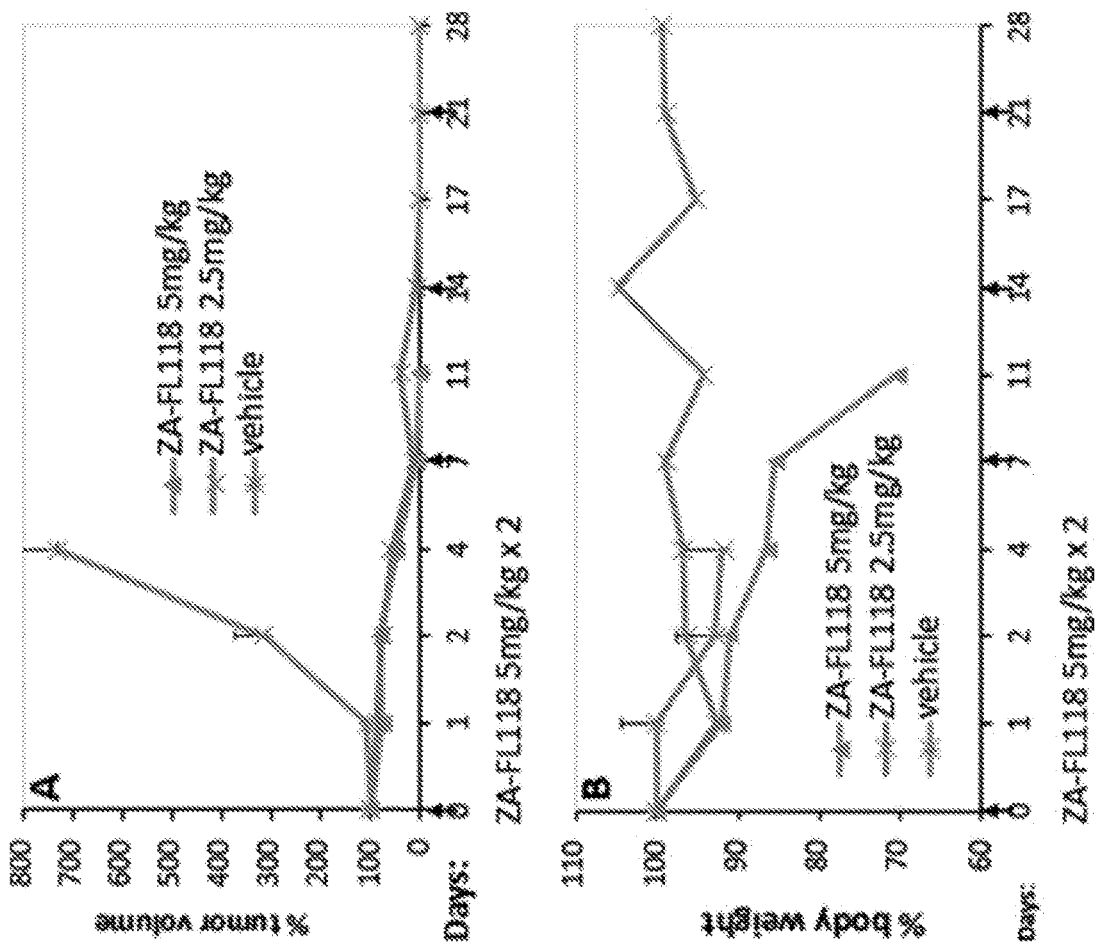
CANGET_P0003: Figure 25

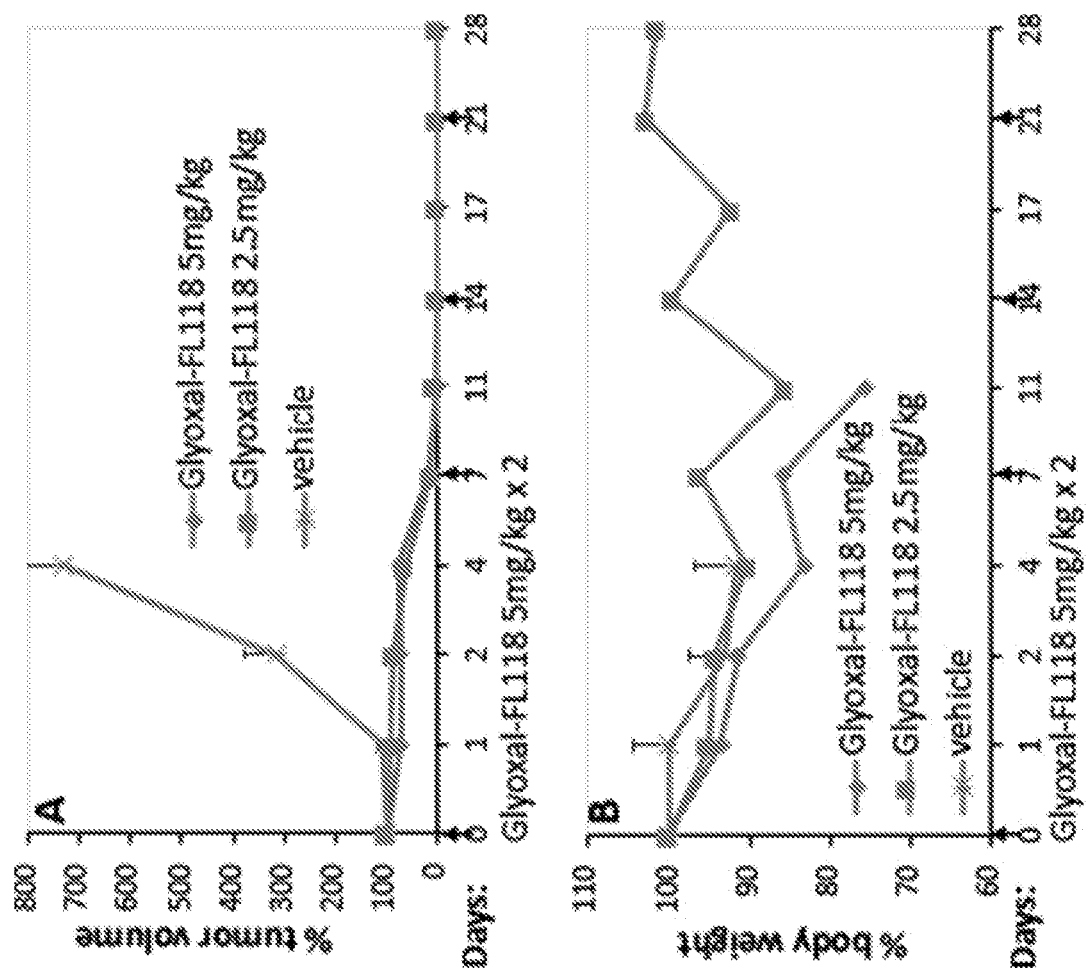
CANGET_P0003: Figure 26

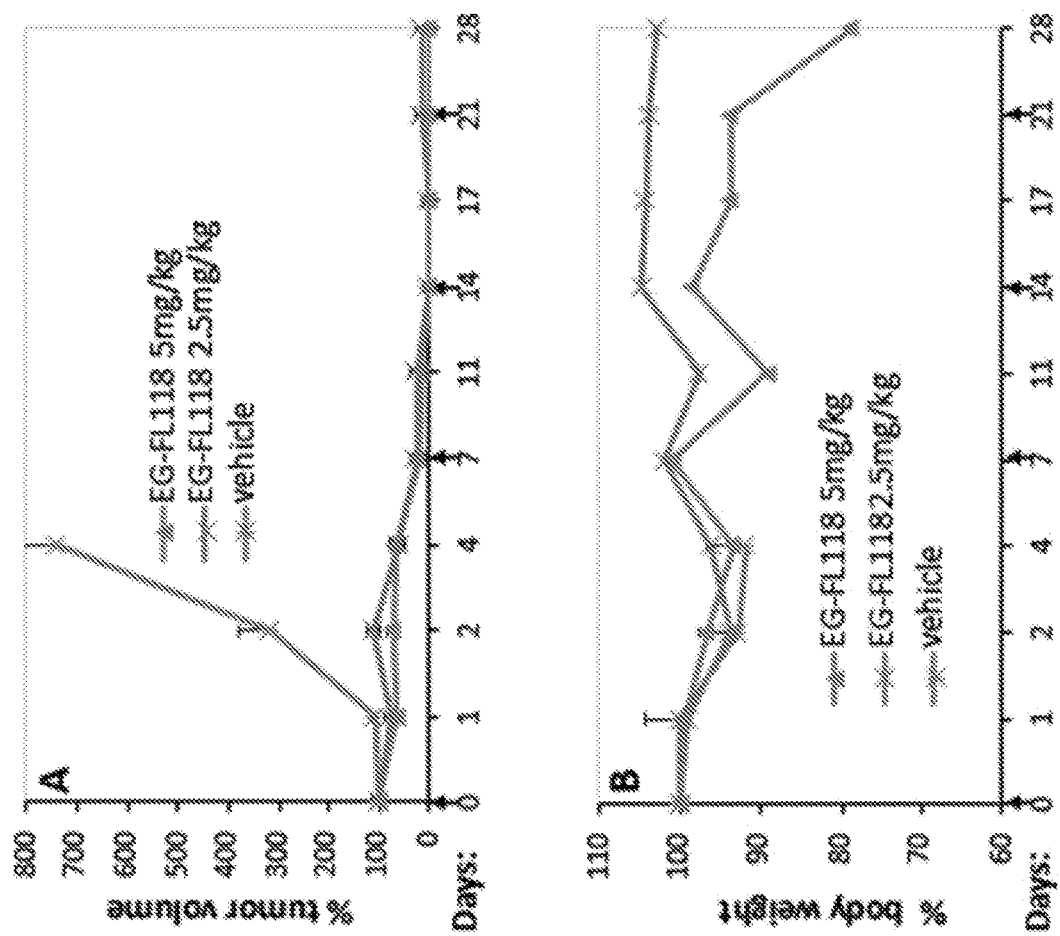
CANGET_P0003: Figure 27

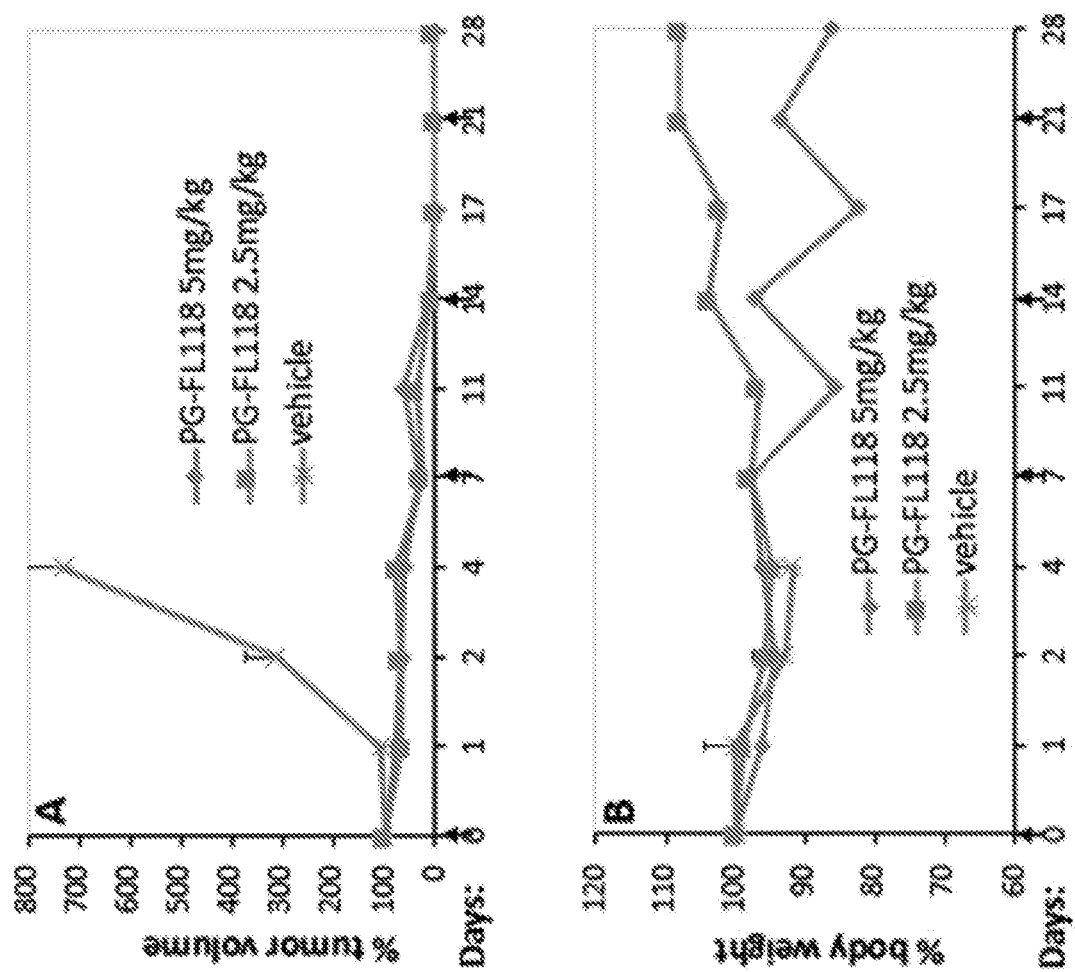
CANGET_P0003: Figure 28

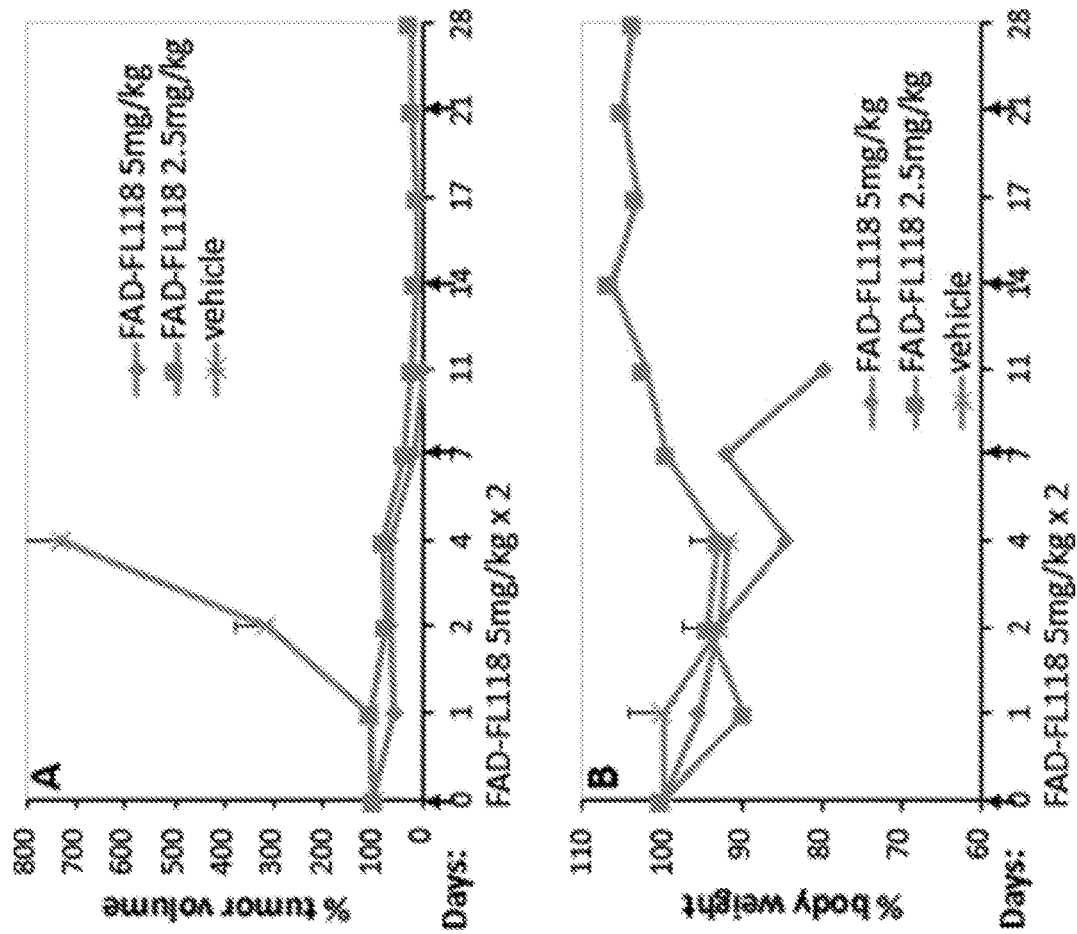
CANGET_P0003: Figure 29

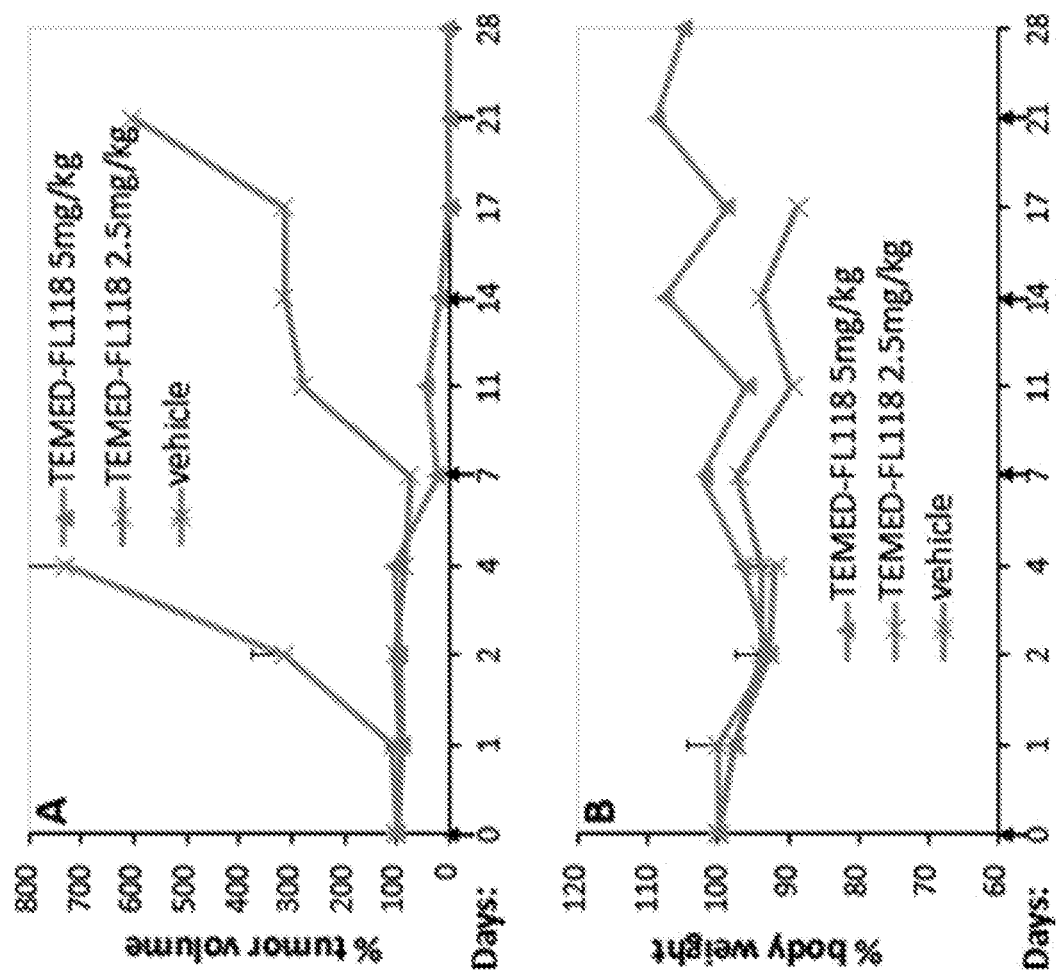
CANGET_P0003: Figure 30

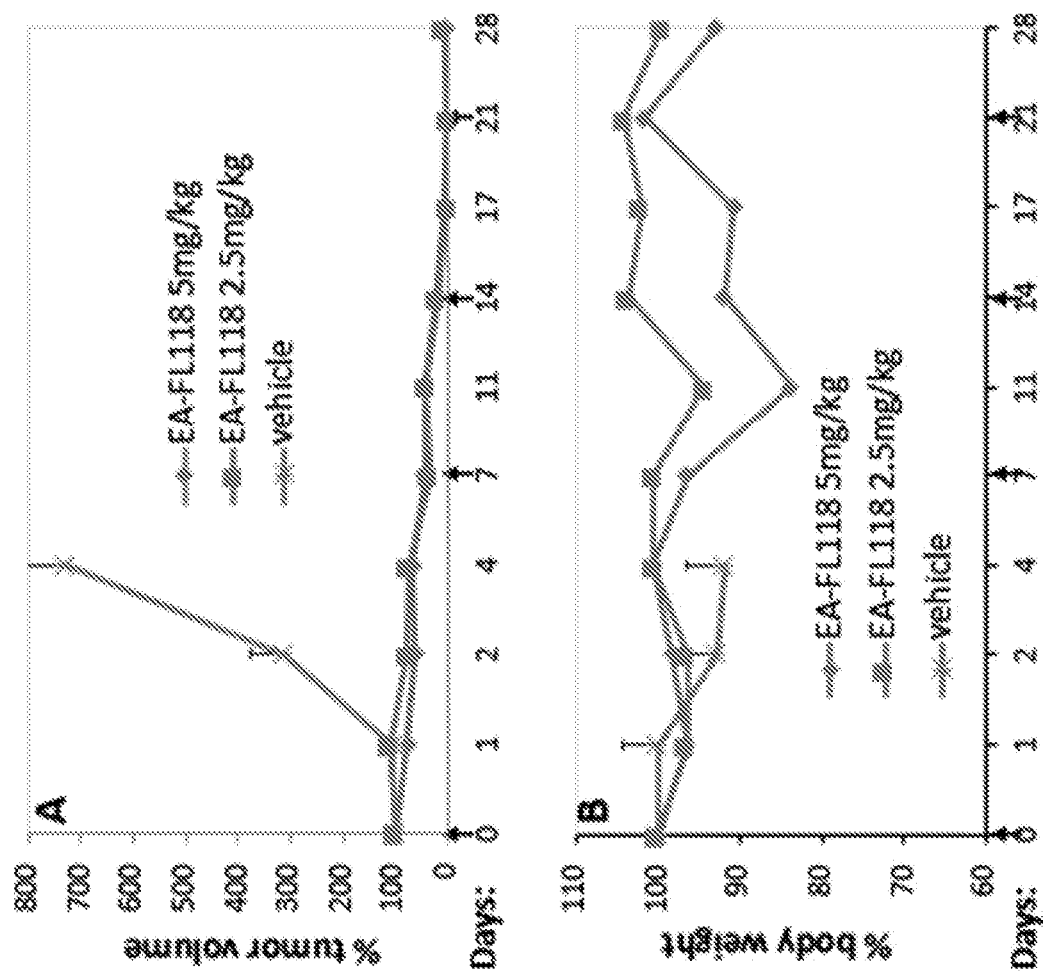
CANGET_P0003: Figure 31

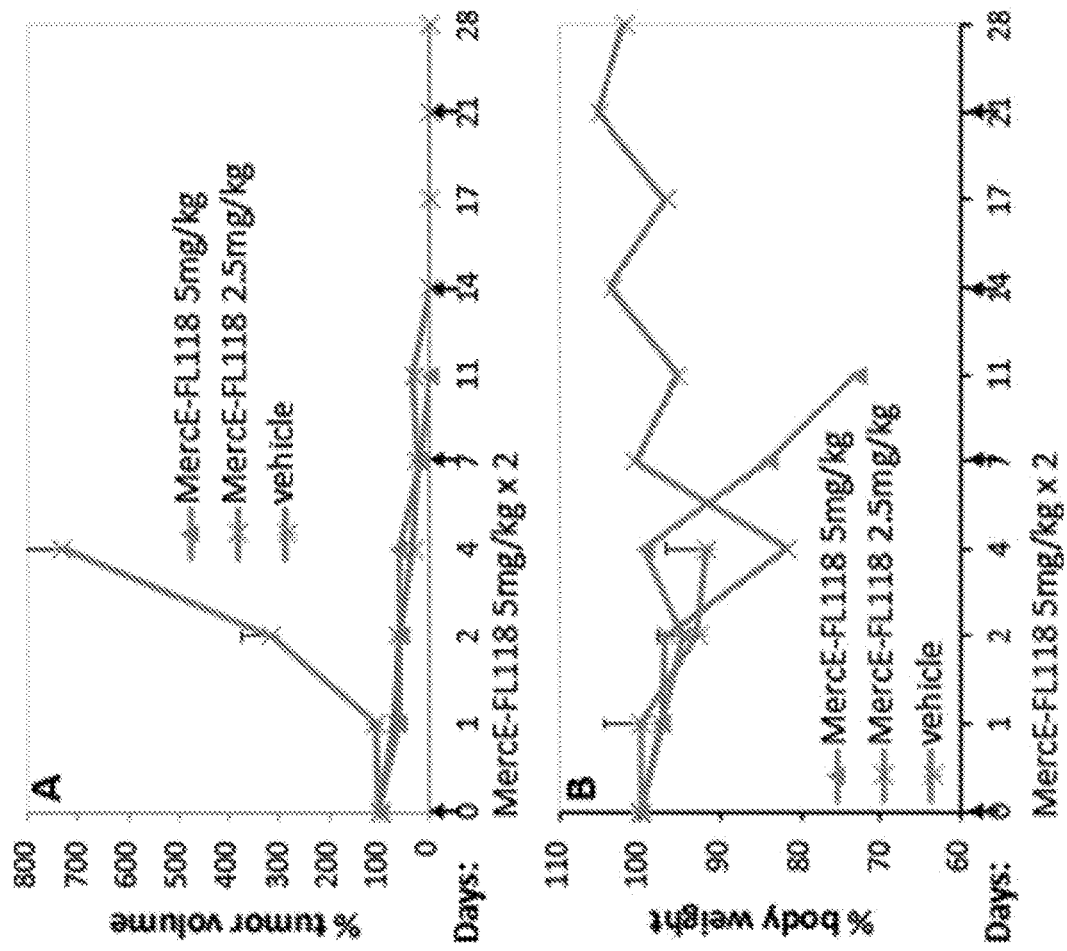
CANGET_P0003: Figure 32

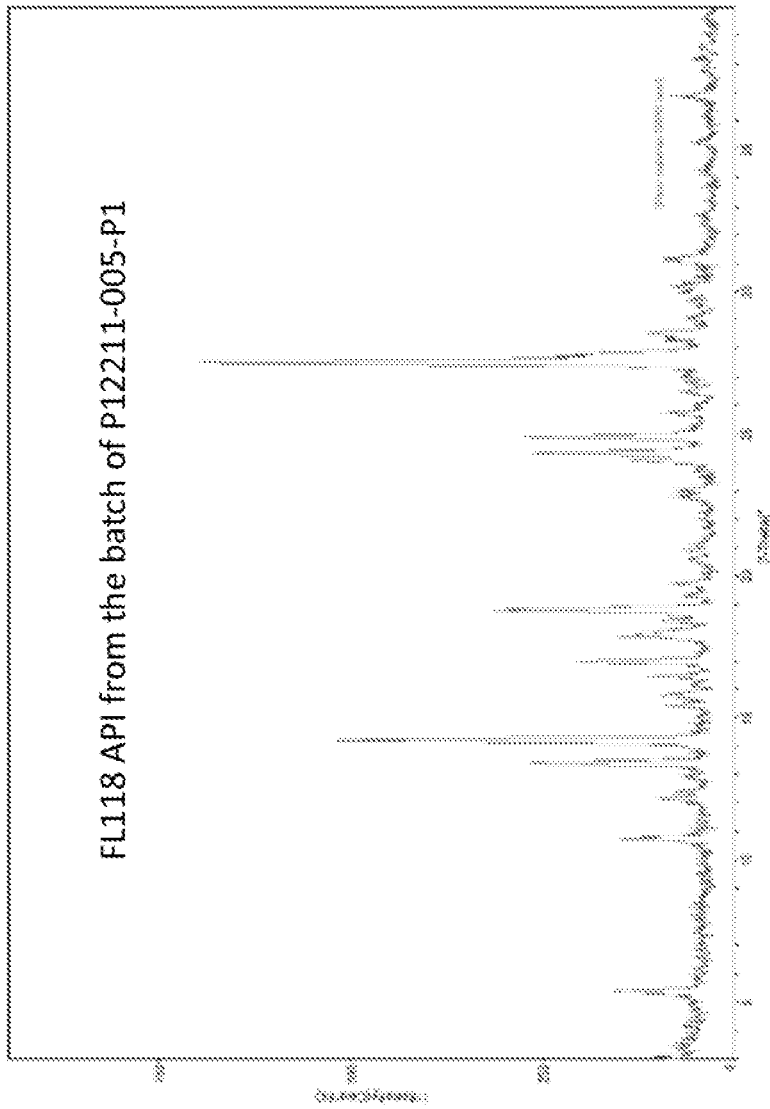

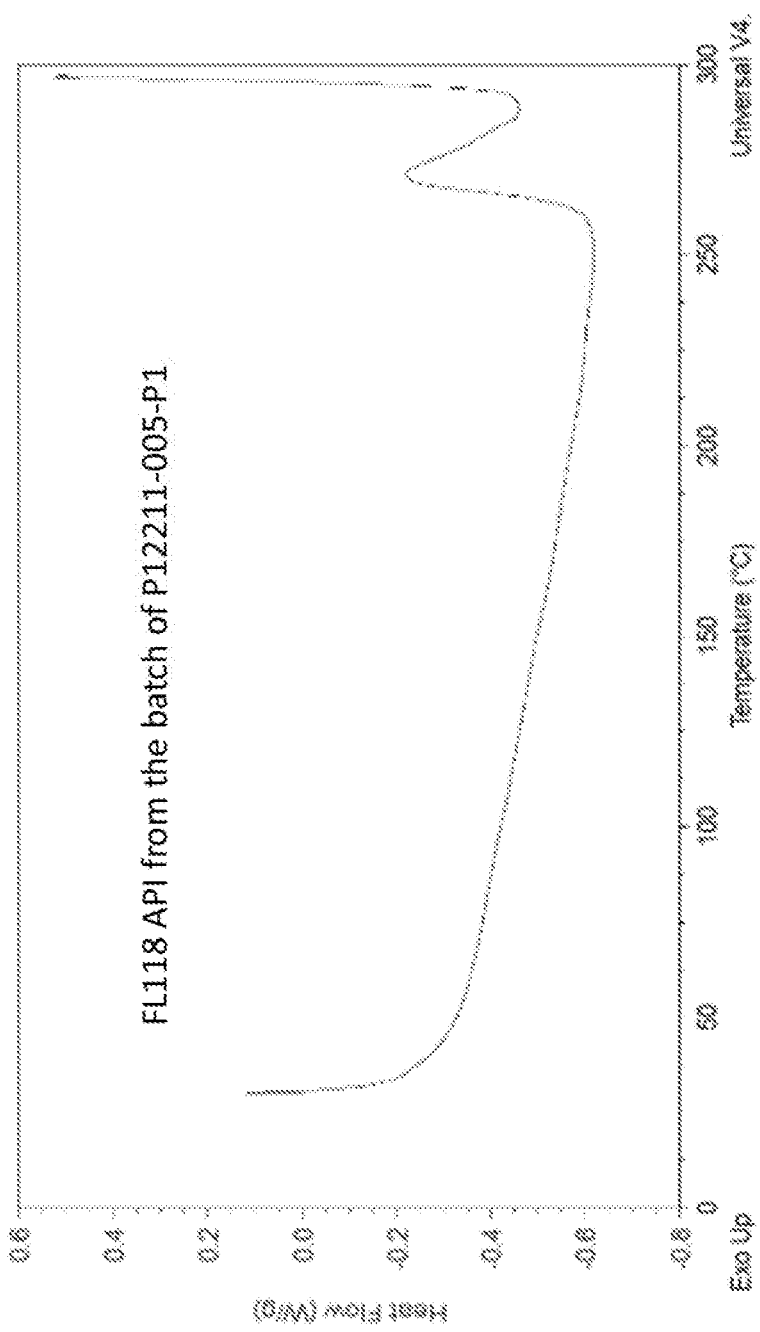
CANGET_P0003: Figure 34

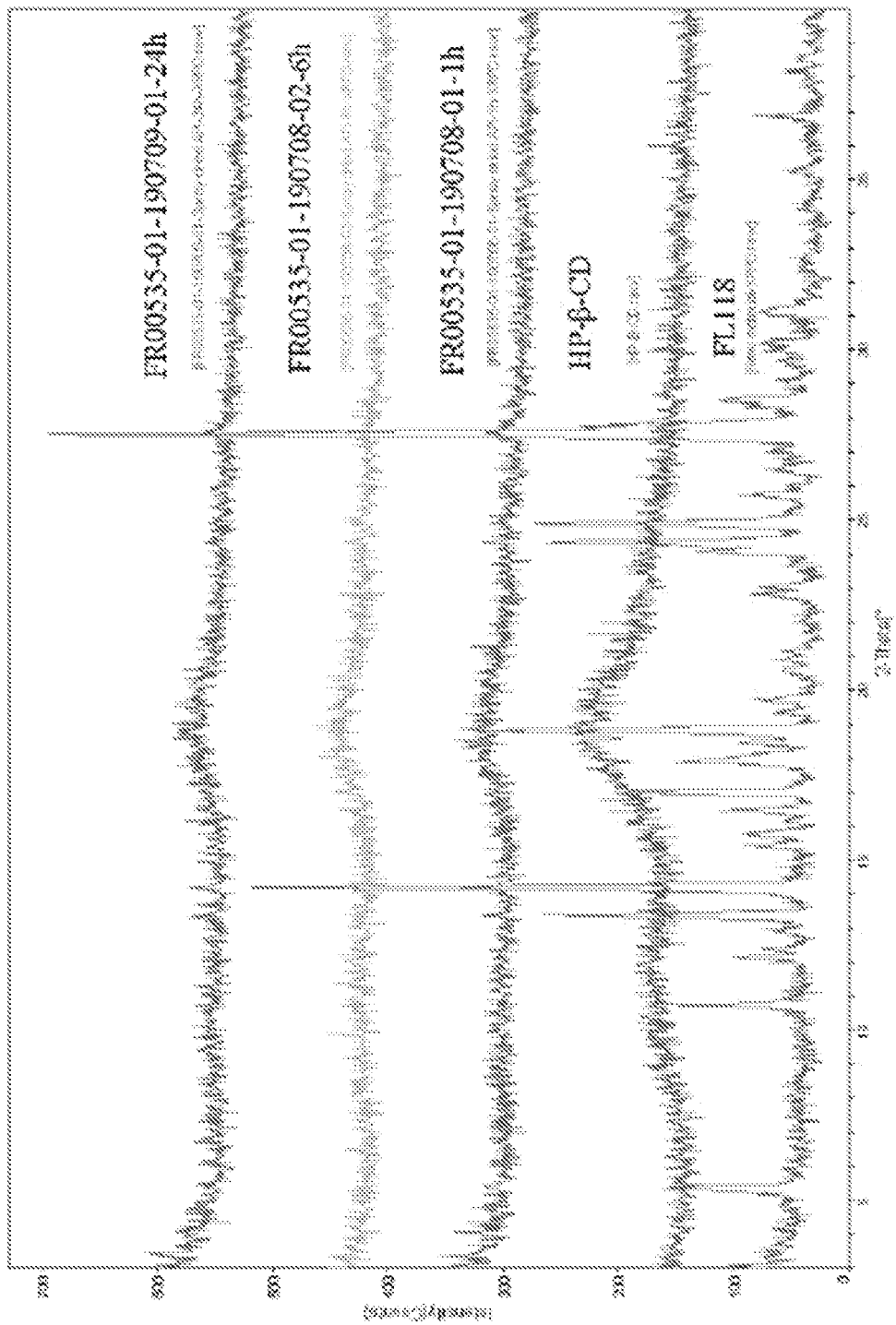
CANGET_P0003: Figure 35

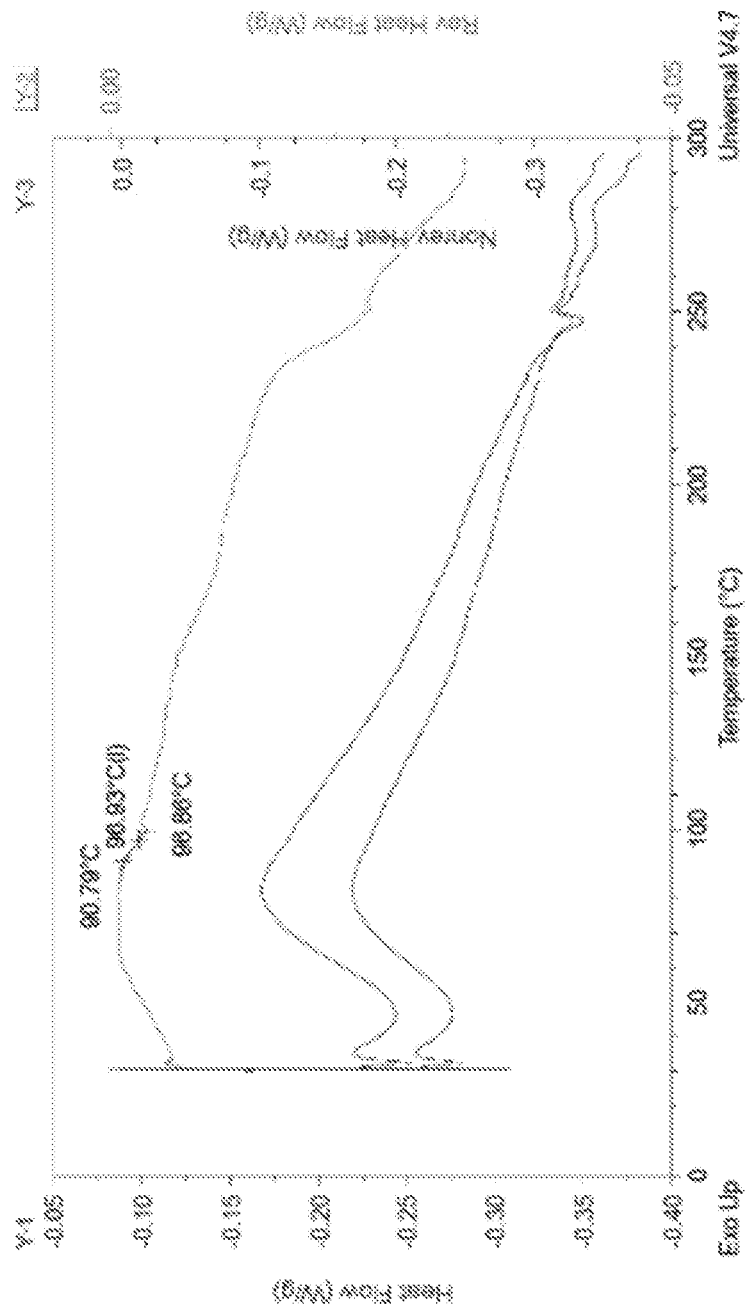
CANGET_P0003: Figure 36

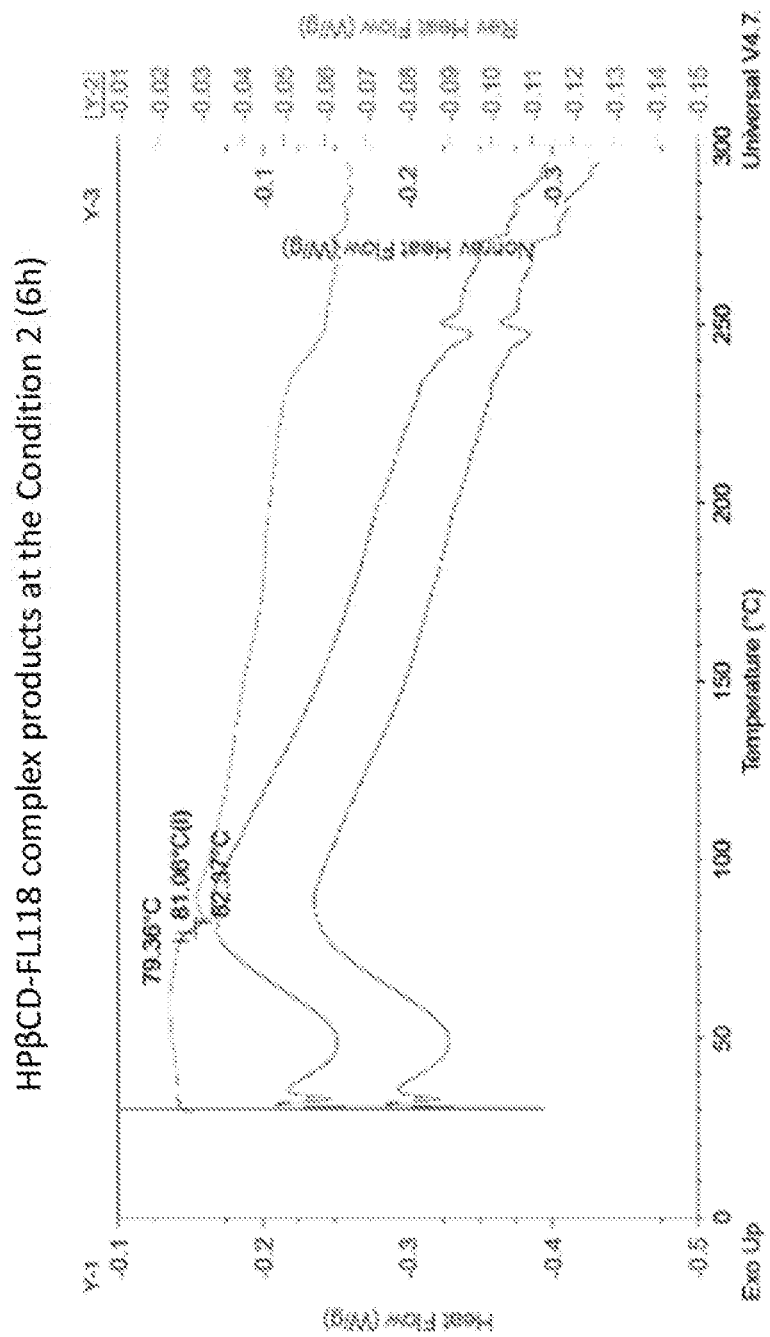
CANGET_P0003: Figure 37

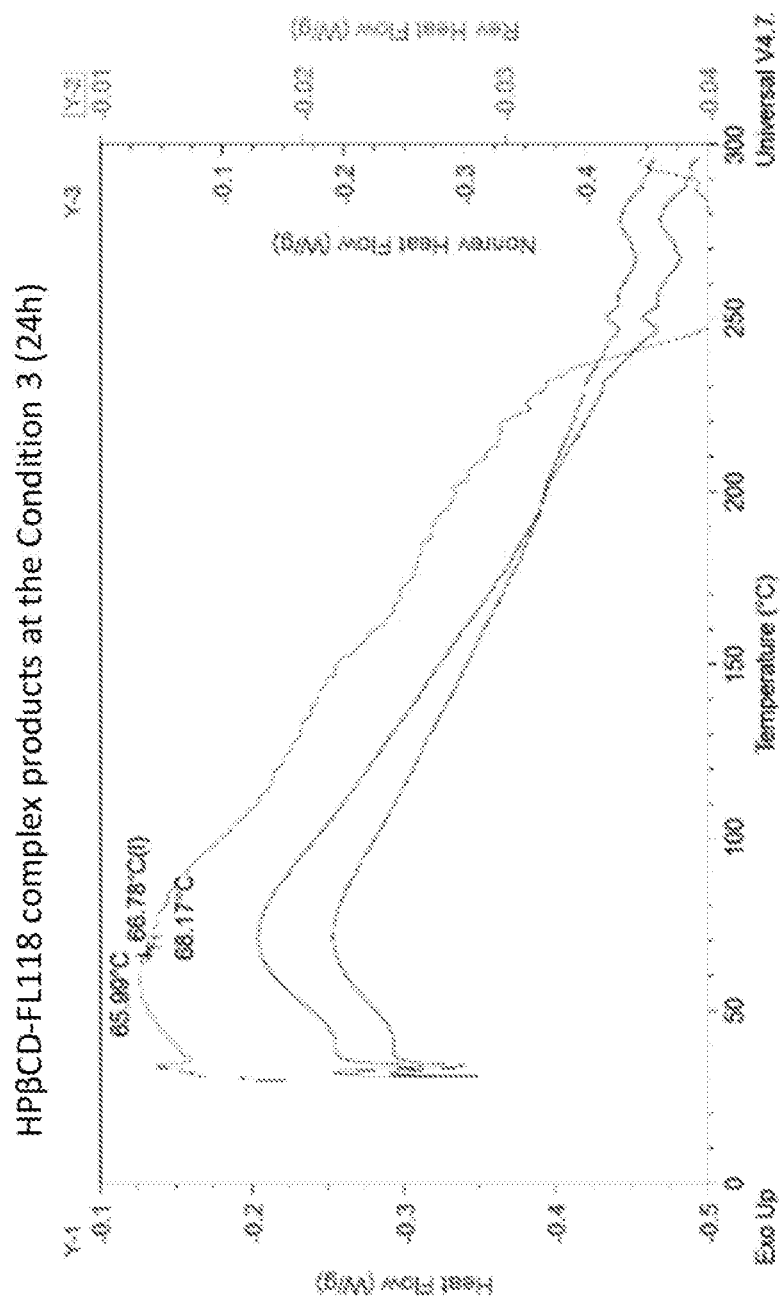
CANGET_P0003: Figure 38

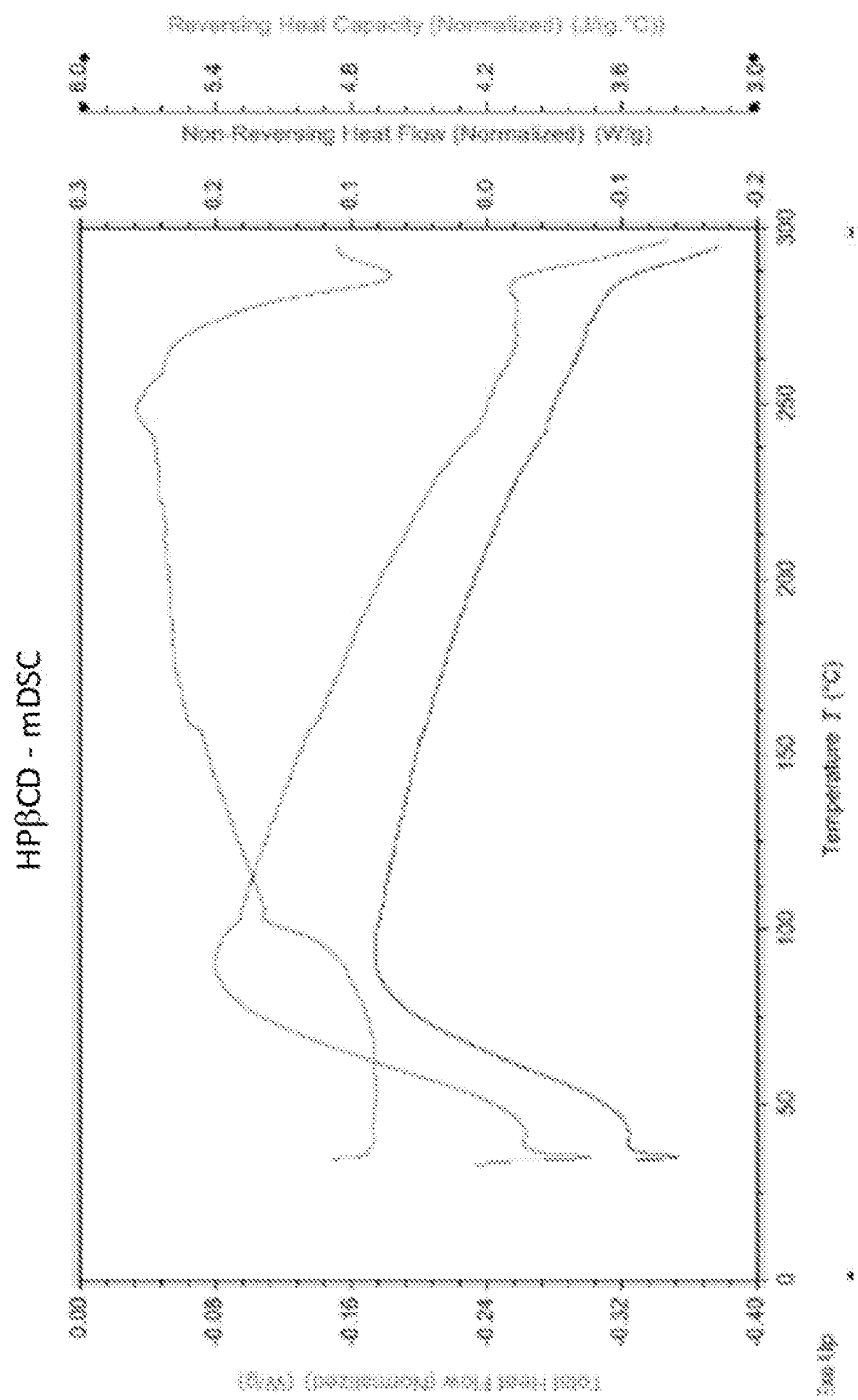
CANGET_P0003: Figure 39

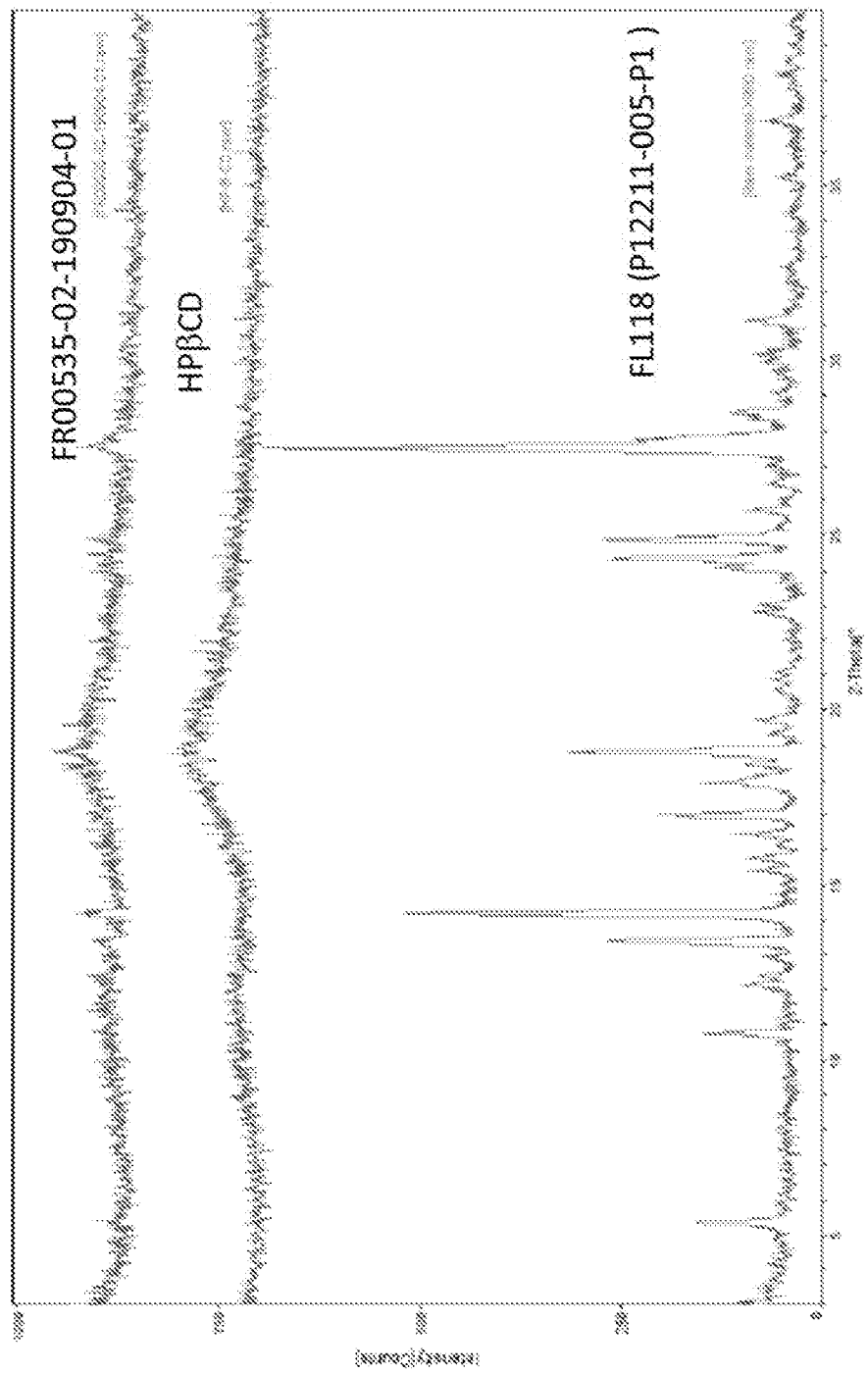
CANGET_P0003: Figure 40

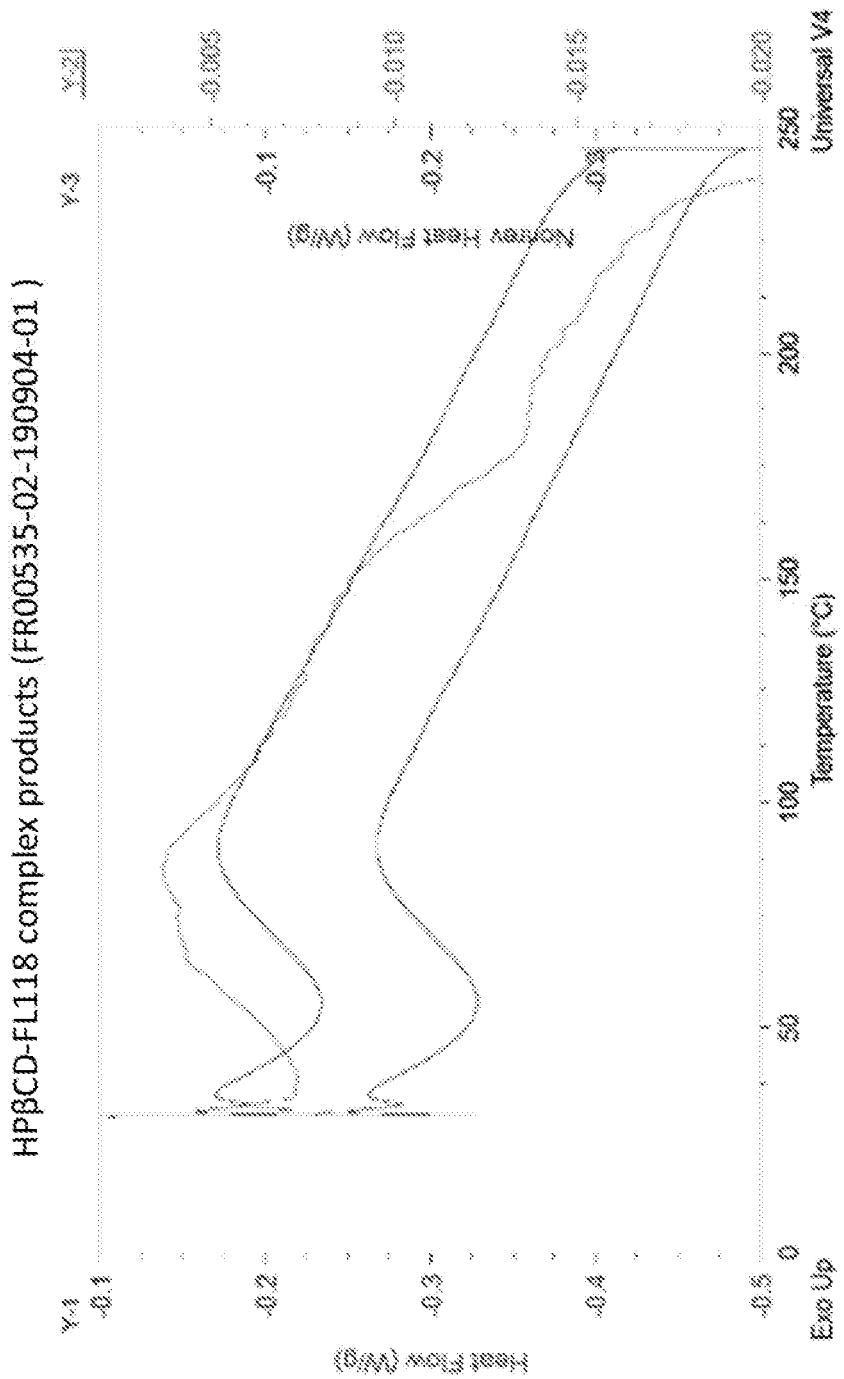
CANGET_P0003: Figure 41

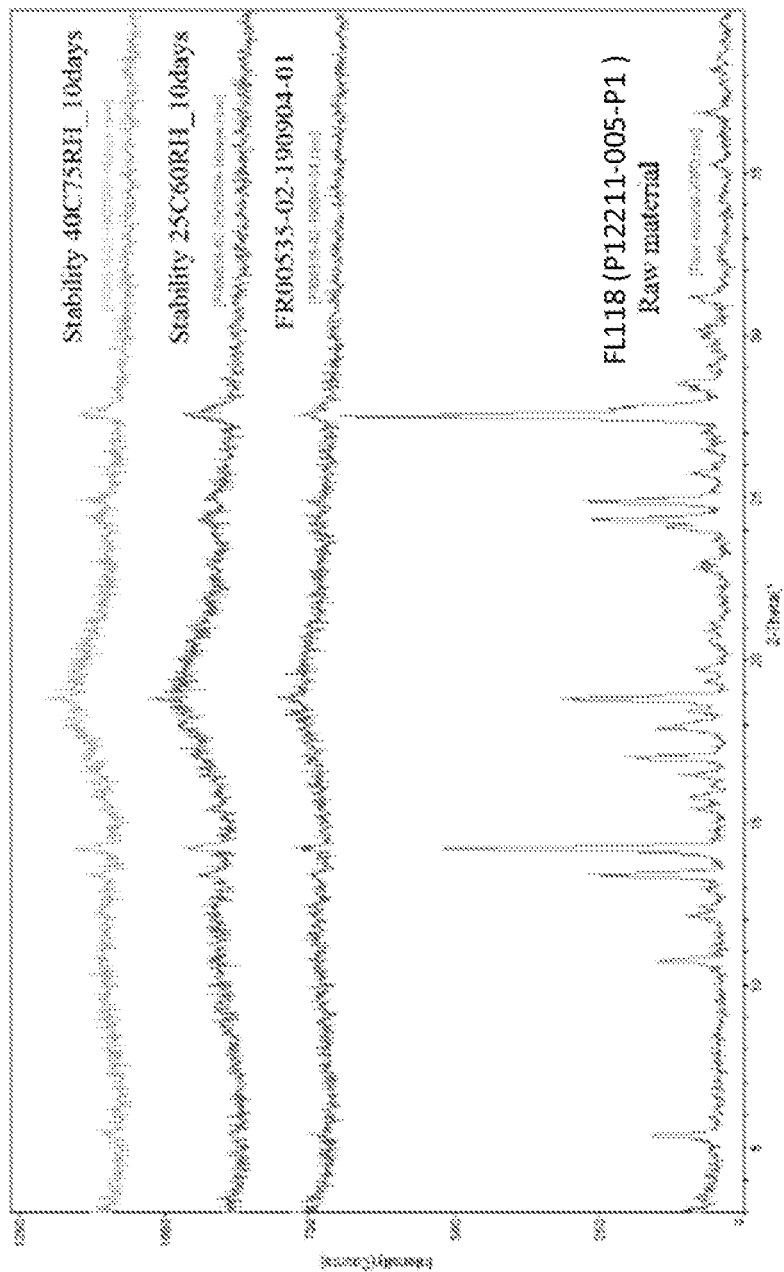
CANGET_P0003: Figure 42

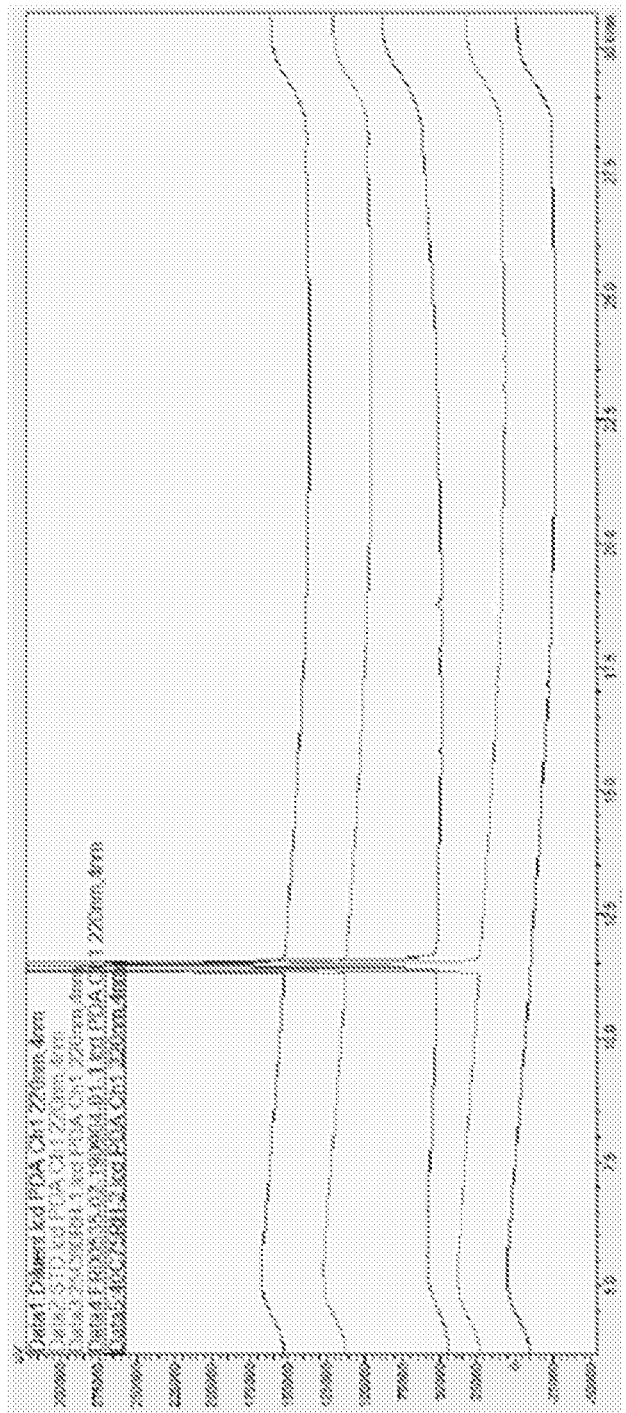
CANGET_P0003: Figure 43

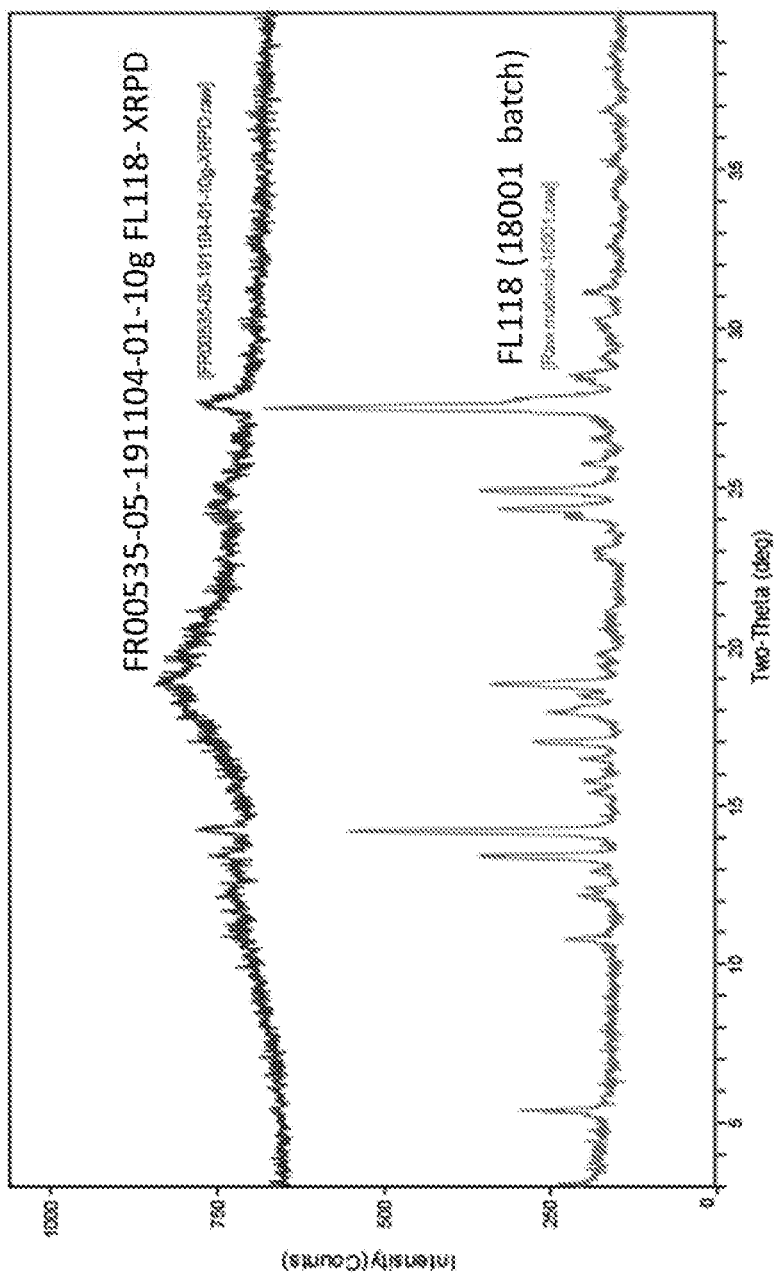
CANGET_P0003: Figure 44

ANTICANCER DRUG FL118 FORMULATION FOR TREATMENT OF HUMAN CANCER

CROSS-REFERENCE TO RELATED APPLICATIONS

The present application is filed pursuant to 35 U.S.C. 371 as a U.S. National Phase application of International Patent Application No. PCT/US2020/043153, which was filed Jul. 22, 2020, claiming the benefit of U.S. Provisional Application No. 62/876,835, filed Jul. 22, 2019. The entire text of the aforementioned applications is incorporated herein by reference in its entirety.

This PCT patent application incorporates by reference in its entirety the novel formulation and FL118 of the PCT international patent application number PCT/US2011/058558 entitled "Novel formulations of water-insoluble chemical compounds and methods of using a formulation of compound FL118 for cancer therapy" filed on Oct. 31, 2011.

STATEMENT OF GOVERNMENT-SPONSORED RESEARCH

This disclosure was made in part with United States government support under Grant Number R44CA176937 awarded by the National Cancer Institute (NCI) to Canget BioTekpharma LLC. The United States government has certain rights in the disclosure.

BACKGROUND

The present disclosure relates to cancer treatment using FL118 with improved and expanded formulation in combination with a type of immunotherapies for treatment of human cancer and neoplasm that are associated with cancer treatment-resistant and survival pathways, cancer targets and cancer biomarkers.

We have provided a lot of evidence in the PCT international patent application PCT/US2011/058558 mentioned above as well as in the PCT international patent application PCT/US2015/022095 (Use of the FL118 core chemical structure platform to generate FL118 derivatives for treatment of human disease" filed on Mar. 24, 2015) that FL118 is a highly novel anticancer drug and even used alone could produce exceptional antitumor efficacy in our formulation to eliminate human tumors in a significant percentage of animals. We have demonstrated that FL118's chemical structure appears to be a great platform for chemical generation of a series of FL118 analogues for treatment of different human cancers.

There are several aspects showing the novelty of FL118. First, FL118 is structurally similar to topotecan and irinotecan. All of these compounds are camptothecin analogs. It is well known that the mechanism of action for camptothecin (CPT) compounds, including the two United States Food and Drug Administration (FDA)-approved drugs, topotecan (trade name: Hycamtin®) and irinotecan (Trade name: Camptostar®), is through the inhibition of topoisomerase I (Top1). That is, Top1 is their therapeutic target. However, the concentration required for FL118 to show its Top1 inhibition activity is 100 to 1,000 fold higher than the concentration required for FL118 to inhibit both survivin promoter activity and cancer cell growth (Ling, et al. PLOS ONE. 2012; 7:e45571). Furthermore, in contract to the fact that CPTs show loss of antitumor activity when cancer cells reduced or lost Top1 expression/catalytic activity, the sensitivity of human xenograft tumors to FL118 is does not depend on Top1 expression; FL118 shows high antitumor sensitivity and efficacy in human cancer with low/negative Top1 expression, while some cancer with high Top1 expression may show insensitive to FL118 treatment (Li F, et al. Am J Cancer Res. 2017; 7:370-82). This is consistent with our findings that FL118 inhibition of cancer cell growth occurs at the high pM to low nM range; whereas its effects on Top1 activity require μM levels (Ling, et al. PLOS ONE. 2012; 7:e45571). Therefore, Top1 inhibition by FL118, while it may occur, is not the primary mechanism of action for FL118.

Second, while FL118 showed no inhibitory effects on control genes (cell cycle inhibitor $p21^{cip1/waf1}$, dihydrofolate reductase, human thrombin receptor, and thymidine kinase), FL118 selectively inhibits the expression of not only survivin, but also Mcl-1, XIAP and cIAP2 (Ling, et al. PLOS ONE. 2012; 7:e45571). In contrast, SN-38 (active metabolite of irinotecan) and topotecan exhibited 10-100 fold weaker to inhibit these proteins (Ling, et al. PLOS ONE. 2012;7:e45571; Ling, et al. Am J Trans Res. 2015; 7:1765-81). DNA microarray studies showed that FL118 also does not inhibit the expression of cIAP1, Bcl-2, Bcl-XL, Bcl-2, Bcl2A1, Bcl-w, Bcl-B, Bcl2L12, Bcl2L13, Bcl-G and Bcl2L15 (unpublished data), indicating additional selectivity of FL118 in its molecular targets. Furthermore, FL118 appeared to inhibit MdmX/Mdm4 (Ling, et al. Cancer Res. 2014; 74:7487-97), a critical oncogenic protein involved in p53 pathway. FL118 also inhibits key DNA damage repair regulators ERCC6 (Ling, et al. J Exp Clin Cancer Res. 2018; 37:240) and ERCC1 (Wang, et al. Am J Transl Res. 2017; 9:3676-86). Importantly, while FL118 downregulation of MdmX induced cancer cell senescence in cancer cells with wild type p53, FL118 exhibits even higher efficacy to inhibit cell growth and induce apoptosis in cancer cells without functional p53 (mutated or null) (Ling, et al. Cancer Res. 2014; 74:7487-97). Furthermore, siRNA silencing of survivin showed no effects on the expression of Mcl-1, XIAP, and cIAP2 (Ling, et al. PLOS ONE. 2012; 7:e45571), suggesting that FL118 inhibition of survivin expression is independent of its role in the inhibition of Mcl-1, XIAP and cIAP2. Independently inhibiting multiple antiapoptotic gene products (survivin, Mcl-1, XIAP, cIAP2) is important, as various combinations of these proteins are known to be simultaneously overexpressed in various stages of resistant cancers. While the entire story will need further investigation, one way for FL118 to control multiple oncogenic protein expression is due to these gene promoters under the control of a highly overlapped panel of transcriptional factors (Am J Cancer Res. 2014; 4:304-11).

Third, irinotecan, SN-38 and topotecan are the substrates of efflux pump proteins ABCG2/BCRP and Pgp/MDR1. In contrast, FL118 is not a substrate for them, and can bypass their resistance (Ling, et al. Am J Transl Res. 2015; 7:1765-81, Westover, et al. Mol Cancer. 2015; 14:92). Consistently, FL118 is orally available, and has a favorable pharmacokinetics (PK) profile (accumulated in tumor and rapidly cleared in blood stream) after intravenous administration (Ling, et al. Am J Trans Res. 2015; 7:1765-81). Furthermore, it is the new trend of research to find anticancer agents that are not ABCG2 substrates instead of using ABCG2 inhibitor for combinational treatment (Westover and Li. J Exp Clin Cancer Res. 2015; 34:159).

Fourth, FL118 both before and/or after formulation is highly stable and can be stored at room temperature or 4° C. without issue. FL118 can be put in high temperature such as at 60-80° C. for the spray-dry process for at least a period of time without any issues. FL118 also overcomes a number of other common resistance factors such as cancer cells with mutated p53, mutated APC and/or overexpression of HdmX/MdmX (Ling, et al. Cancer Res. 2014; 74:7487-97) or Kras gene mutation (unpublished observation). Again, FL118 is orally available (Li F, et al. Am J Cancer Res. 2017; 7:370-82), accumulates in human tumors in animal model, and effectively overcomes irinotecan and topotecan-resistant human tumors in animal models (Ling, et al. Am J Transl Res. 2015; 7:1765-81).

Finally, FL118 downregulates the expression of cancer stem cells (CSCs) markers (ABCG2 ALDH1A1, Oct4) and effectively decreases the invasive ability of CSCs (Wang, et al. Am J Transl Res. 2017; 9:3676-86).

Consistent with these versatile, unique features of FL118 summarized above, FL118 showed striking antitumor activity in human tumor animal models as shown in our previously filed patents (PCT/US2011/058558, PCT/US2015/022095) and in relevant publications mentioned above. FL118 exhibited significantly better antitumor activity as compared with FDA-approved anticancer drugs commonly used in clinical practice (irinotecan, topotecan, doxorubicin, 5-FU, gemcitabine, docetaxel, oxaliplatin, cytoxan and cisplatin) (Ling, et al. PLOS ONE. 2012; 7:e45571). FL118 is able to eliminate small and large volume human tumors without relapse in a high percentage of mice within the two-month experimental period (Ling, et al. PLOS ONE. 2012; 7:e45571; Zhao J, et al. Mol Pharmaceutics. 2014; 11:457-67).

Recent studies indicated that FL118 preferentially targets and kills cisplatin-resistant pancreatic cancer cells, and inhibits spheroid formation of pancreatic cancer stem cells (Ling, et al. J Exp Clin Cancer Res. 2018; 37:240). In vivo animal models of human pancreatic cancer patient-derived xenograft (PDX) studies indicated that FL118 alone effectively eliminated PDX tumors, while FL118 in combination with gemcitabine (a first line pancreatic cancer drug) eliminated the PDX tumors that showed resistant/non-sensitive to FL118 and gemcitabine treatment (Ling, et al. J Exp Clin Cancer Res. 2018; 37:240). Furthermore, FL118 toxicology studies in BALE/cj mice and beagle dogs indicated that FL118 exhibits very low hematopoietic and biochemical toxicities (Ling, et al. J Exp Clin Cancer Res. 2018; 37:240).

On the other hand, various types of approaches related to cancer immunotherapy would benefit cancer patients in one way or another in certain degree, especially in hematological cancers; immuno-cancer therapy is attractive because it uses the inner immune system against cancer; this could be sustained for potential long-lasting immune responses in vivo as soon as formed. However, only about up to 20% cancer patients may well respond to immunotherapy, and also in many (if not most) cases, immuno-cancer therapy alone would not obtain the results good enough for cancer patients.

In multiple myeloma (MM) the most impressive response rates have been reported for the recently approved monoclonal antibodies, daratumumab (trade name: Darzalex®), isatuximab (trade name: Sarclisa®) (both anti-CD38), and elotuzumab (trade name: Emplicity®) (anti-SLAMF7). In addition to these FDA approved antibody therapies, bispecific antibodies that direct T-cells to MM cells, and T-cells that are genetically engineered to express Chimeric Antigen Receptors (CAR T-cells) are rapidly entering the immunotherapy area as highly appealing strategies. Among the target antigens, the BCMA antigen is most extensively studied in the context of MM-targeting therapy, followed by SLAMF7, GPRC5D, CD38 and CD138. BCMA-targeting CAR T-cell therapy showed that, irrespective of antibody origin (human or marine) or co-stimulatory domain (CD28 or 4-1BB) implemented in the CAR design, overall response rates are high, generally above 80%, but that many patients experience short remissions and develop relapses (Raje N, et al. N Engl J Med. 2019, 380:1726-1737; Zhao W H, et al. J Hematol Oncol. 2018, 11:141; Xu J, et al. Proc Natl Acad Sci USA. 2019, 116:9543-9551). Relapses of targeted immunotherapy also occur after antibody therapies and involve resistance mechanisms different than target antigen reduction (Nijhof I S, et al. Blood. 2016, 128:959-970). These and many other lines of evidence indicate that MM similar to its ability to escape from conventional chemotherapy and proteasome inhibitors, is able to escape from potentially very powerful immunotherapies. Currently, immunosuppression, immune exhaustion, and target antigen downregulation are considered major mechanisms of cancer immune escape. In addition, over the past years, we and other investigators have provided evidence that MM cells can develop intrinsic resistance against cytotoxic killer mechanisms of immune cells through the intensive cross-talk with bone marrow mesenchymal stromal cells (BMMSCs), similar to what has been observed for drug resistance. Specifically, we have shown that BMMSCs can protect MM-cells from lysis by MM-reactive $CD4^+$ and $CD8^+$ cytotoxic T-cells (CTL) as well as by daratumumab-redirected NK-cells. We demonstrated that this mode of immune escape is mainly induced by direct BM accessory cell-MM-cell contact and involves the upregulation of anti-apoptotic proteins Survivin and Mcl-1 in MM-cells (de Haart S J, et al. Haematologica. 2016, 101:e339-342; de Haart S J, et al. Clin Cancer Res. 2013, 19:5591-5601).

SUMMARY OF THE DISCLOSURE

In the present disclosure, we have described the newly discovered improved and expanded formulation of anticancer drug using FL118 as an example. We have also described the immunotherapies in combination with FL118 for treatment of human cancer using MM as an example cancer type. We provided examples of FL118 new formulation compositions, processes and the formulated FL118 product analyses. We also provided examples of immunotherapy alone and in combination with FL118 for treatment of MM cancer.

The present disclosure provided the FL118-relevant newly invented formulation composition and process to increase cancer treatment efficacy and multiple options for patients with resistant tumors. The expanded novel formulation composition and process will be described in details in the sections of "Pharmaceutical Compositions" and "Pharmaceutical Formulation Process" as well as in the section of "Examples". The new combinational treatment concept using FL118 in combination with immunotherapy is identified in FIG. 1. We demonstrated in our examples (1) that the unique combination of FL118 with immunotherapy works better than either alone for certain resistant and metastatic cancer, and (2) that newly invested expanded and improved FL118 formulation obtained useful FL118 product status and quality information based on the analyses of several parameters including (a) the Crystal versus amorphous status of FL118 versus FL118 product, FL118 product miscibility and the FL118 drug load in the formulated FL118 product.

The present disclosure provides a matter and composition of the new disclosure-expanded formulation of FL118, methods of combination of FL118 with immunotherapy composition as an innovative strategy to treat human disease including cancer.

In one embodiment, the disease is one or more cancers selected from blood cancers, multiple myeloma, leukemia, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, lymphoma, Hodgkin's disease, non-Hodgkin's disease; and solid tumors, fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma small cell lung carcinoma, bladder carcinoma, epithelial carcinoma, glioma, glioblastoma, glioblastoma multiforme, astrocytoma, medulloblastoma, craniopharyngioma, ependymoma, pinealoma, hemangioblastoma, acoustic neuroma, oliodendroglioma, Schwannoma, meningioma melanoma, neuroblastoma, retinoblastoma, thymoma or any combination thereof.

In suitable embodiments, the one or more cancers are one or more metastatic cancers, primary tumors, refractory cancers, progressive cancers, invasive cancers, solid tumors, disseminated tumors or hematological cancers. In illustrative embodiments, the one or more cancers are refractory to one or more therapeutic indications. In illustrative embodiments, the refractory cancer phenotype comprises expression of one or more resistance markers selected from the group reported in our previous disclosure (PCT/US2015/022095) that consists of, but not limited to, survivin, Mcl-1, XIAP, cIAP2, ABC transporter proteins, hypoxia inducing factor 1α (HIF-1α), Hdm2, HdmX, p53, mutant APC, and/or mutant Kras. In illustrative embodiments, the ABC transporter proteins are selected from the group consisting of ABCG2, ABCC4, MDR1, MRP1, heat shock protein 60 (HSP60), stress-70 protein (GRP75), ATP-dependent RNA helicase DDX5 (p68), nucleolar RNA helicase 2 (DDX21), elongation factor 2 (EF2), pre-mRNA-splicing factor ATP-dependent RNA helicase (DHX15), Transitional endoplasmic reticulum ATPase (TERA), Transferrin receptor protein (TFR1), MAP kinase-activated protein kinase 2 (MAPK2), Catenin beta-1 (CTNB1), Early endosome antigen 1 (EEA1), Guanine nucleotide-binding protein subunit beta-2-like 1 (GBLP), Electron transfer flavoprotein subunit alpha (ETFA), Proteasome activator complex subunit 3 (PSME3), UPF0368 protein Cxorf26 (CX026), Peroxiredoxin-2 (PRDX2), Peroxiredoxin-1 (PRDX1), Thioredoxin-dependent peroxide reductase (PRDX3), Serine/arginine-rich splicing factor 3 (SRSF3), Proteasome subunit beta type-2 (PSB2), Glutathione S-transferase P (GSTP1), MAP/microtubule affinity-regulating kinase 3 (MARK3). DNA-damage inducible 1 (DDI1), tumor protein D52-like 2 (TPD52L2), calcium channel, voltage-dependent, beta 1 subunit (CACNB1), Probable G-protein coupled receptor 1 (PGPCR1), ubiquitin specific peptidase 2 (USP2), melanocortin 2 receptor (MC2R), Fibroblast growth factor 18 (FGF18), tumor protein p53 inducible protein 3 (TP53I3), CCHC-type zinc finger, nucleic acid binding protein (CNBP), WD repeat domain 22 (WDR22), Potassium voltage-gated channel subfamily E member 1 (PVGCSE-M1), ubiquitin-conjugating enzyme E2T (putative) (UBE2T), Ubiquitin-like protein 7 (ULP7), RNA binding motif, single stranded interacting protein 2 (RBMS2), Cytoplasmic tyrosine-protein kinase (BMX), and cyclin B1 interacting protein 1 (CCNB1IP1). In illustrative embodiments, the p53 is wild type, mill or a p53 mutant, or wherein there is an aberration in a canonical p53 pathway, or any combination thereof.

In some embodiments, the compound of FL118, and its pharmaceutically acceptable salt of FL118 for overcoming acute and chronic acquired and/or inherent treatment resistance is administered to the subject separately, sequentially or simultaneously with one type of immunotherapeutic approaches including but may not be limited to, cell-based immunotherapy, antigen-based immunotherapy, cytokine-based immunotherapy and other agents-based immunotherapy.

In illustrative embodiments, the compound of FL118 is formulated into various forms of aqueous suspension, nanoparticles or solid status such as tablet, capsules, etc. for the combination with a type of immunotherapy with a type of salt. In illustrative embodiments, the salt is a chloride, phosphate, mesylate, bismesylate, tosylate, lactate, tartrate, malate, bis-acetate, or citrate salt. In illustrative embodiments, the compound of FL118, the pharmaceutically acceptable salt of the compound of FL118, is administered in a daily to weekly to biweekly dosage from about 0.01 mg/kg to about 10 mg/kg.

In one aspect, the present disclosure provides for FL118 in a formulated state of powder formulated with a type of cyclodextrin (CD) such as -β-cyclodextrin (-β-CD), hydroxypropyl-β-cyclodextrin (HP-β-CD), sulfobutylether-β-cyclodextrin (SBE-β-CD) or another type of cyclodextrin derivatives to become an FL118-a type of CD complex through a unique formulation process.

In one aspect, the FL118-HP-β-CD complex powder, for example, is generated through first dissolving HP-β-CD into anhydrous methanol or ethanol to become a HP-β-CD-methanol solution or a HP-β-CD-ethanol solution. Then FL118 is formulated into the HP-β-CD-methanol solution or the HP-β-CD-ethanol solution to become an FL118-HP-β-CD-methanol complex suspension or an FL118-HP-β-CD-ethanol complex suspension. The FL118-HP-β-CD complex suspension is then homogenized using a dispersion homogenizer. Then removing the solvent from the homogenized FL118-HP-β-CD complex suspension through spray-dry (preferred) or lyophilization to make the FL118-HP-β-CD complex suspension become an FL118-HP-β-CD complex powder. The powder may or may not be further processed through a jet-miffing step, which will depend on the particle size requirement then.

In the other aspect, the FL118-HP-β-CD complex powder is produced through first dissolving HP-β-CD into formic acid, acetic acid, zinc acetate or glyoxal to become a HP-β-CD-solvent solution, respectively. Then FL118 is formulated into the HP-β-CD-solvent solution to become an FL118-HP-β-CD complex suspension. The FL118-HP-β-CD suspension is then homogenized using a dispersion homogenizer. Then removing the organic solvents from the homogenized FL118-HP-β-CD complex suspension through spray-dry or lyophilization to make the FL118-HP-β-CD suspension become an FL118-HP-β-CD complex powder.

The powder may or may not be further processed through a jet-milling step, which will depend on the particle size requirement then.

In the next aspect, the FL118-HP-β-CD complex is generated through first dissolving RP-β-CD into ethylene glycol (EG), propylene glycol (PG), formamide, (N,N,N',N')-tetramethyl-ethylenediamine, ethanolamide or 2-mercaptoethanol to become a HP-β-CD-solvent solution. Then FL118 is formulated into the HP-β-CD-solvent solution to become an FL118-HP-β-CD complex suspension. The FL118-HP-β-CD complex suspension is then homogenized using a dispersion homogenizer. Then removing the organic solvent from the homogenized FL118-HP-β-CD complex suspension through lyophilization or other methods to let the FL118-HP-β-CD complex in a solid or almost solid status, which can be further diluted with a defined aqueous solution before drug administration.

In some embodiments, the FL118-HP-β-CD complex powder is in turn formed aqueous suspension, capsule or tablet for combination with a type of immunotherapy for treatment of human cancer.

In the next aspect, the FL118-HP-β-CD complex powder generated in the current disclosure is made into an aqueous suspension by direct re-suspending the FL118-HP-β-CD complex powder with clinical saline with or without 1-5% propylene glycol (PG) to the 0.1-5 mg/mL of FL118 for intraperitoneal, intravenous or oral administration.

In the next aspect, the FL118-HP-β-CD complex powder in the current disclosure is directly resuspended into an aqueous suspension using clinical saline containing 1-5% propylene glycol (PG) and 1-5% polyethylene glycol 400 (PEG400) to the 0.1-5 mg/mL of FL118 for intraperitoneal, intravenous or oral administration.

In the next aspect, the FL118-HP-β-CD complex powder generated in the current disclosure is made into capsule/tablet formulation, where the formulation comprises the 5-25% FL118-HP-β-CD complex powder together with microcrystalline cellulose (MCC, 30%-80%), corn starch (0%-40%), lactose (10%-25%), colloidal silicone dioxide (1%-3%), dibasic calcium phosphate (1%-10%), magnesium stearate (0.2%-3%).

In one aspect, the disclosure entails a method for FL118 combination with a type of immunotherapy for treatment of multiple myeloma (MM).

The foregoing summary is illustrative only and is not intended to be in any way limiting. For example, the organic solvent for dissolving a type of CD can be in different ratio combination but instead of using separately as described above.

In addition to the illustrative aspects, embodiments, and features described above, further aspects, embodiments, and features will become apparent by reference to the following drawings and the detailed description.

BRIEF DESCRIPTION OF THE DRAWINGS AND TABLES

FIG. 1 shows the unique concept of FL118 in combination with a type of immunotherapeutic strategies for cancer treatment Mechanism of action of the treatment combination is outlined.

FIG. 2 shows that FL118 is effective against multiple myeloma (MM) cell lines regardless of the presence of bone marrow derived mesenchymal stromal cells (BMMSCs) and abrogates stromal cell-induced drug resistance against bortezomib and doxorubicin. (A) Luciferin (LUC)-transduced MM cell lines were treated with serial concentrations of FL118 in the presence or absence of BMMSCs derived from 12 MM patients at time of diagnosis. MM cell viability was determined by bioluminescence imaging (BLI), after 24 hours of treatment with FL118. EC50 values were determined for both culture conditions from the log dose-response using Graphpad Prism version 7. The differences in the dose response curves has been analyzed by nonlinear regression (*P<0.05; ****P<0.0001). Error bars represent the SD of four independent experiments executed in duplicate. (B) The MM cell lines MM1.s and UM9 were treated with serial concentrations of FL118 (1.0-2.0 and 3.1-12.5 nmol/L for MM1.s and UM9 respectively) and with predetermined concentrations of bortezomib (BORT; 2 and 4 nmol/L for MM1.s and UM9 respectively) or doxorubicin (DOX; 14 and 108 nmol/L for MM1.s and UM9 respectively) in the presence or absence of BMMSCs or HS-5 for 48 hours. Results are representative of three independent assays. Error bars represent the SD of duplicate cultures.

FIG. 3 shows that FL118 is more effective in relapsed and/or refractory (RR) MM as compared to newly diagnosed (ND) MM patients and that FL118 enhances melphalan and bortezomib-induced MM cell lysis. (A) Bone marrow mononuclear cell (BMMNC) samples from 15 ND and 12 RR MM patients were treated with 100 nmol/L FL118 for 24 hours. Viable CD138$^+$ CD38$^+$ MM cells were enumerated via flow cytometry. The percentage lysis of MM cells was calculated relative to untreated samples. Within the RR MM group, patients without known cytogenetic anomalies (n=5), with a deletion of chromosome 17p (n=3), and with intact chromosome 17p (n=4) are depicted with circles, squares and triangles, respectively. The bars indicate the median values. The differences between groups were tested using the Mann-Whitney test (*P<0.05). (B) Mcl-1 and Survivin expression levels (Median florescence intensity; MFI) in CD138$^+$ CD38$^+$ MM cells of untreated BMMNCs from seven ND and seven RR patients were determined by flow cytometry. The bars indicate the median values. The differences between groups were tested using the Mann-Whitney test (**P<0.01; ns, not significant). (C) Mcl-1 and Survivin expression levels (MFI) in CD138$^+$ CD38$^+$ MM cells that were untreated or treated with FL118 for 16 hours. The differences between groups were tested using Wilcoxon matched-pairs rank test (*P<0.05: ns, not significant). Note that Survivin modulation was more pronounced in RR MM patients (P=0.031) as compared to ND MM patients (P=0.078). (D) BMMNCs from MM patients were treated with predetermined suboptimal concentrations of FL118 (12.5-100 nmol/L) and/or with predetermined suboptimal concentrations of melphalan (5-10 μmol/L) (n=10) or bortezomib (2-3 nmol/L) (u=9) for 48 hours. The observed lysis levels (obs) upon co-treatment were compared to the expected lysis levels (exp), which were calculated with the assumption that the combinatorial effect is achieved by additive effects (Bliss-model) thus using the following formula: % expected lysis=(% lysis with FL118+% lysis with second drug)−% lysis with FL118×% lysis with second drug. The null hypothesis of "additive effects" was rejected if the observed values were significantly different than the expected values. Bars represent the median values of the groups. The statistical differences between the indicated groups were calculated using the Wilcoxon matched-pairs rank test (*P<0.05: **P<0.01; ns, not significant).

FIG. 4 shows that FL118 exhibits effective in vivo anti-tumor activity in multiple myeloma. (A) Schematic overview of the experimental design: Hybrid scaffolds, in vitro coated with mesenchymal stromal cells (MSCs), were implanted subcutaneously at the back of RAG2−/−γc−/− mice (4 scaffolds per mice) and inoculated with tumors (LUC-transduced MM cell line UM9). After 1 week, mice were treated with FL118 or vehicle via i.v. administration, daily for five times (arrowed). (B) BLI images of representative mice per treatment group at week 1 (before start of treatment), week 3 (two weeks after start of treatment), and week 8 (end of the experiment). Four treatment groups included: (1) vehicle control (n=3); (2) 0.05 mg/kg FL118 (n=4); (3) 0.1 mg/kg FL118 (n=4); (4) 0.2 mg/kg FL118 (n=4). (C) Analysis of tumor loads per treatment group. BLI results are expressed as relative tumor growth with the BLI signal at week 1 set to 100% (indicated by the dashed line). Each tumor growth curve represents mean with SD. The statistical differences between mice treated with vehicle and mice treated with FL118 were calculated using Kruskal-Wallis ANOVA (*P<0.05; **P<0.01).

FIG. 5 shows that there is minimal toxicity of FL118 on BMMSCs. A pool (n=12) of newly diagnosed-MM patient derived BMMSCs were treated with serial concentrations of FL118. Cell viability was determined by Cell TiterGlo after indicated period of time. Error bars represent the SD of three independent experiments.

FIG. 6 shows that protein expression levels of FL118 target genes in MM cell lines are not significantly altered in FL118-sensitive cell lines as compared to FL118-less sensitive cell line L363. (A) Untreated MM cells were lysed and analyzed using Western blots with corresponding antibodies as shown. Actin was used as internal controls. Independent Western blots were performed at least twice. (B) Quantified signals corrected for actin relative to RPMI 8226 from the western blot results.

FIG. 7 shows that FL118 promotes pro-apoptotic signaling in FL118 high- and intermediate-susceptible MM cell lines MM1.s and U266, but not in the low-susceptible MM cell line L363. (A) MM cell lines were treated with FL118 for 16 hours. Cells were then analyzed for FL118 target gene expression using western blots. Cleaved products of PARP and Caspase-3 are indicated as cPARP and cCaspase-3 respectively. Independent Western blots were performed at least twice. (B) Relative expression levels of indicated proteins upon treatment were plotted after correcting for the internal control Actin.

FIG. 8 shows that FL118 enhances melphalan (trade name: Alkeran)—and bortezomib (trade name: Velcade)-induced MM lysis in MM cell lines. LUC-transduced UM9, U266 and MM1.s MM cell lines were treated with FL118 and/or a drug currently used for MM treatment as shown. MM cell viability was determined by BLI after 48-hour treatment with melphalan, bortezomib or dexamethasone combined with FL118, and after 72-hour treatment with pomalidomide combined with FL118. Results are representative of three independent assays. Error bars represent the SD. The observed lysis levels (obs) upon co-treatment were compared to the expected lysis levels (exp). Combination Index (CI) values for the co-treatment of FL118 with melphalan or with bortezomib were quantified with the Chou-Talalay method. CI values could not be determined for pomalidomide or dexamethasone as we were unable to reach a dose-response curve for these drugs including data points above and below IC50.

FIG. 9 shows that FL118 enhances anti-DR5 antibody-mediated MM cell lysis and overcomes BMMSC-induced immune resistance. LUC-transduced DR5$^+$ MM1.s cell line was treated with anti-DR5 antibody Drozitumab (Absolute Antibody) and/or FL118 for 24 hours. Effector PBMCs were derived from healthy donors. Error bars represent means with SD of duplicate or triplicate cultures. The observed lysis levels upon co-treatment were compared to the expected lysis levels. The statistical differences between the indicated groups were calculated using unpaired T-test (p-value is shown in the figure).

FIG. 10 shows that no significant difference in CAR transduction efficiency or phenotype of CAR T-cells. (A) LNGFR, dsRED, and 4-1BBL expression was measured with flow cytometry analysis in respectively BBz-, 28z-, and 28zBBL-CAR T-cells to determine percentage of T-cells that express CAR constructs. Error bars represent means with SD. (B) Percentage of CAR$^+$ T-cells that express CD8 or CD4. (C) Percentages of CAR$^+$ T-cells with either naive (CD45RA$^+$/CD62L$^+$), central memory (CD45RA$^-$/CD62L$^+$), effector memory (CD45RA$^-$/CD62L$^-$), or effector (CD45RA$^+$/CD62L$^-$) phenotype. Statistical analysis was done using Kruskal-Wallis tests and subsequent multiple comparison. No statistical differences were observed.

FIG. 11 shows that the inverse correlation between the efficacy of CAR T-cells to induce MM cell lysis and the degree of BMMSC-mediated immune resistance against the CAR T-cells. The LUC-transduced UM9 cell line was cultured in the presence or absence of BMMSCs and treated with serial effector to target (E:T) ratios of indicated CAR T-cell targeting CD138 (A), BCMA (B), or CD38 (C) for 24 hours. Error bars represent means with SD of duplicate cultures. (D) For each independent assay that was performed with CAR T-cells generated from different healthy PBMC donors indicated with 'N', the EC50 E:T ratio was calculated from the dose-response curve in monoculture condition and illustrated with the corresponding percentage of inhibition of lysis upon co-culture. Correlations were calculated using Pearson correlation coefficient. Results in A-C are representative of indicated 'N' in D (p-value is shown in the figure).

FIG. 12 shows that BMMSC-mediated protection of patient MM cells against moderately lytic CAR T-cells (A) BMMNC samples from 6 MM patients were treated with selected CAR T-cells at an E:T ratio of 1:3, in the presence or absence of BMMSC for 24 hours. Viable CD138$^+$ CD38$^+$ CD45$^{dim}$ MM-cells were enumerated via flow cytometry. Bars represent the median values. (B) Expression level of target molecules CD138, BCMA, and CD38 on MM-cells in untreated BMMNC samples cultured in the presence or absence of BMMSCs. The statistical differences between the indicated groups were calculated using paired t-tests (p-value is shown in the figure).

FIG. 13 shows no correlation between BMMSC-mediated inhibition of patient MM-cell lysis by CAR T-cells and BMMSC-mediated downregulation of target antigens on primary MM cells. BMMNC samples from 6 MM patients were treated with CD138 CAR T-cells (A), BCMA$^{C11D5.3}$ CAR T-cells (B), or BBz-CD38$^{B1}$ CAR T-cells (C) in the presence or absence of BMMSC for 24 hours, similar as illustrated in FIG. 12. Antigen expression level on MM-cells was measured by flow cytometry. Graphs illustrate the percentage of CAR T-cell-induced MM cell lysis that is reduced by BMMSCs against the percentage of concerning target antigen on MM cells that is downregulated by BMMSCs. Correlations were calculated using Pearson correlation coefficient.

FIG. 14 shows that the cellular mechanism of inhibition of CAR T-cell mediated MM-cell lysis by BMMSCs. (A) LUC-transduced UM9 cell line (squares), MM1.s cell line (triangle), and BMMNC samples from 3 MM patients (circles) were treated with selected CAR T-cells at an E:T ratio of 1:1, in the presence or absence of BMMSC for 24 hours. MM1.s was only treated with CD138 CAR T-cells.

(B) The corresponding cell-free supernatants of killing assays were analyzed for the presence of IFNγ (B) and granzyme B (C) by ELISA. (D) LUC-transduced UM9 cell line was cultured in the presence or absence of BMMSCs in a 96-well plate allowing direct cell-cell contact or separated by a transwell system allowing only the transfer of soluble factors. After 24 h of (co-)culture, the UM9 cells were treated with CD138 CAR T-cells at an E:T ratio of 3:1 for 24 hours. Error bars represent means with SD of duplicate or triplicate cultures. Results are representative of two independent assays. The statistical differences between the indicated groups were calculated using unpaired t-tests (*P<0.05; ns, not significant).

FIG. 15 shows that CAR T-cell activity against MM cell lines is not significantly affected by BMMSCs. The cell-free supernatants of killing assays with UM9 cell line and CD138-(A), BCMA$^{C11D5.3}$-(B), or BBz-CD38$^{B1}$ (C) CAR T-cells (left) were analyzed for the presence of IFNγ (center) and granzyme B (right) by ELISA. Error bars above represent SD of 'No BMSCs' and error bars below represent SD of 'BMSCs' of three (A) or two (B, C) independent assays. The statistical differences between the indicated groups were calculated using paired t-tests (*P<0.05; **P<0.01; ns, not significant).

FIG. 16 shows that the expression of anti-apoptotic proteins Survivin and Mcl-1 in MM-cells is enhanced upon adherence to BMMSCs. LUC/GFP-transduced UM9 cells were added to a confluent layer of BMMSCs. After 24 or 48 hours, soluble UM9 cells were removed by gently pipetting up and down. Adherent UM9 and BMMSCs cells were removed by treatment with Accutase. Survivin (A) and Mcl-1 (B) expression in GFP CD105$^-$ UM9 cells were determined by intracellular staining with flow analysis. Error bars represent means with SD of two independent assays. The statistical differences between the indicated groups were calculated using paired t-tests (p-value is shown in the figure).

FIG. 17 shows that FL118 does not reduce immune effector cell survival. (A) BMMNCs from four newly diagnosed MM patients and two newly diagnosed primary plasma cell leukemia (PCL) patients were treated with FL118 for 24 hours. Cell viability of T-cells (CD45$^+$ CD3$^+$) and NK cells (CD45$^+$ CD56$^+$ CD14$^-$ CD3$^-$) was determined by flow cytometry analysis. (B) PBMCs derived from healthy donors (n=4) were pre-stimulated with PMA (25 ng/mL) and ionomycin (500 ng/mL) for 24 hours and subsequently treated with FL118 for 48 hours. Cell viability of activated T-cells (CD45$^+$ CD3$^+$ CD56$^-$ CD25$^+$) was determined by flow analysis. Bars represent mean values.

FIG. 18 shows that FL118 enhances CAR T-cell-mediated MM cell lysis and overcomes CAM-IR. LUC-transduced UM9 cell line was treated with serial E:T ratios of CD138 (A), BCMA$^{C11D5.3}$ (B), or BBz-CD38$^{B1}$ (C) CAR T-cells and/or FL118 in the presence or absence of BMMSCs for 24 hours. Results are representative of three independent assays. Error bars represent means with SD of duplicate cultures. Combination Index (CI) values for the combination of FL118 with CAR T-cells in presence or absence of BMMSCs were quantified with the Chou-Talalay method as described in the Method section.

FIG. 19 shows that BMMNC samples from MM patients were treated with CD138- (red; n=4), BCMA$^{C11D5.3}$- (blue; n=3), or BBz-CD38$^{B1}$- (green; n=4) CAR T-cells and/or 10 nM FL118 in the presence or absence of BMMSC for 24 hours. Viable CD138$^+$ CD38$^+$ CD45$^{dim}$ MM-cells enumerated via flow cytometry. Bars represent the median values. The observed lysis levels upon co-treatment were compared to the expected lysis levels as described in the Method section. The statistical differences between the indicated groups were calculated using paired t-tests (p-value is shown in the figure).

FIG. 20 shows that FL118 enhances CTL- and daratumumab-mediated MM-cell lysis and overcomes CAM-IR. (A) LUC-transduced UM9 cell line was treated with serial E:T ratios of CTL 3AB11 and/or FL118 in the presence or absence of BMMSCs for 24 hours. Results are representative of three independent assays. Error bars represent means with SD of duplicate cultures. Combination Index (CI) values were quantified with the Chou-Talalay method as described in the Method section. (B) BMMNC samples from six MM patients were treated with 10 μg/mL daratumumab and/or 100 nM FL118 in the presence or absence of BMMSC for 24 hours. Viable CD138$^+$ CD38$^+$ CD45$^{dim}$ MM cells were enumerated via flow cytometry. Bars represent the median values. The observed lysis levels upon co-treatment were compared to the expected lysis levels as described in the Methods section. The statistical differences between the indicated groups were calculated using paired t-tests (p-value is shown in the figure).

FIG. 21 shows the antitumor activity and toxicity (body weight changes) of FL118 formulated with methanol-HPβCD solution. Human colorectal cancer SW620 xenograft tumors were first generated through implanting SW620 cancer cells at the flank area of SCID (severe combined immunodeficiency) mice. Then, the tumors were isolated and individual experimental mice were subcutaneously implanted with 30-50 mg non-necrotic tumor masses at the flank area of individual mice. Seven to 10 days after tumor transplantation at which the implanted xenograft tumors were grown to 100-200 mm$^3$ (defined as day 0), mice were randomly divided into the required groups for treatment vial oral administration of the formulated FL118 or vehicles with a schedule of weekly×4 (arrowed). A. FL118 efficacy on SW620 cancer cell-established xenograft tumors in SCID mice. The tumor growth curves are shown. B. SCID mouse body weight changes after treatment with vehicle or with the formulated FL118. The mouse body weight curves are shown.

FIG. 22 shows the antitumor activity and toxicity (body weight changes) of FL118 formulated with ethanol-HPβCD solution. Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 23 shows the antitumor activity and toxicity (body weight changes) of FL118 formulated with formic acid (FA)-HPβCD solution. Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 24 shows the antitumor activity and toxicity (body weight changes) of FL118 formulated with acetic acid (AcetA)-HPβCD solution. Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 25 shows the antitumor activity and toxicity (body weight changes) of FL118 formulated with zinc acetate (ZA)-HPβCD solution. Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 26 shows the antitumor activity and toxicity (body weight changes) of FL118 formulated with glyoxal-HPβCD solution. Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 27 shows the antitumor activity and toxicity (body weight changes) of FL118 formulated with ethylene glycol (EG)-HPβCD solution. Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 28 shows the antitumor activity and toxicity (body weight changes) of FL118 formulated with propylene glycol (PG)-HPβCD solution. Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 29 shows the antitumor activity and toxicity (body weight changes) of FL118 formulated with formamide (FAD)-HPβCD solution. Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 30 shows the antitumor activity and toxicity (body weight changes) of FL118 formulated with N,N,N',N'-tetramethyl ethylene diamine (TEMED)-HPβCD solution. Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 31 shows the antitumor activity and toxicity (body weight changes) of FL118 formulated with ethanolamide (EA)-HPβCD solution Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 32 shows the antitumor activity and toxicity (body weight changes) of FL118 formulated with mercaptoethanol (MercE)-HPβCD solution. Experimental human colorectal cancer SW620 xenograft tumor SCID mice set up and follow-up oral treatment are the same as described in FIG. 33. A. FL118 efficacy on SW620 xenograft tumors in SCID mice. The tumor growth curves are shown. B. SCID mouse body weight changes after treatment with the formulated FL118 or with vehicle. The mouse body weight curves are shown.

FIG. 33 shows the X-ray powder diffractometer (XRPD) pattern of FL118 Active Pharmaceutical ingredient (API). The FL118 XRPC pattern indicated that FL118 has a crystal status.

FIG. 34 shows the Differential Scanning Calorimetry (DSC) curve of FL118 API. The FL118 DSC curve indicated that FL118 has no melting point.

FIG. 35 shows the X-ray powder diffractometer (XRPD) overlay of the HPβCD-FL118 complex powder product. The XRPD results indicate that HPβCD-FL118 complex powder products are all amorphous. Of note, the FL118 API batch used is FR00535-01-190708

FIG. 36 shows the Modulated Differential Scanning Calorimetry (mDSC) profile of the HPβCD-FL118 complex powder product at the Condition 1. Of note, the FL118 API batch used at Condition 1 is FR00535-01-190708

FIG. 37 shows the Modulated Differential Scanning Calorimetry (mDSC) profile of the HPβCD-FL118 complex powder product at Condition 2. Of note, the FL118 API batch used at Condition 1 is FR00535-01-190708.

FIG. 38 shows the Modulated Differential Scanning Calorimetry (mDSC) profile of the HPβCD-FL118 complex powder product at Condition 3. Of note, the FL118 API batch used at Condition 1 is FR00535-01-190708

FIG. 39 shows the Modulated Differential Scanning Calorimetry (mDSC) profile of the HPβCD excipient for comparison.

FIG. 40 shows the X-ray powder diffractometer (XRPD) overlay of HPβCD-FL118 complex (FR00535-02-190904-01). The FL118 XRPC pattern indicated that HPβCD-FL118 complex powder product is amorphous.

FIG. 41 shows the Modulated Differential Scanning Calorimetry (mDSC) profile of the HPβCD-FL118 complex powder product (FR00535-02-190904-01). The mDSC results indicate that there is no glass transition temperature for HPβCD-FL118 complex product.

FIG. 42 shows the X-ray powder diffractometer (XRPD) overlay of the 10-day stability at two conditions. The XRPD results indicate that the HP-β-CD-FL118 complex samples are very stable in both conditions.

FIG. 43 shows the High Performance Liquid Chromatography (HPLC) overlay of the 10-day stability at two conditions. The HPLC results indicate that the HP-β-CD-FL118 complex samples are very stable in both conditions.

FIG. 44 shows the X-ray powder diffractometer (XRPD) overlay of the HP-β-CD-FL118 complex. The XRPD results indicate that HPβCD-FL118 complex is amorphous. Of note, the FL118 API batch used is FR00535-01-190708

Figure 10:
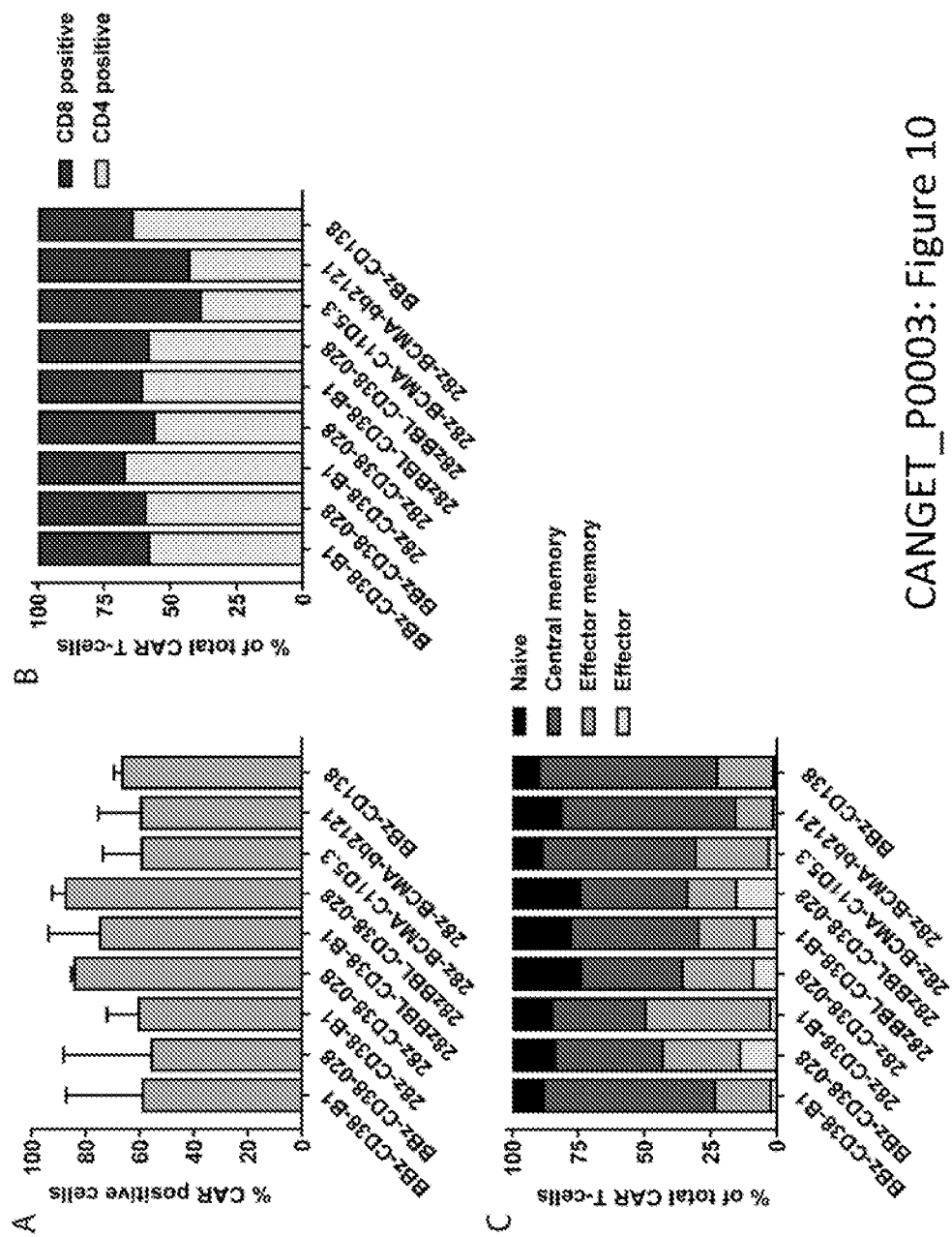

Table 1: Overview of CAR constructs. Overview of CAR constructs containing a CD8a transmembrane domain, a CD3 ζ intracellular signaling domain and co-stimulatory domains 4-1 BB, CD28, or CD28 plus a separately-expressed full length 4-1 BB ligand (4-1BBL). The different scFv sequences enables recognition of MM-specific antigens CD138, BCMA, or CD38. The CAR sequences were linked to a truncated LNGRF (CD271), dsRED, or 4-1BBL sequence, that after retroviral transduction, enables detection of CAR expression on the T-cells. The transduction efficiency, as well as CD4/CD8 ratio's and phenotypic profile of the CAR T-cells are depicted in FIG. 10.

Table 2: Spray drying parameters for HP-β-CD-FL118 complex preparation.

Table 3: Characterization for HPβCD-FL118 complex prepared through spray drying.

Table 4: Spray drying parameters for HPβCD-FL118 complex preparation at 2 g scale.

Table 5: Characterization for HP-β-CD-FL118 complex prepared via spray drying.

Table 6: HP-β-CD-FL118 complex 10 days stability study design.

Table 7: HP-β-CD-FL118 complex 10 days stability test results.

Table 8: Relative Retention Time (RRT) results of 10 days stability at two conditions.

Table 9: Results of HPβCD-FL118 complex (Batch No.: FR00535-02-190904-01) dissolution test in two mediums.

Table 10: A modified process development for HPβCD-FL118 complex preparation.

Table 11: Spray drying parameters for HP-β-CD-FL118 complex preparation at 10 g scale.

Table 12: Characterization for the scale-up HPβCD-FL118 complex prepared via spray drying at the 10-gram level of the FL118 API.

DETAILED DESCRIPTION OF THE DISCLOSURE

Figure 1:
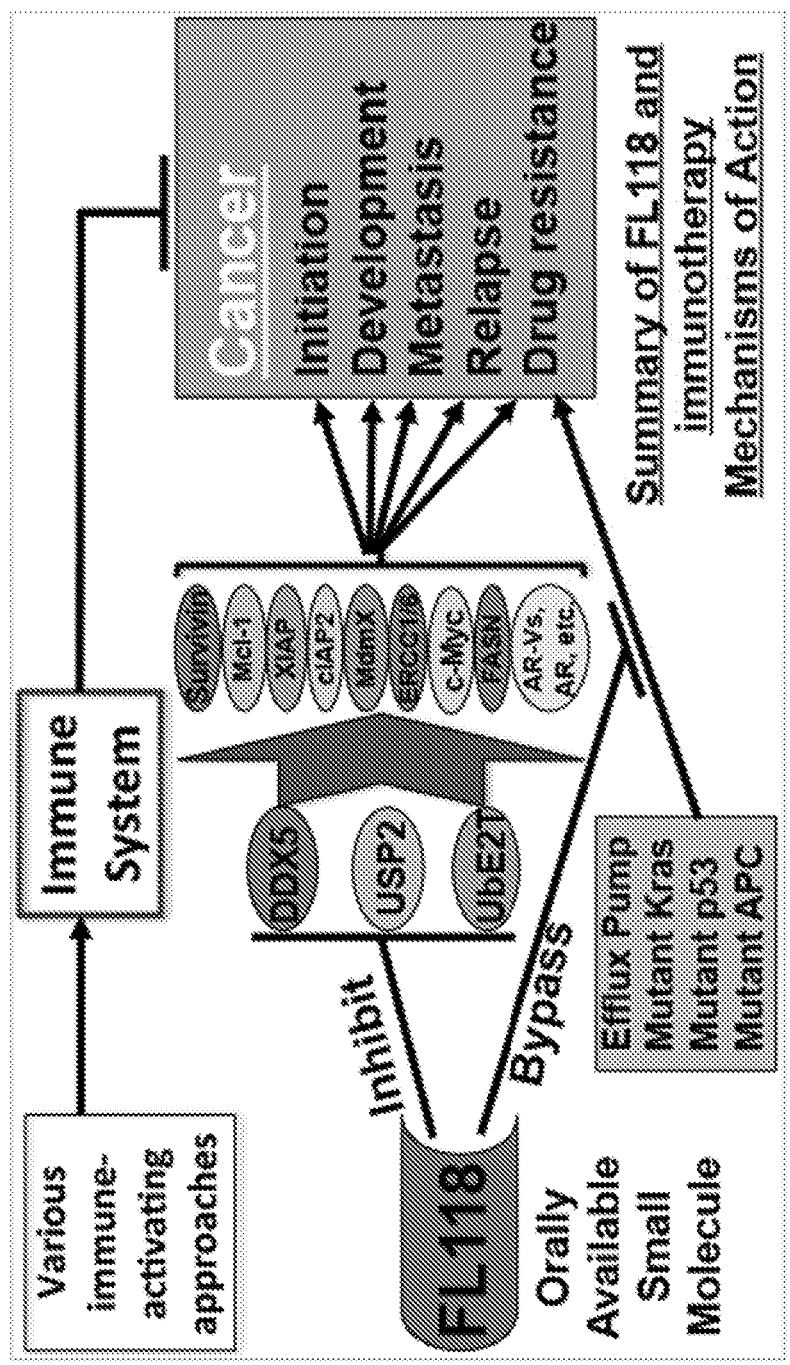

The present disclosure relates to the newly discovered formulation of FL118 as well as the use of FL118 for combination treatment with a type of immunotherapy for human cancer treatment (FIG. 1). Likewise, methods for the newly invented formulation of FL118 as well as the FL118-immunotherapy combination in the treatment of human cancers are disclosed herein. The present disclosure further relates to the novel pharmaceutical formulation composition and process of FL118 for its use alone or in combination with a type of immunotherapies.

The definitions of certain terms as used in this specification are provided below. Unless defined otherwise, all technical and scientific terms used herein generally have the same meaning as commonly understood by one of ordinary skill in the art to which this disclosure belongs. As used in this specification and the appended claims, the singular forms "a", "an" and "the" include plural referents unless the content clearly dictates otherwise. For example, reference to "a type", "a class" includes a combination of two or more types, classes and the like.

Terminology

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the "administration" of an agent or drug, e.g., one or more antiapoptotic protein and/or signaling inhibitor compounds, to a subject or subjects includes any route of introducing or delivering to a subject a compound to perform its intended function. Administration can be carried out by any suitable route, including orally, intranasally, by inhalation, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment/prevention, and wherein some biologically or medically relevant result is achieved.

As used herein, the terms "assessing," "assaying," "determining," and "measuring" are used interchangeably and include both quantitative and qualitative determinations. These terms refer to any form of measurement, and include determining if a characteristic, trait, or feature is present or not. Assessing may be relative or absolute. "Assessing the presence of" includes determining the amount of something present and/or absent.

As used herein, the term "clinical factors" refers to any data that a medical practitioner may consider hi determining a diagnosis, prognosis, or therapeutic regimen for treating or preventing a disease or diseases. Such factors include, but are not limited to, the patient's medical history, a physical examination of the patient, complete blood count, examination of blood cells or bone marrow cells, cytogenetics, pulmonary health, vascular indications of disease, and immunophenotyping of cells.

As used herein, the terms "comparable" or "corresponding" in the context of comparing two or more samples, responses to treatment, or drugs, refer to the same type of sample, response, treatment, and drug respectively used in the comparison. In some embodiments, comparable samples may be obtained from the same individual at different times. In other embodiments, comparable samples may be obtained from different individuals, e.g., a patient and a healthy individual. In general, comparable samples are normalized by a common factor for control purposes.

As used herein, the term "composition" refers to a product with specified ingredients in the specified amounts, as well as any product which results, directly or indirectly, from combination of the specified ingredients in the specified amounts.

As used herein, the term "diagnosis" means detecting a disease or disorder or determining the stage or degree of a disease or disorder. Typically, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease, i.e., there may be differential diagnoses that can be inferred from a diagnostic factor or symptom. Likewise, there may be instances where a factor or symptom that is indicative of a particular disease is present in an individual that does not have the particular disease. The term "diagnosis" also encompasses determining the therapeutic effect of a drug therapy, or predicting the pattern of response to a drug therapy. The diagnostic methods may be used independently, or in combination with other diagnosing and/or staging methods known in the medical art for a particular disease or disorder.

As used herein, the teens "drug," "compound," "active agent," "agent," "actives," "pharmaceutical composition," "pharmaceutical formulation," and "pharmacologically active agent" are used interchangeably and refer to any chemical compound, complex or composition, charged or uncharged, that is suitable for administration and that has a beneficial biological effect, suitably a therapeutic effect in the treatment of a disease or abnormal physiological condition, although the effect may also be prophylactic in nature. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent," and "API" (active pharmaceutical ingredient) are used, then, or when a particular active agent is specifically identified, it is to be understood that applicants intend to include the active agent per se as well as pharmaceutically acceptable, pharmacologically active salts, esters, amides, prodrugs, conjugates, metabolites, analogs, etc.

As used herein, the terms "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition of the disclosure administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present disclosure can also be administered in combination with one or more additional therapeutic compounds.

As used herein, the term "neoplastic disease" refers to cancers of any kind and origin and precursor stages thereof. Accordingly, the term "neoplastic disease" includes the subject matter identified by the terms "neoplasia". "neoplasm", "cancer", "pre-cancer" or "tumor." A neoplastic disease is generally manifest by abnormal cell division resulting in an abnormal level of a particular cell population. Likewise, the monoclonal expansion of endothelial cells may refer to a "neoplasm" of the pulmonary arteriolar endothelial cells. The abnormal cell division underlying a neoplastic disease, moreover, is typically inherent in the cells and not a normal physiological response to infection or inflammation. In some embodiments, neoplastic diseases for diagnosis using methods provided herein include carcinoma. By "carcinoma," it is meant a benign or malignant epithelial tumor.

As used herein, the term "pharmaceutically acceptable salt" includes a salt with an inorganic base, organic base, inorganic acid, organic acid, or basic or acidic amino acid. As salts of inorganic bases, the disclosure includes, for example, alkali metals such as sodium or potassium; alkaline earth metals such as calcium and magnesium or aluminum; and ammonia. As salts of organic bases, the disclosure includes, for example, trimethylamine, triethylamine, picoline, ethanolamine, diethanolamine, and triethanolamine. As salts of inorganic acids, the instant disclosure includes, for example, hydrochloric acid, hydroboric acid, nitric acid, sulfuric acid, and phosphoric acid. As salts of organic acids, the instant disclosure includes, for example, formic acid, acetic acid, trifluoroacetic acid, fumaric acid, oxalic acid, tartaric acid, maleic acid, lactic acid, citric acid, succinic acid, malic acid, methanesulfonic acid, benzenesulfonic acid, and p-toluenesulfonic acid. As salts of basic amino acids, the instant disclosure includes, for example, arginine, lysine and ornithine. Acidic amino acids include, for example, aspartic acid and glutamic acid.

As used herein, the term "prognosis" refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

As used herein, the term "reference level" refers to a level of a substance which may be of interest for comparative purposes. In some embodiments, a reference level may be a specified composition dosage as an average of the dose level from samples taken from a control subject. In other embodiments, the reference level may be the level in the same subject at a different time, e.g., a time course of administering the composition, such as the level determined at 2, 4, 6, 8, and 10 minutes (min), etc.

As used herein, the terms "sample" or "test sample" refer to any liquid or solid material containing collected from a subject. In suitable embodiments, a test sample is obtained from a biological source, i.e., a "biological sample," such as cells in culture or a tissue sample from an animal, most preferably, a murine subject, mammal or human subject.

As used herein, the terms "subject" or "individual," refer to a mammal, such as a mouse, rat, or human, but can also be another animal such as a domestic animal, e.g., a dog, cat, or the like, a farm animal, e.g., a cow, a sheep, a pig, a horse, or the like, or a laboratory animal, e.g., a monkey, a rat, a mouse, a rabbit, a guinea pig, or the like. The term "patient" refers to a "subject" who is, or is suspected to be, afflicted with a disease.

As used herein, the teens "treating" or "treatment" or "alleviation" refer to both therapeutic treatment and prophylactic or preventative measures, wherein the objective is to prevent or slow down (lessen) the targeted pathologic condition or disorder. A subject is successfully "treated" for a disorder if, after receiving a therapeutic agent according to the methods of the present disclosure, the subject shows observable and/or measurable reduction in or absence of one or more signs and symptoms of a particular disease or condition.

Overview

Control of human disease such as neoplastic disease or cancer to extend life span and increase quality of life is the goal in clinical practice. In the field of human cancer control, the challenge is the treatment (e.g., chemotherapy and radiation) resistance, which results in un-curable disease or a high rate of metastasis and/or recurrence after treatment. Therefore, cancer treatment resistance, metastasis and recurrence are the primary causes of cancer death and continue to challenge the entire field.

Critical analysis of the peer-reviewed literature indicates that the challenge for overcoming treatment resistance is that the inherent or acquired (induced) resistance to treatment is through diverse mechanisms, often resulting from the fact that cancer cells usually possess diverse genetic and epigenetic alternations and abnormal expression of cancer-associated proteins. To address the challenge in treatment resistance, the treatment resistance resulted from diverse mechanisms must be addressed. The prior art is devoid of efficacious strategies to this end.

Using one molecularly targeted agent in concert with one or more traditional cytotoxic drugs as a combination regimen has been previously employed. This approach is able to alleviate the treatment resistance related to efficacy for some of cancer patients with particular cancer types and/or favorable genetic background. A significant increase of toxicity to cancer patients due to the combinational use of multiple drugs at the same time in one regimen could be an area for improvement for the use of this strategy. Another opportunity to overcome treatment resistance is that cancer is a highly heterogeneous disease (Swanton C: Intratumor heterogeneity: evolution through space and time, Cancer research 2012, 72:4875-4882); gene-expression signatures of favorable versus unfavorable prognosis can be detected in different regions of the same tumor, and a significant percentage of somatic mutations may not be detected across every tumor region of the same tumor (Gerlinger M, et al.: Intratumor heterogeneity and branched evolution revealed by multiregion sequencing, The New England journal of medicine 2012, 366:883-892). This extensive intra-tumor heterogeneity presents difficult challenges with respect to personalized cancer treatment (personalized medicine) and biomarker development. Finally, the tumor microenvironment can create a protective niche that facilitates tumor proliferation, survival, and therapy resistance (Meads M B et al. Environment-mediated drug resistance: a major contributor to minimal residual disease. Nat Rev Cancer. 2009, 9:665-674; de Haart S J et al. Accessory cells of the microenvironment protect multiple myeloma from T-cell cytotoxicity through cell adhesion-mediated immune resistance. Clin Cancer Res. 2013, 19:5591-5601). Therefore, new strategies to resolve such challenges are needed.

One aspect of the present disclosure involves the use of our newly invested composition and process of FL118 in a specialized formulation, which control multiple cancer-associated protein targets alone or in combination with a type of immunotherapy demonstrated in examples, to combat cancer cell treatment resistance. Among the novel combination treatment, while FL118 can target or bypass multiple resistant factors (FIG. 1), immunotherapy uses completely different mechanisms of action to combat caner. Thus, a particular cancer type such as multiple myeloma (MM) could be effectively managed. In turn, this imparts novel strategies of personalized precision medicine to resolve the treatment resistance challenge based on patients' overall genetic background. For these patients a particular immunotherapy used would be based on cancer types and certain types of biomarker or genetic determinations. This FL118-associated novel strategy to overcome treatment resistance at a manner of personalized precision medicine comes out of our unexpected results summarized in the BACKGROUND section earlier.

In the present disclosure, we have described the immunotherapies alone and in combination with FL118 for treatment of human cancer to show high anticancer efficacy with acceptable toxicity by using the MM cancer in examples. In this disclosure, we have also described the newly discovered, improved and expanded formulation of anticancer drug using FL118 as an example. We have described in various embodiments of the new formulation composition and process with unique organic solvent-containing strategies as well as the organic solvent-free formulation of the FL118-HP-β-CD complex into aqueous suspension format for intraperitoneal, intravenous or oral administration, powder capsule format or tablet format for oral administration.

Pharmaceutical Compositions

Pharmaceutical compositions were covered by the previous disclosure (PCT/US15/22095). Here, we added the newly discovered and expanded disclosures.

The excipients used to formulate FL118 can be any type of cyclodextrin (CD) including -β-cyclodextrin (-β-CD), hydroxypropyl-β-cyclodextrin (HP-β-CD), sulfobutylether-β-cyclodextrin (SBE-β-CD) or another type of cyclodextrin derivatives.

In one recipe, methanol-HP-β-CD-FL118 complex or ethanol-HP-β-CD-FL118 complex suspension goes through spray-dry process or lyophilization process to remove methanol or ethanol to product a HP-β-CD-FL118 complex powder format.

In another recipe, formic acid-(FA)-HP-β-CD-FL118 complex suspension, acetic acid (AcetA)-HP-β-CD-FL118 complex suspension, zinc acetate-(ZA)-HP-β-CD-FL118 complex suspension or glyoxal-HP-β-CD-FL118 complex suspension goes through spray-dry process or lyophilization process to remove these organic solvents to product a HP-β-CD-FL118 complex powder format.

In the third aspect, the ethylene glycol (EG)-HP-β-CD-FL118 complex suspension, propylene glycol (PG)-HP-β-CD-FL118 complex suspension, formamide-(FAD)-HP-β-CD-FL118 complex suspension, (N,N,N',N')-tetramethylethylenediamine (TEMED)-HP-β-CD-FL118 complex suspension, ethanolamide (EA)-HP-β-CD-FL118 complex suspension or 2-mercaptoethanol (MercE)-HP-β-CD-FL118 complex suspension goes through a lyophilization process or any other method to remove as many as possible organic solvents to product a HP-β-CD-FL118 complex solid format.

In the next aspect, HP-β-CD-FL118 complex powder/solid format is directly diluted with saline containing 0-5% propylene glycol (PG) and 0-5% polyethylene glycol 400 or 300 (PEG400 or PEG300). In most cases, the HP-β-CD-FL118 complex powder format is directly diluted with saline containing 2.5% PG and 2.5% PEG400 to become an aqueous suspension for administration.

In the next aspect, the suspension of FL118 for combination with a type of immunotherapy contains organic solvent-free HP-β-CD-FL118 complex suspension diluted in saline containing 2.5% PG and 2.5% PEG400 to become an aqueous suspension before oral administration.

In the next aspect, the HP-β-CD-FL118 complex powder may form tablet format, which includes the pharmaceutical composition of fillers/binders/diluents (e.g. cellulose's/cellulose derivatives, starches/starch derivatives, lactose), disintegrant (e.g. colloidal silicone dioxide, croscarmellose sodium, crosspovidone), glidant (e.g. dibasic calcium phosphate, colloidal silicone dioxide), lubricants (e.g. magnesium stearate, stearic acid, polyethylene glycol, Talc), antimicrobials/preservative (propylene glycol, propylene paraben, methyl paraben, glycerin), etc., according to our techniques plus other well known in the art of pharmaceutical formulation. For example, see, Remington: The Science and Practice of Pharmacy, 21st Ed, Lippincott Williams & Wilkins (2005).

The HP-β-CD-FL118 complex powder can be further formulated with microcrystalline cellulose (MCC, 30%-80%), corn starch (0%-40%), lactose (10%-25%), colloidal silicone dioxide (0%-3%), dibasic calcium phosphate (1%-10%), magnesium stearate (0.2%-3%) for making FL118 tablet.

Pharmaceutical compositions are typically formulated to be compatible with its intended route of administration. The composition format product described above can be accordingly administered orally, intraperitoneally or intravenously.

The pharmaceutical composition and method of the present disclosure for FL118 will be used alone or in combination treatment with a type of immunotherapy for treatment of cancer.

Methods and Uses

The present disclosure is further illustrated by many examples presented below, which should not be construed as limiting in any way. The following is a description of the materials and methods used throughout the examples.

Bone marrow mononuclear cells (BMMNCs): BMMNCs from MM patient bone marrow (BM) aspirates were isolated by Ficoll-Hypaque density-gradient centrifugation and cryopreserved in liquid nitrogen until use. All patient material and clinical data used in this project has been collected according to the code of conduct for medical research developed by The Council of the Federation of Medical Scientific Societies (FEDERA (https://www.federa.org/codes-conduct).

Bone Marrow derived Mesenchymal stromal cells (BMMSCs): Diagnostic BM aspirations from MM patients were used to isolate BMMNCs and culture adherent BMMSCs as described elsewhere (Prins H J, et al. *Tissue Eng Part A*. 2009, 15:3741-3751). To minimalize inter-individual variation, all experiments were performed with cells from a pool of BMMSCs derived from twelve MM patients at passage 3.

Cell lines and culture: Luciferase (LUC)-transduced MM cell lines RPMI 8226, JJN3, UM9, MM1.s, U266, L363, and OPM-2 were cultured in RPMI 1640 (Life Technologies), supplemented with 10% heat-inactivated HyClone FetalClone I serum (GE Healthcare Life Sciences) and (penicillin, 10.000 U/mL; streptomycin, 10.0001 µg/mL; InVitrogen,). HS-5 was cultured in DMEM (Life Technologies), supplemented with heat-inactivated FBS (Sigma) and antibiotics.

CTL clone: The HLA-DP4 restricted, minor histocompatibility antigen (mHag)-specific CD4+ cytotoxic T lymphocyte (CTL) clone 3AB11 was previously described in detail with respect to the antigen-specific and HLA-restricted cytotoxic capacity against the relevant HLA-matched and antigen-positive MM cells (Holloway P A et al. Br J Haematol. 2005; 128:73-81; Spaapen R et al. Clin Cancer Res. 2007; 13:4009-15). CTLs were expanded using a feeder cell-cytokine mixture and cryopreserved until further use (Spaapen R et al. Clin Cancer Res. 2007; 13:4009-15).

Reagents: For in vitro use, FL118 was dissolved in dimethyl sulfoxide (DMSO) at a concentration of 1 mmol/L, aliquoted, and stored as stock solution at −20° C. The intravenous formulation of FL118 for in vivo use. Briefly, the formulation of FL118 in this study used the basic formulation recipe containing FL118 (0.05-0.1 mg/ml), DMSO (0.5-1%), and hydroxypropyl-b-cyclodextrin (0.05-0.1%, w/v) in saline. The corresponding vehicle solution contained DMSO (0.5-1%) and hydroxypropyl-b-cyclodextrin (0.05-0.1%, w/v) in saline without FL118. Doxorubicin hydrochloride (Pharmacia & Upjohn) was dissolved in DMSO at a concentration of 10 mmol/L and stored at 4° C. Bortezomib (Selleckchem) and melphalan (Aspen Pharma Trading Limited) were dissolved in DMSO at concentrations of 5 mmol/L and 16382.7 µmol/L respectively, aliquoted and stored at −80° C. and −20° C. respectively. Dexamethasone (Hospital Pharmacy, 4 mg/mL) was dissolved in PBS at 100 µmol/L and stored at −20° C. Lenalidomide (Celgene) and pomalidomide (Selleckchem) were dissolved in DMSO at concentrations of 10 mmol/L and 50 mmol/L respectively and stored at −80° C. Anti-DR5 antibody Drozitumab was purchased at Absolute Antibody.

Bioluminescence imaging (BLI)-based cytotoxicity assays using luciferase (LUC)-transduced MM cell lines: BMMSCs or HS-5 stromal cell line were plated in white opaque, 96-well flat-bottom plates at $2 \times 10^4$ cells/well. After 24 hours, LUC-transduced MM cell lines were added and co-cultured for 24 or 48 hours before start of treatment. Immunotherapy included 24-hour incubation with FL118 and/or immunotherapy or drugs. T cell therapy included 3AB11 CTLs or CAR T cells at indicated Effector to Target (E:T) ratio's. Targeted antibody therapy included daratumumab, anti-DR5 Drozitumab, or control antibody, and were supplemented with freshly isolated PBMCs from healthy donors at an E:T ratio of 40:1. Therapy with drugs included incubation with FL118 and/or doxorubicin, bortezomib, melphalan, dexamethasone (48 hours), or pomalidomide (72 hours). The survival of MM cells after treatment was determined by BLI 30 minutes after addition of the substrate beetle luciferin (125 µg/ml; Promega). Percent lysis of MM cells by specific treatments was determined using the following formula: % lysis=1−BLI signal in treated wells/mean BLI signal in untreated wells×100%.

Flow cytometry-based cc vivo assays using BMMNCs: Cryopreserved BMMNCs derived from MM patients were incubated on a monolayer of $2 \times 10^4$ BMMSCs for 16 till 24 hours and subsequently treated with FL118 (100 mmol/L) and/or, melphalan (5-10 µM/L), bortezomib (2-3 nmol/L) for 48 hours. Concerning immunotherapy, treatment included FL118 (10 or 100 nM) and/or daratumumab, or CAR T-cells for 24 hours. BMMNC samples contained sufficient numbers of functional effector cells to induce antibody-mediated plasma cell lysis. At the end of treatment, after addition of flow-count fluorospheres (Beckman Coulter), adherent cells were detached with Accutase, blocked with human immunoglobulin (100 µg/mL, Sanquin), and stained for CD38, CD138, CD45 (Beckman Coulter) and live/dead cell marker (LIVE/DEAD Fixable Near-111; Life Technologies) to determine absolute numbers of viable MM cells using flow cytometry. The percentage lysis was then calculated using the following formula: % lysis cells=1−absolute number of viable CD138$^+$ CD38$^+$ CD45$^{dim}$ MM cells in treated wells/mean absolute number of viable CD138$^+$ CD38$^+$ CD45$^{dim}$ MM cells in untreated wells×100%.

Western blotting: Untreated or FL118 treated (16 h) MM cell lines were washed twice with ice-cold PBS. Cell pellets were then snap-frozen and stored at −80° C. until further use. Pellets were dissolved in Radioimmunoprecipitation (RIPA) lysis buffer, supplemented with protease inhibitor cocktail (Roche) and incubated on ice for 45 minutes. Lysates were centrifuged at 14000 g for 10 minutes at 4° C. and supernatant was collected. Protein concentrations were determined by a DC protein assays (Bio-Rad). Samples were separated on 4-20% Mini-protean TGX precast gels (Bio-Rad) and proteins were transferred to Immobilon-FL PVDF membrane (Merck Millipore). After 1 h blocking with Odyssey Block Buffer (LI-COR) at room temperature, membranes were incubated with primary antibodies over night at 4° C. (anti-Mcl-1, anti-survivin Santa Cruz; anti-XIAP, anti-Bcl-2, anti-PUMA, anti-p21 Waf/Cip1, anti-PARP, anti-caspase-3 Cell Signaling Technology; anti-p53 DAKO; anti-NOXA, anti-Actin Merck Millipore). Blots were visualized by Odyssey infrared imaging (LICOR Biosciences) using IRDye 680 Goat-anti-Rabbit (LI-COR Lincoln) and IRDye 800CW Goat-anti-Mouse IgG (LI-COR Lincoln) according to manufacturer's instructions. Band intensities were quantified using Odyssey software.

CD138-, BCMA- and CD38-specific CAR T-cells: All CAR T-cells with different specificities were generated with co-stimulatory domains 4-1BB, CD28, or CD28 supplemented with a separate 4-1BB ligand (28zBBL), with the technology as described previously (Kim J H, et al. *PLoS One*. 2011, 6:e18556; Drent E, et al. *Clin Cancer Res*. 2019, 25:4014-4025). CD138 CAR T-cells (nBT) were produced using single chain variable fragment (scFv) sequences of the published nBT062 monoclonal antibody (Ikeda H, et al. *Clin Cancer Res*. 2009, 15:4028-4037). BCMA CAR T-cells were produced using published scFv sequences derived from C11D5.3 monoclonal antibody (US2012/0082661 A1 (Shancer Z, et al. *Antib Ther.* 2018, 1:19-25) or from BCMA02 CAR (product name bb2121, WO 2016/094304 A2) (Raje N, et al. *N Engl J Med*. 2019, 380:1726-1737; Friedman K M, et al. *Hum Gene Ther.* 2018, 29:585-601). The generation and functional analysis of CD38 CAR T-cells with low (B1) or high (028) CD38-affinities has been described previously (Drent E, et al. *Clin Cancer Res*. 2019, 25:4014-4025; Drent E, et al. *Mol Ther.* 2017, 25:1946-1958). More detailed information on all CAR construct are listed in Table 1. CAR T-cells were tested 10-14 days after CAR transduction or frozen until testing. After thawing, CAR T-cells were cultured for 16 hours in 60 U/mL recombinant human IL-2 (R&D Systems)-containing culture medium (RPMI 1640 supplemented with heat-inactivated FBS (Sigma) and antibiotics), before using in experiments. Flow cytometry analysis, to determine the transduction efficiency and phenotypic profile of each CAR T-cell, was performed as previously described (Drent E, et al. *Clin Cancer Res*. 2019, 25:4014 4025; Drent E, et al. *Mol Ther.* 2017, 25:1946-1958) and illustrated in FIG. 10.

MM-reactive CTL 3AB11: The 3AB11 is an HLA-DP4 restricted, minor histocompatibility antigen (mHag)-specific CD4$^+$ cytotoxic T lymphocyte (CTL), that has been previously described in detail (Holloway PA, et al. *Br J Haematol*. 2005, 128:73-81; Spaapen R, et al. *Clin Cancer Res*. 2007, 13:4009-4015) and was earlier used to demonstrate BM-ME-mediated immune resistance (de Haart S J, et al. *Clin Cancer Res*. 2013, 19:5591-5601). 3AB11 was expanded using a feeder cell-cytokine mixture and cryopreserved until further use as described previously (Spaapen R, et al. *Clin Cancer Res*. 2007, 13:4009-4015).

Intracellular staining Survivin and Mcl-1: Mcl-1 and survivin expression levels in MM cells of BMMNC patient samples were determined by intracellular staining followed by flow cytometry. Untreated or FL118 treated (16 h) patient samples were washed twice with cold PBS. Cells were blocked with human immunoglobulin and stained for CD38 (BD biosciences), CD138 (Bio-Connect) and live/dead cell marker. In addition, LUC- and Green fluorescence protein (GFP)-transduced UM9 MM-cells were incubated alone or a monolayer of $1 \times 10^6$ BMMSCs in a 100 mm dish for 24 or 48 hours. Non-adherent cells were harvested by taking culture medium from plates and washing plates with PBS by gentle pipetting. Adherent cells were harvested using StemPro Accutase. Both adherent and non-adherent cells were blocked with human immunoglobulin and stained for CD105 (Synobiotechnology) and live/dead marker. The stained patient cells and UM9 cells were then fixated in 4% formaldehyde for 15 minutes at room temperature. After fixation, the cells were placed in ice cold 90% methanol for 30 minutes on ice for permeabilization and subsequently stored at −20° C. For intracellular staining, the permeabilized cells were again blocked with human immunoglobulin and stained for Survivin and Mcl-1 (Cell Signaling). Expression levels were analyzed in viable CD38$^+$ CD138$^+$ patient MM cells and GFP$^+$ CD105$^-$ UM9-cells using flow cytometry.

In vivo efficacy of FL118: The in vivo efficacy of FL118 was studied in a xenograft RAG2$^{-/-}$γc$^{-/-}$ marine model in which human MM cells are grown in a humanized BM like microenvironment generated by subcutaneous inoculation of MSC coated Hybrid scaffolds (4 scaffolds per mice) as described elsewhere (Groen R W, et al. Blood 2012,120:e9-e16). 24 hours before tumor inoculation (UM9; $5 \times 10^5$ cells/scaffold) mice were pre-conditioned with 18 mg/kg Busilvex. One week after inoculation, when there was visible tumor growth in all scaffolds by BLI, mice were randomly divided in four groups which were treated as follows: (1) vehicle control (n=3); (2) 0.05 mg/kg FL118 (n=4); (3) 0.1 mg/kg FL118 (n=4); (4) 0.2 mg/kg FL118 (n=4). FL118 or vehicle was administrated i.v. daily for five times. Tumor growth was monitored by weekly BLI measurements as previously described (Groen R W, et al. Blood 2012,120:e9-e16). All animal experiments were conducted for animal experimentation and were in compliance with the Dutch Animal Experimentation Act.

Transwell assays: BMMSCs were seeded in 24-well plates at a density of $1 \times 10^5$ cells/well. After 24 hours, $1 \times 10^4$ cells LUC-transduced UM9 cells were placed in 6.5 mm transwells having 0.4 μm pore membrane inserts (Sigma Aldrich). After 24 hours, CAR T-cells were added in the transwell compartment, in which the UM9 cells were present. Percent lysis of UM9 cells by CAR T-cells was determined after 24 hours by BLI, after transferring the cells from the transwell compartment to white opaque, 96-well flat-bottom plates.

IFNγ and granzyme B ELISA: Cell-free supernatants of BLI-based compartment-specific MM cytotoxicity assays were stored at −20° C. The IFNγ and granzyme B contents in thawed supernatants were determined using ELISA kits (eBioscience and Mabtecht for respectively IFNγ and granzyme B) according to manufacturer's protocol.

Toxicity of FL118 on immune effector cells: Cryopreserved BMMNCs derived from MM patients or plasma cell leukemia (PCL) patients, were treated with various concentrations of FL118. After 24 hours, viable CD45$^+$ CD3$^+$ T-cells and CD45$^+$ CD56$^+$ CD14$^-$ CD3$^-$ NK-cells were enumerated by multiparameter flow cytometry. Additionally, healthy-donor peripheral blood mononuclear cells (PBMCs) were seeded in 96-well flat-bottom plates at 1×10$^5$ cells/well, stimulated with PMA (25 ng/mL) and ionomycin (500 ng/mL) (both Santa Cruz Biotechnology) for 24 hours, and subsequently treated with FL118 for 48 hours before determining activated CD45$^+$ CD3$^+$ CD56$^-$ CD25$^+$ T-cells by flow cytometry. The percentage cell survival was then calculated using the following formula: % immune cell survival=absolute number of viable immune cells in treated wells/mean absolute number of viable immune cells in untreated wells×100%.

T cell Proliferation assays: PBMCs from healthy donors were seeded in 96-well flat-bottom plates at 4×10$^4$ cells/well and stimulated with anti-CD3/CD28-coated dynabeads (LifeTechnologies) in a bead-to-cell-ratio of 1:3 and 50 U/mL recombinant human IL-2. After 24 hours, the PBMCs were treated serial dilutions of FL118 or a DMSO control, representing the highest DMSO content, for 24 hours. BrdU was added 16 hours prior to the termination of proliferation. BrdU incorporation was measured by Cell Proliferation ELISA (Sigma Aldrich) according to manufacturer's protocol.

Statistics: Comparisons between variables were performed using two-tailed paired or unpaired Student's t-test or the Mann-Whitney test or the Wilcoxon matched-pairs rank test using Prism software (Graphpad Software Inc., v.7). Comparisons between multiple groups were performed using a nonparametric Kruskal-Wallis test. Where indicated, half maximal lysis (EC50) of CAR T-cells was determined by nonlinear regression of lysis values obtained with increasing E:T ratios. Correlation was computed using two-tailed Pearson correlation coefficients after checking Gaussian distribution. Where indicated, the Chou-Talalay method was used to quantify immunotherapy-FL118 combinatorial effects with Combination Index (CI) values of <1 indicating synergy, of 1 indicating additive effects, and of >1 indicating antagonism (Chou T C. *Pharmacol Rev.* 2006, 58:621-681). When primary MM cells were used as target cells, the value of immunotherapy-FL118 combinatorial effects were estimated with a BLISS model, in which expected lysis values from combinatorial treatments were calculated using the following formula: % expected lysis=(% lysis with immunotherapy+% lysis with FL118)–% lysis with immunotherapy×% lysis with FL118 (Nijhof I S, et al. *Clin Cancer Res.* 2015, 21:2802-2810; van der Veer M S, et al. *Haematologica.* 2011, 96:284-290; Greco W R, et al. *Pharmacol Rev.* 1995, 47:331-385). The null hypothesis of "additive effects" was rejected, if the observed values were significantly different than the expected values. P-values below 0.05 were considered significant.

All in vivo experimental studies were approved by the Institutional Animal Care and Use Committee (IACUC), and performed following the IACUC-approved mouse protocol at Roswell Park Animal Center. Methods in brief: Human SW620 colorectal cancer xenograft tumors were first generated through implanting 2×10$^6$ SW620 cancer cells at the flank area of severe combined immunodeficiency (SCID) mice. After tumor grew to 800-1,200 mm$^3$, the tumors were isolated and individual experimental mice were subcutaneously implanted with 30-50 mg non-necrotic tumor masses at the flank area of individual mice. Seven to 10 days after tumor transplantation at which the implanted SW620 xenograft tumors were grown to 100-200 mm$^3$ (defined as day 0), mice were randomly divided into the required groups for treatment via oral administration of the different organic solvent-hydroxypropyl-β-cyclodextrin (HPβCD)-formulated FL118 or vehicles. The schedule for FL118 or vehicle treatment was weekly for up to 4-times (weekly×4). The orally administered FL118 product resulted from various formulations contains FL118 (0.5 mg/mL), HPβCD (0.5%, w/v), propylene glycol (PG, 2.5%), and polyethylene glycol 400 (PEG400, 2.5%) in saline. The vehicle solution contains HPβCD (0.5%, w/v), PG (2.5%) and PEG400 (2.5% w/v) in saline without FL118. Tumor length (L) and width (W) were measured using digital vernier calipers 3-4 times per week for the first week and then 2 time per week until the end of experiments. The tumor volume (v) was calculated using the formula: v=0.5 (L×W$^2$). Then the tumor size was divided by the day 0 tumor size as percentage tumor size versus day 0. The tumor curves were made using Microsoft Excel.

Analyses of the formulated FL118 product: The FL118 product uses a type of cyclodextrin (CD) as the excipient for the FL118 formulation. The CD includes -β-cyclodextrin (-β-CD), hydroxypropyl-β-cyclodextrin (HP-β-CD), sulfobutylether-β-cyclodextrin (SBE-β-CD) or another type of cyclodextrin derivatives.

Crystal versus amorphous status analyses of FL118 versus the formulated FL118 product using X-ray powder diffractometer: The crystal or amorphous status of each formulated FL118-a type of CD complex powder is determined using X-ray powder diffractometer (XRPD). Specifically, about 5 mg samples of each formulated FL118-a type of CD complex powder are spread onto the center of Si-substrate (samples area will be 1 cm in diameter) for XRPD testing. Laboratory XRPD patterns for samples will be collected at 25° C. The diffraction data will be collected over the angular range of 2θ=3°-40° with a step size of 2θ=0.02° and accounting time of 0.12 s/step.

Analyses of the formulated FL118 product miscibility status using Modulated Differential Scanning Calorimetry: The miscibility status of FL118 with the excipient (a type of CD) in the FL118 product (FL118-a type of CD complex) is determined using Modulated Differential Scanning Calorimetry (mDSC). Specifically, mDSC analyses are carried out on a Q2000 differential scanning calorimeter (TA, USA) at a 2° C./min heating rate over the temperature range from room temperature to 300° C. in a dynamic nitrogen atmosphere. Each FL118-a type of CD complex powder is weighed into a Tzero aluminum sample pan covered by a pinhole lid; an empty pan served as the reference control for testing. Additionally, the glass transition temperature (Tg) of the formulated FL118 product powder is also determined using mDSC.

Analyses of the non formulated FL118 Active Pharmaceutical Ingredient (API) using Differential Scanning Calorimetry: The Differential Scanning Calorimetry (DSC) analyses are similar to mDSC and are carried out on a Q2000 differential scanning calorimeter (TA, USA) at a 10° C./min heating rate over the temperature range from room temperature to 300° C. in a dynamic nitrogen atmosphere. The FL118API sample is weighed into Tzero aluminum sample pan covered by pinhole lid; an empty pan served as the reference for test.

Analyses of the weight percentage of the FL118 Active Pharmaceutical Ingredient (API) in the formulated FL118 product using High Performance Liquid Chromatography: The weight percentage of FL118 API loading in the defined cyclodextrin (CD) is determined using High Performance Liquid Chromatography (HPLC). We use the Waters XSelect CSH C18 column (3.5 µm, 4.6×150 mm, Waters, Ireland) in the testing. The mobile phase is a gradient program of 0.05% aqueous trifluoroacetic acid (Mobile phase A) and acetonitrile with 0.05% trifluoroacetic acid (Mobile phase B), which is pumped at a total flow rate of 1 mL per min. The gradient is as follows: initial conditions 10% B in A, then linear gradient of 10 to 60% B in A over 15 min, then linear gradient of 60 to 90% B in A over 10 min, 90% B in A hold for 5 min, return to initial conditions for 0.01 min and hold for 10 min. The temperature of the column is maintained at 30° C. and the eluent is monitored at a wavelength of 220 nm. The injection volume is 5.0 µL. The diluent is DMSO.

EXAMPLES

The present disclosure is further illustrated by the following examples, which should not be construed as limiting in any way. The following is a description of the examples.

Figure 2:
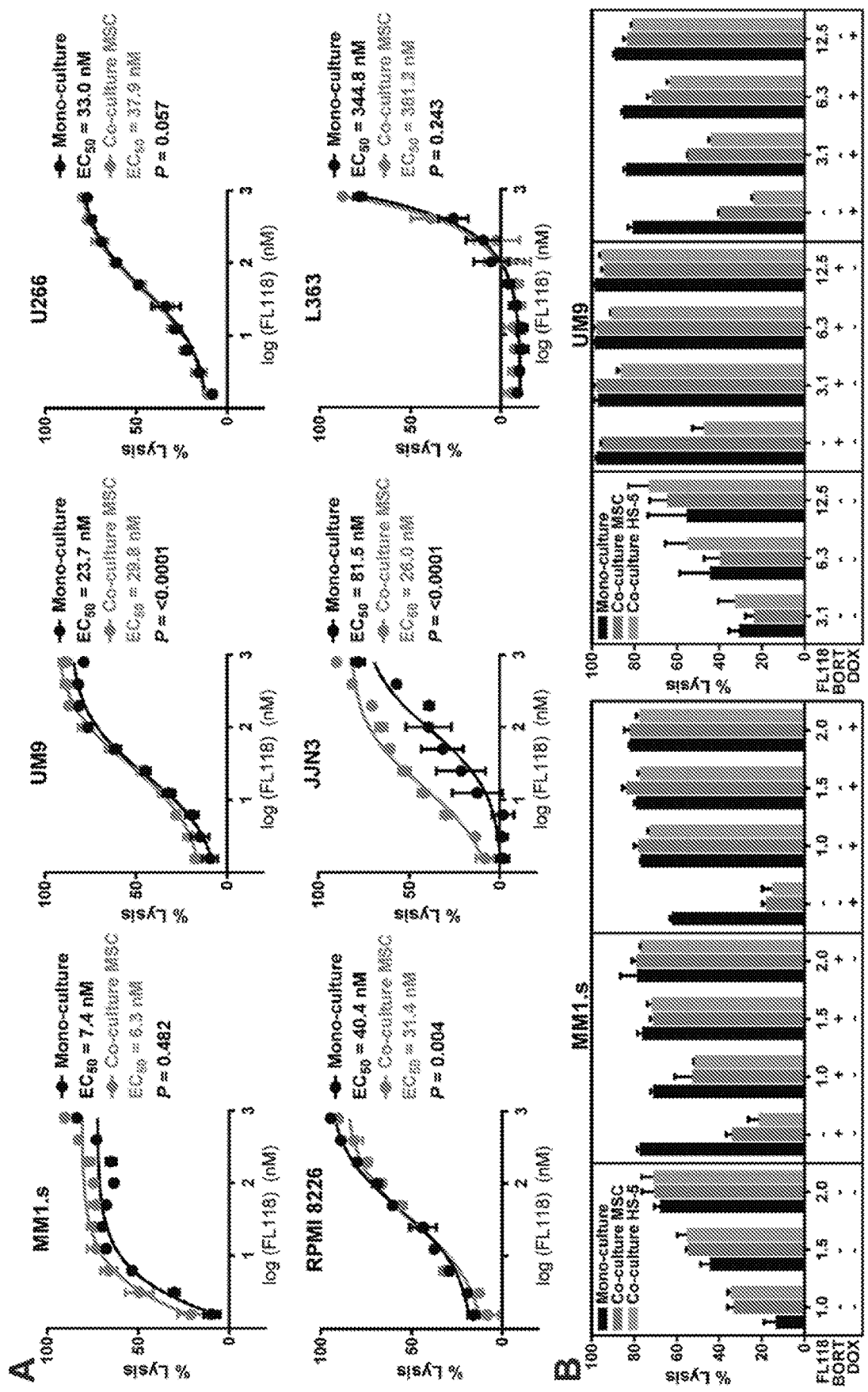
Figure 5:
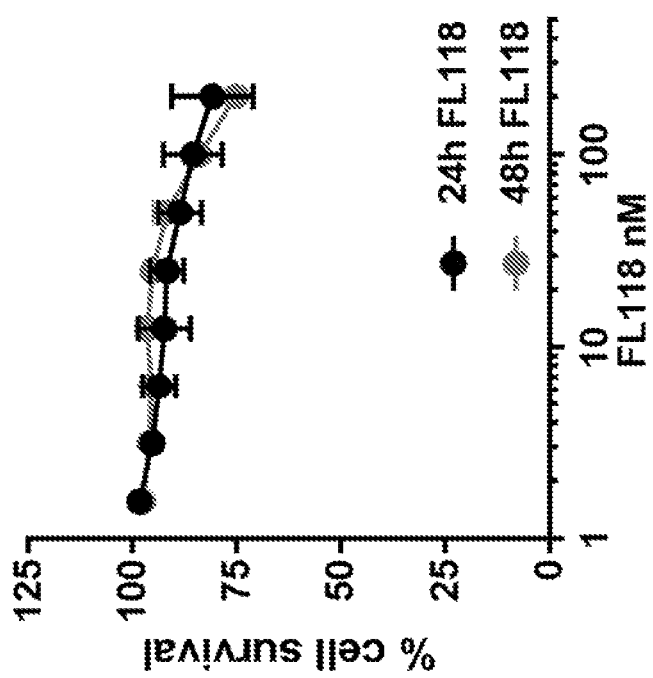
Figure 6:
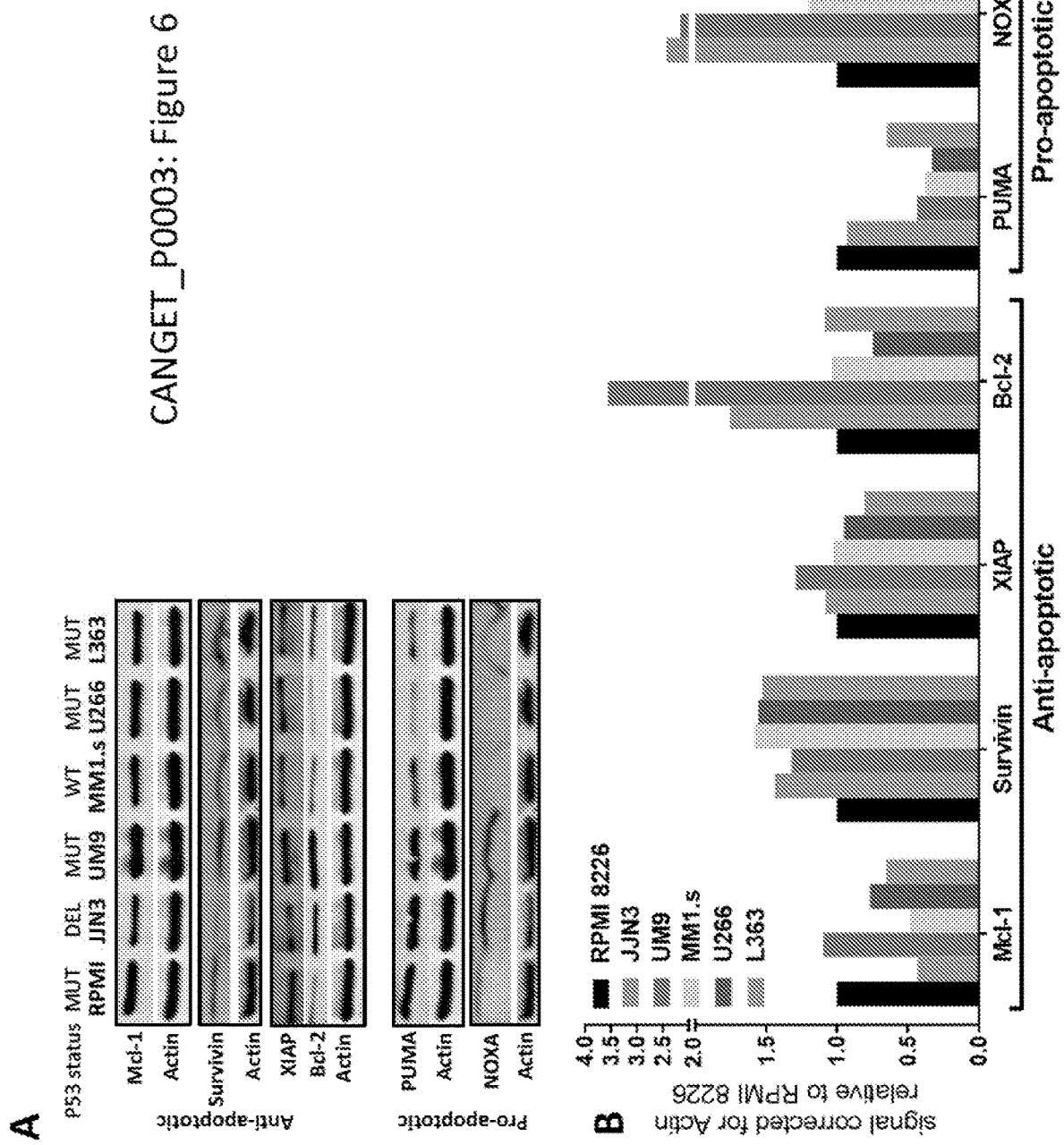
Figure 7:
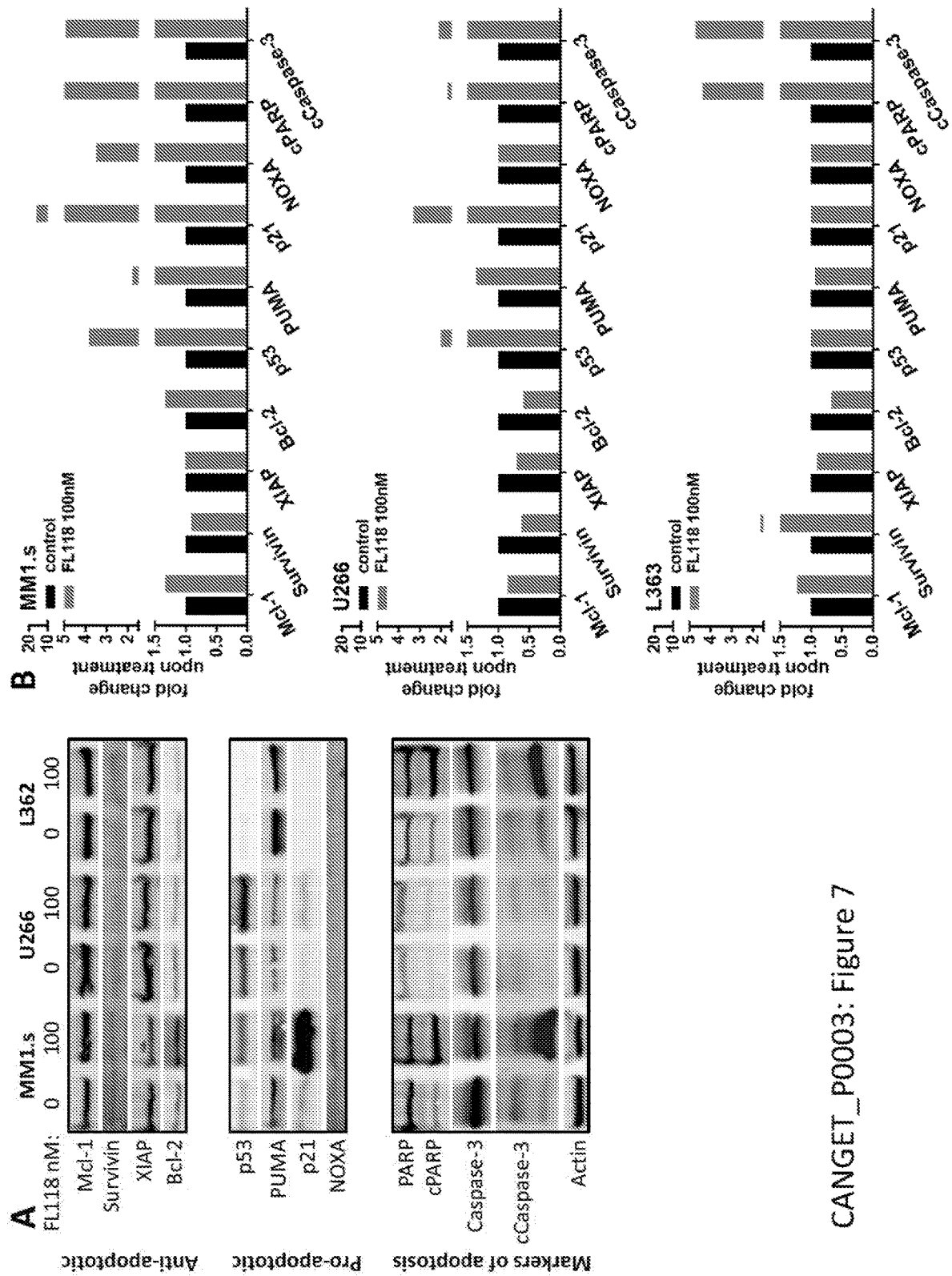

Example 1—High efficacy of FL118 against MM cell lines is not affected by BMMSCs and is achieved by modulation of multiple anti-apoptotic genes: We first evaluated FL118 against a panel of six MM cell lines with different p53 status. Since stromal cells can induce microenvironment-induced drug resistance, the assays were executed in the presence or absence of MM patient-derived bone marrow mesenchymal stromal cells (BMMSCs). While FL118 showed only minimal toxicity against BMMSCs (FIG. 5), it exhibited a clear dose-dependent anti-MM activity in the MM cell lines, independent of the p53 status, with EC50 values ranging from 7.4 nmol/L to 344.8 nmol/L (FIG. 2A). Importantly, lysis of MM cell lines by FL118 was not reduced, or even increased, in the presence of BMMSCs for 5 of 6 MM cell lines, except for a minimal reduction for the cell line UM9. Further analyses indicated that the efficacy of FL118 to induced lysis in MM cell lines was not related to the baseline protein expression levels of its known direct or indirect targets, including Mcl-1, Survivin, XIAP, Bcl-2, PUMA, or NOXA (FIG. 6). Rather, the activity of FL118 seemed to correlate with its capacity to modulate these genes; in three MM cell lines with high, intermediate, and low FL118 susceptibility, respectively, FL118 promoted pro-apoptotic signaling and cleavage of caspase-3 and PARP only in the high- and intermediate-susceptible cell lines but not in the low-susceptible cell line (FIG. 7).

Example 2—FL118 can reverse aroma cell-induced drug resistance: One of the well-described contributors to therapy resistance in MM is microenvironment-induced drug resistance. Crosstalk of MM cells with BMMSCs via physical contacts or soluble factors can result in the upregulation of several anti-apoptotic proteins. Therefore, we determined whether FL118 could modulate the stromal cell-mediated resistance against other anti-MM drugs. Co-culture of two MM cell lines with BMMSCs or, to a larger extent, with the stromal cell line HS-5 significantly inhibited the lysis of MM cell lines by two anti-MM drugs, bortezomib and doxorubicin (FIG. 2B). This stroma-cell induced drug resistance was effectively abrogated by FL118 in a dose-dependent manner (FIG. 2B). These observations, in particular the reversal of stroma-induced bortezomib resistance by FL118 may be relevant because next to other possible resistance mechanisms, such as proteasome subunit mutations or increased expression of proteasome subunits, environment-induced drug resistance also contributes to clinical bortezomib resistance.

Figure 3:
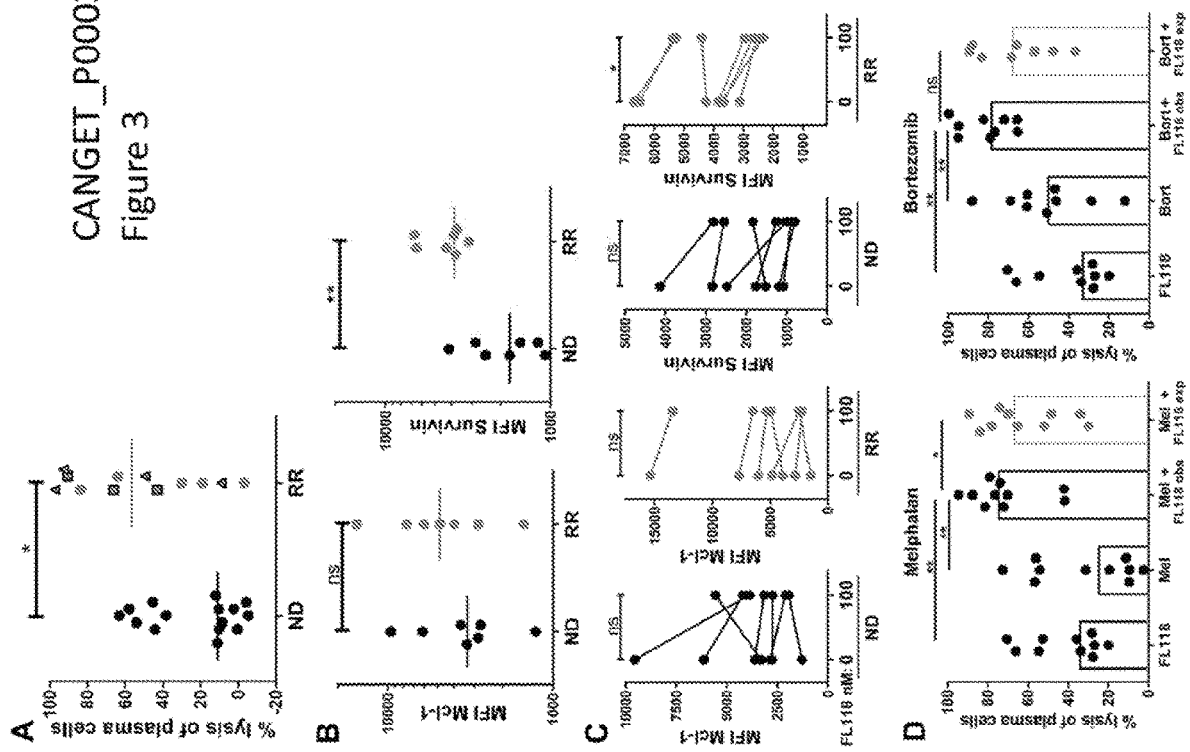

Example 3—FL118 is more effective in relapsed and/or refractory (RR) MM as compared to newly diagnosed MM patients: To evaluate the activity of FL118 in a preclinical setting, we assessed its efficacy against primary MM cells present in bone marrow (BM) mononuclear cell (BMMNC) samples derived from 15 newly-diagnosed (ND) and 12 relapsed and/or refractory (RR) MM patients. In these samples we measured the FL118-induced MM cell lysis by flow cytometry via enumeration of the surviving $CD138^+$ $CD38^+$ MM cells after incubation with FL118 for 24 hours. In 15 of 27 samples, FL118 induced MM cell lysis equal or above 20% (FIG. 3A). Interestingly, FL118 was significantly more effective in the samples of RR patients compared to ND patients. Furthermore, similar to the results obtained with MM cell lines, anti-MM activity of FL118 was independent of the p53 status, since among all good FL118-responders, there were also three patients who showed deletion of chromosome 17p (FIG. 3A). In an attempt to clarify the superior activity of FL118 in RR as compared to ND patients, we measured two FL118 target molecules, Survivin and Mcl-1, in primary MM cells by flow cytometry. Even though RR patients showed enhanced Survivin expression as compared to ND patients, the anti-MM efficacy of FL118 was not associated with the baseline expression of neither Survivin nor Mcl-1 (FIG. 3B). However, in agreement with the results from cell lines, the anti-MM efficacy of FL118 seemed related to its ability to modulate these anti apoptotic proteins, with Survivin modulation being more pronounced in RR patients as compared to ND patients (FIG. 3C). Interestingly, in many FL118-susceptible RR patients, the levels of Survivin expression, although significantly reduced by FL118, were still relatively higher as compared to ND patients. This observation suggests that RR patients became dependent on elevated levels of anti-apoptotic proteins for their survival and may explain why FL118 is more efficient in RR patients than in ND patients. Alternatively, differential expression of efflux pumps could explain the differential efficacy of FL118, but this scenario seems unlikely since recent reports indicate that FL118 is known not to be a substrate for ABCG/CRP and MDR1/P-glycoprotein (P-gp) efflux pumps (Ling, et al. Am J Transl Res. 2015; 7:1765-81, Westover, et al. Mol Cancer. 2015; 14:92).

Figure 8:
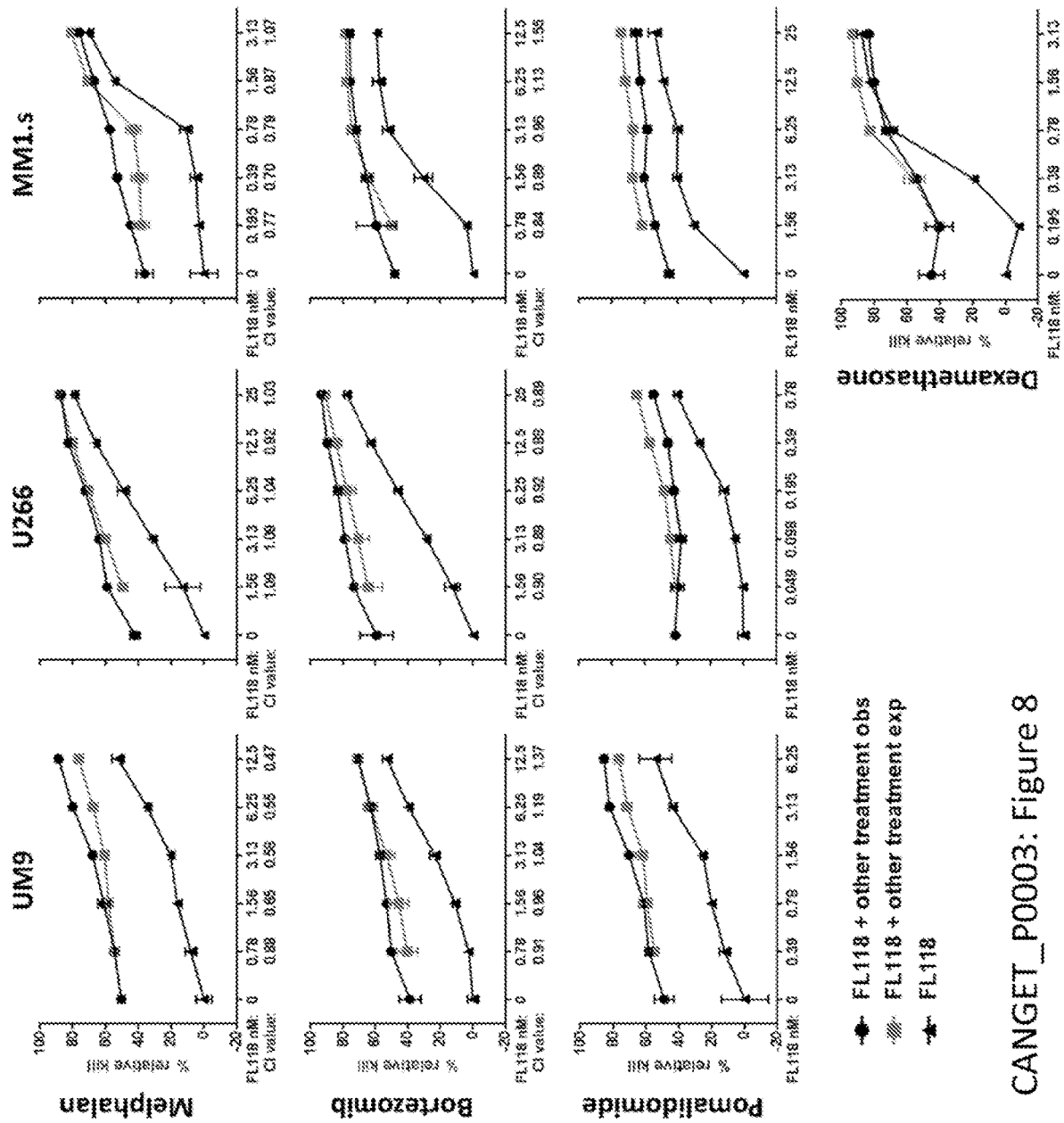

Example 4—FL118 enhances melphalan and bortezomib-induced MM cell lysis: Since efficacious treatment of MM only has been achieved through combination therapy, we investigated whether FL118 could enhance MM cell lysis when combined with currently used anti-MM drugs, including melphalan and bortezomib. Assays with MM cell lines suggested at least additive activity of FL118 combination with melphalan or bortezomib (FIG. 8). In primary BMMNC samples, FL118 showed additive effects with bortezomib and synergistic effects with melphalan (FIG. 3D). Noteworthy there is the recently reported inhibitory activity of FL118 on ERCC6 (Ling, et al. J Exp Clin Cancer Res. 2018; 37:240), a critical regulator of DNA repair. This could explain the favorable combination of FL118 with melphalan and bortezomib, as both drugs can induce DNA damage.

Figure 4:
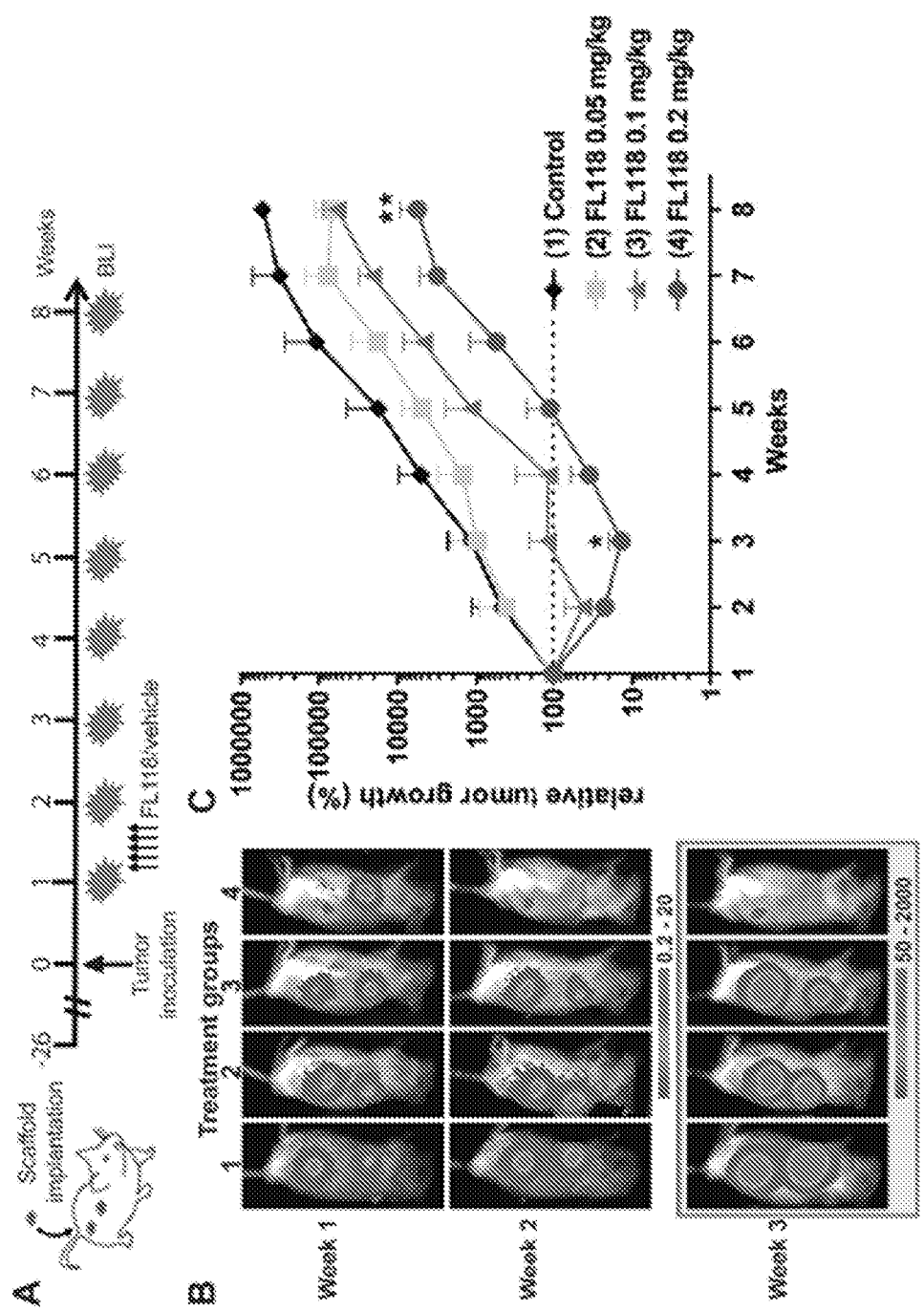

Example 5—In vivo antitumor activity of FL118: We evaluate the potency of FL118 treatment in MM in vivo. We determined the anti-MM activity of FL118 in our humanized xenotransplant mouse model that allows tumor outgrowth in a humanized bone microenvironment. In these assays we used the UM9 cell line to generate MM tumors. When the tumors became visible by BLI, mice were treated with a five-day cycle of FL118 at different doses (FIG. 4). These experiments revealed a dose-dependent in vivo anti-MM activity of FL118. The highest dose of 0.2 mg/kg FL118 was most potent and could reduce the initial tumor volume and delay tumor outgrowth up to 5 weeks (FIG. 4C).

Figure 9:
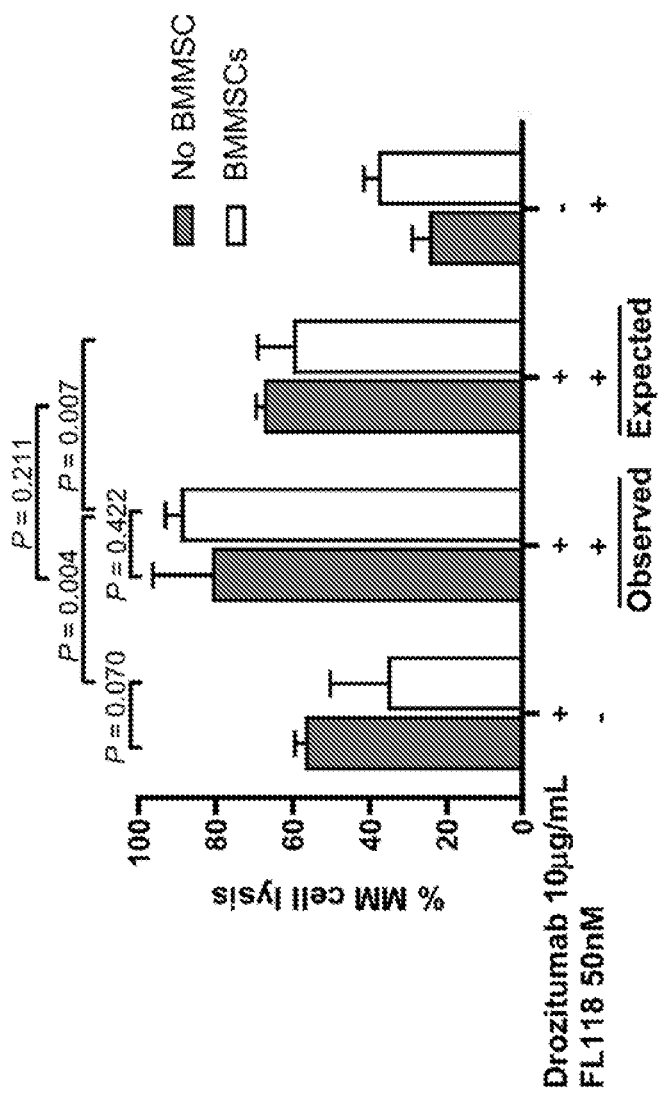

Example 6—FL118 synergistically enhances anti-DR5 antibody therapy and reversed microenvironment-induced immune resistance: It was previously shown that inhibition of anti-apoptotic proteins Survivin and Mcl-1 is au effective approach to tackle environment-mediated immune resistance (de Haart et al. Clin Cancer Res. 2013; 19:5591-601; de Haart et al. Haematol. 2016; 101:e339-42). As FL118 inhibits multiple anti-apoptotic proteins including Survivin and Mcl-1 and showed potent anti-MM activity, we investigate whether combination treatment with this novel small molecule can enhance immunotherapy and overcome immune resistance. Combination therapy of anti-DR5 antibody Drozitumab with FL118 enhanced cell lysis of MM1.s cells with great synergistic activity and reversed the trend of microenvironment-induced immune resistance (FIG. 9). MM cell lysis induced by DR5 antibody upon NK cell binding can be induced via NK cell-mediated cellular cytotoxicity and by cross-linking and clustering the DR5 on the MM cell membrane that triggers death signaling. Together, these results show that FL118 can enhance the efficacy of DR5 antibody treatment and overcome BMMSC-induced protection.

Figure 11:
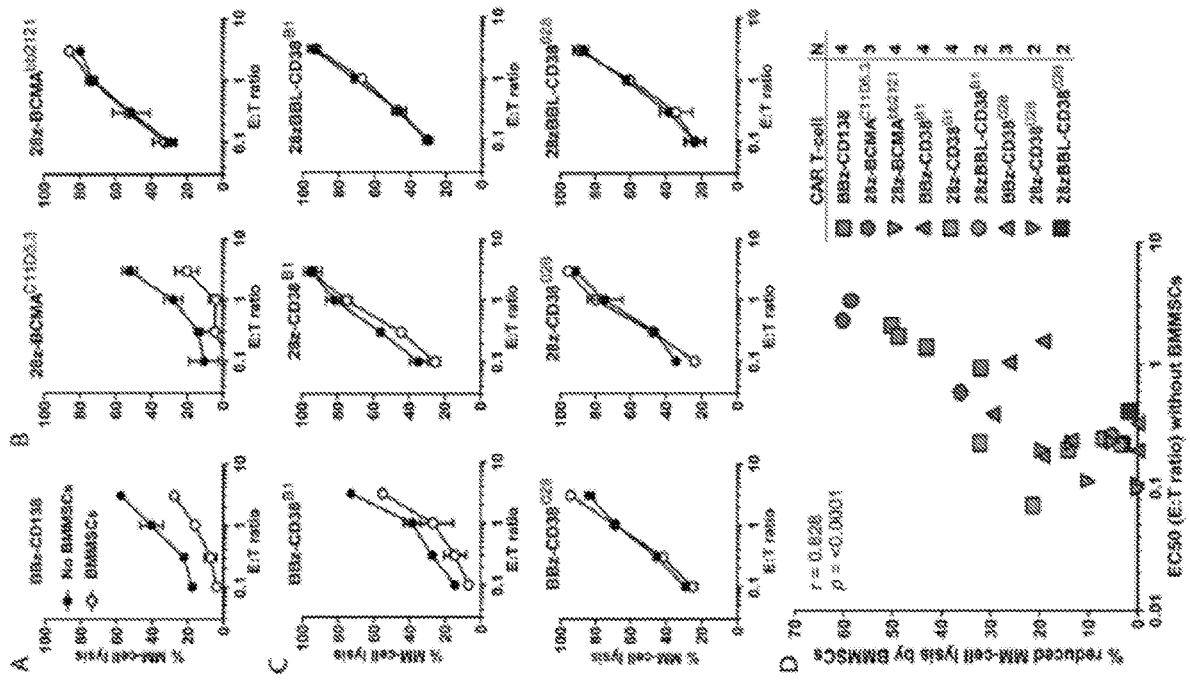

Example 7—BMMSC-mediated immune resistance against CAR T-cells: We have previously shown that BMMSCs facilitate MM cell resistance against lysis by conventional $CD4^+$ and $CD8^+$ CTLs (de Haart S J, et al. Clin Cancer Res. 2013, 19:5591-5601). To investigate the impact of BMMSC-induced immune resistance against CAR T-cells, we used a panel of CD138-, BCMA-, and CD38-directed CAR T-cells, which were generated with the CAR constructs listed in Table 1 and which showed no significant difference in transduction efficiency, CD4/CD8 ratio, or phenotypic profile (FIG. 10). To target BCMA, we included two different CAR T-cells with different avidities to its target antigen. For CD38, we included CAR T-cells with different target affinities and different co-stimulatory domains containing either 4-1BB, CD28, or CD28 plus a separately expressed full length 4-1BB ligand (28zBBL) (Table 1). In BLI based cytotoxicity assays, we tested the efficacy of the CAR T-cells against $CD138^+$, $BCMA^+$, and $CD38^+$ UM9 cells in the absence or presence of BMMSCs (FIG. 11A-C). In the absence of BMMSCs (FIG. 11A C, closed symbols), CD138 CAR T-cells showed a moderate efficacy to induce UM9 cell lysis (FIG. 11A). The efficacy of BCMA CAR T-cells to induce UM9-cell lysis was moderate ($BCMA^{C11D5.3}$ CAR T-cells) or high ($BCMA^{bb2121}$ CAR T-cells), depending on the used ScFv (FIG. 11B). Finally, the lytic activity of CD38 CAR T-cells was, as expected, both dependent on their affinity for its target and their co-stimulatory domains (FIG. 11C). High affinity $CD38^{028}$ CAR T-cells were highly lytic, independent of their co-stimulatory domains, while lower affinity $CD38^{B1}$ CAR T-cells required CD28 co-stimulation to reach high lytic capacities (28z-$CD38^{B1}$ and 28zBBL $CD38^{B1}$ CAR T-cells) in comparison to 4-1BB co-stimulation alone (BBz-$CD38^{B1}$ CAR T-cell).

In the presence of BMMSCs, (FIG. 11A-C, open symbols), the MM cell lysis was inhibited in the case of moderately lytic CD138- and $BCMA^{C11D5.3}$ CAR T-cells by up to 60%. In contrast, there was little or no BMMSC-mediated inhibition of MM-cell lysis by strongly lytic $BCMA^{bb2121}$ CAR T-cells. The inhibitory effect of BMMSCs against CD38 CAR T-cells was moderate (20-30% inhibition) and mainly observed for the lower affinity BBz-$CD38^{B1}$ CAR T-cells. Remarkably, the inhibitory effect of BMMSCs was reduced or completely abrogated when lower affinity $CD38^{B1}$ CAR T-cells contained a CD28 co-stimulatory domain (28z-$CD38^{B1}$ and 28zBBL-$CD38^{B1}$ CAR T-cells). Taken together, these results suggested that the overall killing capacity of CAR T-cells in the absence of BMMSCs, which is a functional reflection of target antigen expression, target affinity, and co-stimulatory signaling, could be an important predictor for the induction of cytotoxic resistance by BMMSCs. Indeed, we observed a strong inverse correlation between the E:T ratios leading to 50% lysis, depicted as EC50 of the CAR T-cells, and the extent of BMMSC-mediated inhibition of lysis (FIG. 11C).

Example 8—BMMSC-mediated protection of patient MM cells against CAR T-cells: To gain more insight into the possible clinical relevancy of the results generated with the model MM cell line UM9, we subsequently tested a selected panel of CAR T-cells on MM-cells that are present in BMMNC samples obtained from MM patients (n=6) in the absence or presence of BMMSCs. We found a comparable association between the level of lysis capacity in the absence of BMMSCs and the inhibitory effect of BMMSCs in this ex vivo setting (FIG. 12A). Analysis of the expression levels of target antigens on patient MM cells revealed that the BMMSCs did not influence the expression levels of CD138 or CD38, while a notable but insignificant decrease in BCMA expression was observed (FIG. 12B). Nonetheless, for all the CAR T-cells tested, the level of antigen down-regulation in the presence of BMMSCs showed no correlation with BMMSC-mediated inhibition of lysis (FIG. 13A-C), thus excluding alteration of antigen expression as a dominant mechanism of BMMSC-induced resistance against CAR T-cells.

Example 9—Mechanisms involved in BMMSC-mediated protection against CAR T-cells: We have previously shown that BMMSCs inhibit T-cell- and antibody-dependent NK cell-mediated lysis of MM cells mainly via cell-cell contact and by upregulation of anti-apoptotic molecules Survivin and Mcl-1, although a certain degree of immune suppression was also observed for $CD8^+$ CTLs (de Haart S J, et al. Clin Cancer Res. 2013, 19:5591-5601). To better understand how BMMSCs inhibit CAR T-cell mediated lysis, we first measured the IFN-γ and granzyme B production by CAR T-cells in response to UM9 cell line or to primary MM cells (n=3) in the presence or absence of BMMSCs, as a reflection of CAR T-cell activation (FIG. 14A-C and FIG. 15A-C). The results revealed that CAR T-cell-mediated lysis of UM9 cells or patient MM cells by $BCMA^{C11D5.3}$ CART-cells and BBz-$CD38^{B1}$ CAR T-cells was inhibited by BMMSCs without a reduction in IFN-γ or granzyme B secretion, suggesting that the BMMSCs did not affect the activation of these CAR T-cells. In contrast, for CD138 CAR T-cells, we observed a substantial reduction in IFN-γ secretion in the presence of BMMSCs against two primary MM samples and with increasing E:T ratios against UM9, BMMSCs did not reduce IFN-γ against a second MM cell line, MM1.s, and did not reduce granzyme B secretion, suggesting a partial or split CAR T-cell suppression (FIGS. 14B and C and FIG. 15). To assess whether soluble factors were involved in lysis-inhibition, we further studied the efficacy of CD138 CAR T-cells to kill UM9 cells in a transwell system, in which BIB MSCs and MM cells were co-cultured either in direct contact or separated by micropore membrane inserts. Remarkably, CD138 CAR T-cell-mediated lysis of UM9 cells was inhibited only when BMMSCs and UM9 were in direct contact (FIG. 14D). Furthermore, Survivin and Mcl-1 were upregulated in UM9 cells only upon direct contact with BMMSCs (FIG. 16). Together, these results suggested that even in case of immunosuppression, immune resistance, through the upregulation of the tumor intrinsic anti-apoptotic machinery, could be the major contributor for BMMSC-mediated inhibition of MM cell lysis by CAR T-cells. To explore this intriguing possibility, we next investigated whether we could overcome the BMMSC-mediated protection against CAR T-cell therapy by inhibition of multiple anti-apoptotic molecules in MM-cells.

Example 10—FL118, a small molecule inhibitor of Survivin, Mcl-1 and XIAP, can effectively modulate BMMSC-induced resistance: FL118 is a small molecule inhibitor of Survivin, Mcl-1 and XIAP. We have early shown that the FL118 small molecule has a profound single agent activity on MM cells and that it can abrogate BMMSC-mediated drug resistance (Examples 1-6). Hence, we now explored whether it could modulate BMMSC-mediated inhibition of CAR T-cell lysis at concentrations that are nontoxic for immune effector cells and BMMSCs. Previously, we had determined that FL118 had no toxic effects on BMMSCs up to a dose of 100 nM. Up to this dose, FL118 also showed no toxic effects on resting T-cells or NK-cells in BMMNC samples obtained from MM or PCL patients, or on PMA-activated $CD25^+$ T-cells of healthy individuals (FIG. 17). Thus, we tested FL118 at doses equal or lower than 100 nM for its capacity to modulate BMMSC-mediated protection of the UM9 cell line against CAR T-cells. As expected, BMMSCs inhibited the CAR T-cell mediated lysis of UM9 cells, which was most evident for the CD138 and $BCMA^{C11D5.3}$ CAR T-cells (FIG. 18A-C, left panels). FL118 treatment showed a dose-dependent lysis of MM-cells, regardless of the presence of BMMSCs (FIG. 18A-C, right panels). When combined with CAR T-cells, FL118 effectively modulated the BMMSC-mediated protection, even at doses as low as 3 nM (FIG. 18A-C, center panels). The combinatorial activity of FL118 and CAR T-cells was synergistic, especially in the presence of BMMSCs, as illustrated by combination index (CI) values below 1 (FIG. 18A-C, center panels). To extend the analyses in an ex vivo setting, we tested FL118 at a low dose of 10 nM for its capacity to modulate BMMSC-mediated protection of patient-derived MM cells against the same panel of CAR T-cells (FIG. 19). As expected, BMMSCs readily inhibited the lysis of primary MM cells by the tested CAR T-cells at an E:T ratio of 1:1, except in a single case where patient MM cell lysis by CD38 CAR T-cells was not inhibited. Importantly, although FL118 showed no/minimal anti-MM activity at the tested dose, it significantly enhanced the patient MM cell lysis by CAR T-cells in the presence of BMMSCs (FIG. 19, observed panel). The significant difference between observed lysis values with the calculated expected lysis values, that presume additive combinatorial effects, indicate that combination of FL118 with CART-cells enhanced MM cell lysis in a synergistic fashion (FIG. 19). Altogether, these results indicate that upregulation of anti-apoptotic molecules in MM cells contribute to BMMSC-mediated protection of MM cells against CAR T-cell lysis. Importantly, the modulation of these anti-apoptotic pathways by FL118 can be highly beneficial, even in case of T-cell suppression, such as was observed for CD138 CAR T-cells.

Example 11—FL118 abrogates BMMSC-mediated immune resistance to conventional CTLs and daratumumab: We previously demonstrated the effective modulation of BMMSC-mediated protection of MM cells against conventional CTLs and daratumumab-dependent ADCC with another small molecule, YM155, which inhibits only Survivin and Mcl-1. Therefore, we evaluated whether FL118 could also be beneficial for these immunotherapeutic interventions. Confirming previous results, the BMMSCs inhibited lysis of UM9 cells by the MM-reactive $CD4^+$ CTL 3AB11 (FIG. 20A, left panel). FL118 completely abrogated this protective effect in a synergistic fashion (FIG. 20A, center panel), similar to what was observed for CAR T-cells. These results could not be extended to experiments with primary MM cells, due to lack of HLA/antigen matched patient's samples. Nonetheless, the effect of FL118 on BMMSC-mediated protection against daratumumab-dependent ADCC could readily be tested in ex vivo experiments using patient-derived MM cells Again, the profound BMMSC-mediated protection against daratumumab-induced MM cell lysis (FIG. 20B, left panel) was abrogated by FL118 (FIG. 20B, middle panel, observed), which expectedly showed varying anti-MM effects as a single agent at this concentration. Also in these ADCC assays, as indicated by the significantly higher observed lysis values than the calculated expected lysis values that presume additive effects, the interaction between FL118 and daratumumab in the presence of BMMSCs was synergistic.

Example 12—The scope of solvents that are used to dissolve a type of CDs (e.g. HP-β-CD): In this disclosure, we have identified three groups of organic solvents: (1) methanol or ethanol; (2) formic acid (FA), acetic acid (AcetA), zinc acetate (ZA) or glyoxal (ethauedial) and (3) ethylene glycol (EG), propylene glycol (PG), formamide (FAD), (N,N,N',N')-tetramethyl-ethylenediamine (TEMED), ethanolamid (EA)e or 2-mercaptoethanol (MercE) alone or in different ratio of combination of the defined certain two or three solvents are used to dissolve a type of CDs (e.g. HP-β-CD) for FL118 formulation. However, the following organic solvents alone or in any ratio of combination of two, three or more are not good for dissolving any types of cyclodextrins (CDs) for FL118 formulation. These non-suitable solvents include, but may not be limited to, methyl formate, ethyl formate, isobutyl acetate, methyl acetate, ethyl acetate, butyl acetate, acetic anhydride, acetone, anisole, acetonitrile, benzene, 1-butanol, 2-butanol, tert-butyl methyl ether, carbon tetrachloride, benzyl chloride, benzyl benzoate, chlorobenzene, chloroform, cumene, cyclohexane, 1,2-dibromoethene, 1,1-dichloroethene, 1,2-dichloroethene, dichloromethane, 1, 2-dimethoxyethane 1,4-dioxane, 2-ethoxyethanol, 1,2-dimethoxyethanol, diethyl ether, heptane, hexane, isoamyl alcohol, amyl alcohol, 2-hexanone, cyclohexylmethane, methylethyl ketone, methylisobutyl ketone, 2-methyl-1-propanol, 2-Methyl-2-propanol, pentane, propyl alcohol, isopropyl alcohol, propyl acetate, toluene, xylene, benzaldehyde, benzaldehyde dimethyl acetal, tetralin, (1,1,2)-trichloroethene, tetrahydrofuran, pyridine, sulfolane, glycerine, diethyl pyrocarbonate, and dimethyl sulfate. Examples from each unique working organic solvents are presented below through Example 13 to Example 24 through testing demonstration of antitumor activity and toxicity profile with each of the data presented in from FIG. 21 to FIG. 32 below.

Example 13—Methanol-HPβCD-formulated FL118 antitumor activity and toxicity (body weight changes) profiles: The antitumor activity and toxicity of FL118 formulated through the methanol-HPβCD muster solution were tested in the human APC/p53/Kras-triple-mutated SW620 colorectal cancer xenograft tumor animal models. The data were shown in FIG. 21 (tumor curves in A and body weight change in B). As shown, while vehicle-treated mice with tumors grew to the maximal tumor size allowed and the tumor mice had to be euthanized on day 4, FL118-reated mice exhibited tumor regression with the potential tumor elimination, although FL118 dosing level should be controlled based on the animal body weight changes.

Example 14—Ethanol-HPβCD-formulated FL118 antitumor activity and toxicity (body weight changes) profiles: The antitumor activity and toxicity of FL118 formulated through the ethanol-HPβCD muster solution were tested in the human APC/p53/Kras-triple-mutated SW620 colorectal cancer xenograft tumor animal models. The data were shown in FIG. 22 (tumor curves in A and body weight change in B). As shown, while vehicle-treated mice with tumors grew to the maximal tumor size allowed and the tumor mice had to be euthanized on day 4, FL118-reated mice exhibited tumor regression with tumor elimination. However, FL118 dosing level should be controlled based on the animal body weight changes.

Example 15—Formic acid (FA)-HPβCD formulated FL118 antitumor activity and toxicity (body weight changes) profiles: The antitumor activity and toxicity of FL118 formulated through the FA-HPβCD muster solution were tested in the human SW620 colorectal cancer xenograft tumor animal models. The data were shown in FIG. 23 (tumor curves in A and body weight change in B). As shown, while vehicle-treated mice with tumors grew to the maximal tumor size allowed and the tumor mice had to be euthanized on day 4, FL118-reated mice exhibited tumor regression with potential tumor elimination. Importantly, at the FL118 dosing levels used, there is no body weight loss. Therefore, high dosing levels could be used when required.

Example 16—Acetic acid (AcetA)-HPβCD-formulated FL118 antitumor activity and toxicity (body weight changes) profiles: The antitumor activity and toxicity of FL118 formulated through the AcetA-HPβCD muster solution were tested in the human SW620 colorectal cancer xenograft tumor animal models. The data were shown in FIG. 24 (tumor curves in A and body weight change in B). As shown, while vehicle-treated mice with tumors grew to the maximal tumor size allowed and the tumor mice had to be euthanized on day 4, FL118-rested mice exhibited tumor regression with tumor elimination, Importantly, at the FL118 dosing levels used, there is no body weight loss. Therefore, high dosing levels could be used when required.

Example 17—Zinc acetate (ZA)-HPβCD-formulated FL118 antitumor activity and toxicity (body weight changes) profiles: The antitumor activity and toxicity of FL118 formulated through the ZA-HPβCD muster solution were tested in the human SW620 colorectal cancer xenograft tumor animal models. The data were shown in FIG. 25 (tumor curves in A and body weight change in B). As shown, while vehicle-treated mice with tumors grew to the maximal tumor size allowed and the tumor mice had to be euthanized on day 4, FL118-rested mice exhibited tumor regression with tumor elimination. However, FL118 dosing levels should be controlled based on the animal body weight changes.

Example 18—Glyoxal-HPβCD-formulated FL118 antitumor activity and toxicity (body weight changes) profiles: The antitumor activity and toxicity of FL118 formulated through the glyoxal-HPβCD muster solution were tested in the human. SW620 colorectal cancer xenograft tumor animal models. The data were shown in FIG. 26 (tumor curves in A and body weight change in B). As shown, while vehicle-treated mice with tumors grew to the maximal tumor size allowed and the tumor mice had to be euthanized on day 4, FL118-rested mice exhibited tumor regression with tumor elimination. However, FL118 dosing levels should be controlled based on the animal body weight changes.

Example 19—Ethylene glycol (EG)-HPβD-formulated FL118 antitumor activity and toxicity (body weight changes) profiles: The antitumor activity and toxicity of FL118 formulated through the EG-HPβCD muster solution were tested in the human SW620 colorectal cancer xenograft tumor animal models. The data were shown in FIG. 27 (tumor curves in A and body weight change in B). As shown, while vehicle-treated mice with tumors grew to the maximal tumor size allowed and the tumor mice had to be euthanized on day 4, FL118-reated mice exhibited tumor regression with potential tumor elimination, although FL118 dosing levels should be controlled based on the animal body weight changes.

Example 20—Propylene glycol (PG)-HPβCD formulated FL118 antitumor activity and toxicity (body weight changes) profiles: The antitumor activity and toxicity of FL118 formulated through the PG-HPβCD muster solution were tested in the human SW620 colorectal cancer xenograft tumor animal models. The data were shown in FIG. 28 (tumor curves in A and body weight change in B). As shown, while vehicle-treated mice with tumors grew to the maximal tumor size allowed and the tumor mice had to be euthanized on day 4, FL118-reated mice exhibited tumor regression with potential tumor elimination, although FL118 dosing levels should be controlled based on the animal body weight changes.

Example 21—Formamide (FAD)-HPβCD formulated FL118 antitumor activity and toxicity (body weight changes) profiles: The antitumor activity and toxicity of FL118 formulated through the FAD-HPβCD muster solution were tested in the human SW620 colorectal cancer xenograft tumor animal models. The data were shown in FIG. 29 (tumor curves in A and body weight change in B). As shown, while vehicle-treated mice with tumors grew to the maximal tumor size allowed and the tumor mice had to be euthanized on day 4, FL118-reated mice exhibited tumor regression with potential tumor elimination. However, FL118 dosing levels should be controlled based on the animal body weight changes.

Example 22—N,N,N',N'-tetramethyl ethylene diamine (TEMED)-HPβCD-formulated FL118 antitumor activity and toxicity (body weight changes) profiles: The antitumor activity and toxicity of FL118 formulated through the TEMED-HPβCD muster solution were tested in the human SW620 colorectal cancer xenograft tumor animal models. The data were shown in FIG. 30 (tumor curves in A and body weight change in B). As shown, while vehicle-treated mice with tumors grew to the maximal tumor size allowed and the tumor mice had to be euthanized on day 4, FL118-reated mice exhibited tumor regression with potential tumor elimination at the high dosing level. However, FL118 at the low dosing level only exhibited limited antitumor activity. Interestingly high dosing FL118 did not exhibit toxicity.

Example 23—Ethanolamide. (EA)-HPβCD formulated FL118 antitumor activity and toxicity (body weight changes) profiles: The antitumor activity and toxicity of FL118 formulated through the EA-HPβCD muster solution were tested in the human SW620 colorectal cancer xenograft tumor animal models. The data were shown in FIG. 31 (tumor curves in A and body weight change in B). As shown, while vehicle-treated mice with tumors grew to the maximal tumor size allowed and the tumor mice had to be euthanized on day 4, FL118-reated mice exhibited tumor regression with tumor elimination, although FL118 dosing levels should be controlled based on the animal body weight changes.

Example 24—Mercaptoethanol (MercE)-HPβCD-formulated FL118 antitumor activity and toxicity (body weight changes) profiles: The antitumor activity and toxicity of FL118 formulated through the MercE-HPβCD muster solution were tested in the human SW620 colorectal cancer xenograft tumor animal models. The data were shown in FIG. 32 (tumor curves in A and body weight change in B).

As shown, while vehicle-treated mice with tumors grew to the maximal tumor size allowed and the tumor mice had to be euthanized on day 4, FL118-reated mice exhibited tumor regression with tumor elimination. However, FL118 dosing levels should be controlled based on the animal body weight changes.

Example 25—Physical characterization of FL118 Active Pharmaceutical Ingredient (API): Physical characterization of L118 API crystal versus amorphous statuses was performed using X-ray powder diffractometer (XRPD) and Differential Scanning Calorimetry (DSC) technologies. As shown in FIG. 33, FL118 API (from the non-GMP FL118 batch of P12211-005-P1) displayed crystalline diffraction peak, which indicated that FL118 is a crystal. However, The DSC curves shown in FIG. 34 did not show any melting peaks, indicating that FL118 had no melting point.

Example 26—Hydroxypropyl-β-cyclodextrin (HP-β-CD)-FL118 API complex powder at the 300 mg API level using the Spray Drying processes: The hydroxypropyl-β-cyclodextrin (HP-β-CD) complex preparation process was described as below: weighed about 10 g HP-β-CD into 50 mL volumetric flask containing a magnetic stir bar, added about 40 mL 100% ethanol. Placed the volumetric flask on a Hotplate Stirrer (MS-H-Pro+, Dragonlab) and was magnetic stirring at room temperature under 1000 rpm for 30 min. Then added more ethanol to final volume of 50 mL to make a 20% ethanol-HPβCD solution. This 20% ethanol-HPβCD solution was magnetically stirring overnight to make sure the HPβCD to be dissolved in the ethanol evenly to become a complete solution. Then, transferred 15 mL of the prepared 20% HPβCD in ethanol into three 40 mL glass bottle containing 300 mg FL118 API (from the non-GMP FL118 batch of P12211-005-P1 to produce HPβCD-FL118 complex batch of FR00535-01-190708) and was magnetically stirring under 1000 rpm in the following 3 conditions at room temperature to prepare master suspensions: Condition 1: Stirring for 1 hour. Condition 2: Stirring for 6 hours. Condition 3: Stirring for 24 hours to obtain ethanol-HPβCD-FL118 complex suspension contains 300 mg FL118 at concentration of 20 mg/mL in each of the three 40 mL glass bottle. Spray-dryer (Model: Buchi B290) was employed to prepare HPβCD-FL118 complex and the stock suspensions were stirring during spray drying. Detailed process parameters for spray drying were listed in Table 2. The obtained HPβCD-FL118 complex powders were dried under vacuum at 30° C. overnight, and the yield of the three products were 83.03%, 79.70% and 81.81% respectively.

Example 27—Characterization of the HP-β-CD-FL118 API complex powder at the 300 mg level for 3 conditions (FL118 from the non-GMP FL118 batch of P12211-005-P1 to produce HPβCD-FL118 complex batch of FR00535-01-190708): The HP-β-CD-FL118 complex powder was characterized using X-ray powder diffractometer (XRPD), Modulated Differential Scanning Calorimetry (mDSC) and High Performance Liquid Chromatography (HPLC). The results are summarized in Table 3. Based on XRPD results shown in FIG. 35, the HPβCD-FL118 complex powder products were all amorphous. Only one glass transition temperature was observed in mDSC results for the HPβCD-FL118 complex products (FIG. 36: Condition 1, FIG. 37: Condition 2 and FIG. 38: Condition 3), indicating the good miscibility of FL118 API with HPβCD. The glass transition temperature of the three HPβCD-FL118 complex products is 96.93° C., 81.06° C. and 66.78° C. respectively (Table 3). The mDSC profile of the HPβCD excipient itself is shown in FIG. 39 for comparison.

Example 28—hydroxypropyl-β-cyclodextrin (HP-β-CD)-FL118 API complex powder at the 2 g API scale-up level using the Spray Drying processes: The HPβCD-FL118 complex preparation process is: Twenty grams of HPβCD were weighted and put into 200 mL glass bottle containing a magnetic stir bar and then added with 70 mL 100% ethanol. Then the glass bottle was placed on a Hotplate Stirrer and was magnetic stirring at 30° C. under 1000 rpm overnight to make sure the HPβCD to be dissolved in the ethanol evenly to become a complete solution. Then two grams scale-up FL118 API powder was from the GMP FL118 batch of 18001, which was used to produce the HPβCD-FL118 complex for the batch of FR00535-02-190904-01. The two grams of GMP FL118 were weighted and put into the ethanol-HPβCD solution. The ethanol-HPβCD-FL118 mixture was magnetically stirring under 1000 rpm at room temperature for 24 hours. An ethanol-HPβCD-FL118 complex suspension at concentration of FL118 at 20 mg/mL was obtained. Then the spray-dryer (Model: Buchi B290) was employed to prepare HPβCD-FL118 complex powder from the stock suspension, which was stirring during spray drying. Detailed process parameters for spray drying were listed in Table 4. The spray-drying process-obtained HPβCD-FL118 complex powder was dried under vacuum at 30° C. overnight, and the yield of the products was 90.0% (Table 4).

Example 29—Characterization of the HP-β-CD-FL118 API complex powder for the two-gram scale-up level: The HP-β-CD-FL118 complex powder was characterized using X-ray powder diffractometer (XRPD), Modulated Differential Scanning Calorimetry (mDSC) and High Performance Liquid Chromatography (HPLC). The results are summarized in Table 5. Based on XRPD results, similar to the 300 mg FL118 scale situation for the HP β-CD-FL118 formulation, the HPβCD-FL118 complex products (Batch No.: FR00535-02-190904-01) were amorphous (FIG. 40). No glass transition temperature of HPβCD-FL118 complex products (Batch No.:FR00535-02-190904-01) was observed in mDSC results (FIG. 41).

Example 30—HP-β-CD-FL118 API complex stability test and characterization: The HP-β-CD-FL118 complex samples (FR00535-02-190904-01) were set up for 10 days stability study as shown in Table 6. About 20 mg of the HP-β-CD-FL118 complex (FR00535-02-190904-01) were weighed into 40 mL vials. Then the samples were covered by aluminum foil with pinholes and stored in stability chamber at 25° C./60% RH (open) and 40° C./75% RH (open) for 10 days. The HP-β-CD-FL118 complex stability test results are summarized in Table 7 and Table 8. The analytical results from X-ray powder diffractometer (XRPD) and High Performance Liquid Chromatography (HPLC) are presented in FIG. 42 and FIG. 43, respectively.

Example 31—HP-β-CD-FL118 API complex dissolution test: The HP-β-CD-FL118 complex samples (FR00535-02-190904-01) 220 mg were weighed into 40 mL glass bottle containing a magnetic stir bar, added 20 mL 37.0° C. pH1.2 buffer (or pH6.8 buffer) into the vial and the vials were stirred at 100 rpm at 37±0.5° C. for 2 h. The sampling time points as. The sample solution of 300 μL was collected at each time point of 5, 10, 15, 30, 45, 60.90, 120 min. The collected samples were analyzed for the concentrations of the supernatants by HPLC. The results are summarized in Table 9.

Example 32—Alternative process development of HP-β-CD-FL118 complex preparation by spray drying: A total of 10 grams of 2-hydroxypropyl-beta-cyclodextrin (HPβCD) were weighted and put into a 50 mL glass flask with a magnetic stir bar inside, followed by adding 40 mL 100% ethanol. The flask was then put on a Hotplate Stirrer and was stirring at room temperature under 1000 rpm for 30 min, followed by adding 100% ethanol to a final volume of 50 mL to make a 20% HPβCD-ethanol solution. This 20% HPβCD-ethanol solution was magnetically stirring overnight to make sure the HP-β-CD to be dissolved in the ethanol evenly to become a complete solution. Next day, transferred 15 mL the prepared 20% HPβCD-ethanol solution into each of three 40 mL glass bottle containing 300 mg FL118 powder (from the GMP FL118 batch of 18001 to produce HPβCD-FL118 complex batch of FR00535-04-191022-01) and was mixed by Dispersion homogenizer (Model: T10 BASIC, IKA) at 5grade (every 10 min homogenizer followed by 5 min break) for different conditions: Condition 1: Homogenization for 40 min (total mix time 30 min). Condition 2: Homogenization for 85 min (total mix time 60 min). Condition 3: Homogenization for 175 min (total mix time 120 min). This generated three of ethanol-HPβCD-FL118 suspension with a concentration of FL118 at 20 mg/mL. Spray-dryer (Model: Buchi B290) was subsequently employed to prepare HPβCD-FL118 complex powder. The ethanol-HPβCD-FL118 suspension stocks were stirring during spray drying. Detailed process parameters for spray drying were summarized in Table 10. The obtained HPβCD-FL118 complex powders were dried under vacuum at 30° C. overnight, and the yield of the three products were 76.7%, 81.3% and 82.1% respectively (Table 10).

Example 33—Scale-up preparation of HP-β-CD-FL118 complex at the 10-gram level of FL118 API by spray drying: A total of 100 grams of 2-hydroxypropyl-beta-cyclodextrin (HPβCD) were weighted and put into a 1000 mL glass bottle with a magnetic stir bar inside, followed by adding 500 mL 100% ethanol. The bottle were then placed on a Hotplate Stirrer and was stirring at 50° C. under 1000 rpm for 1 h to make sure the HPβCD to be completely dissolved in the ethanol evenly to become a complete solution. Then, 10 grams of FL118 powder (from the GMP FL118 batch of 18001 to produce HPβCD-FL118 complex batch of FR00535-05-191104-01) were weighted and put into the HPβCD-ethanol solution in the 1000 mL bottle, followed by homogenization using the Dispersion homogenizer (Model: T18, IKA) at 15000 rpm (every 5 min homogenizer followed by 5 min break) for 55 min (total mix time 30 min). The generated ethanol-HPβCD-FL118 suspension with a concentration of FL118 at 20 mg/mL. Ethanol-HPβCD-FL118 suspension contains 10 g FL118 at concentration of 20 mg/mL in a total of 500 mL volumes. Spray-dryer (Model: Buchi B290) was employed to prepare HPβCD-FL118 complex. The HPβCD-FL118 complex stock suspensions were stirring during spray drying. Detailed process parameters for spray drying were presented in Table 11. The obtained HPβCD-FL118 complex powders were dried under vacuum at 30° C. overnight, and the yield of the products was 90.8% (Table 11).

Example 34—Characterization of the HP-β-CD-FL118 complex at the 10-gram level of FL118 by X-ray powder diffractometer (XRPD): The scale-up-obtained HP-β-CD-FL118 complex powders produced in the Example 16 were characterized by XRPD and HPLC. Results were summarized in Table 12. Based on XRPD results, the HP-β-CD-FL118 complex products were amorphous. The result from the XRPD analysis is shown in FIG. 44.

Pharmaceutical Formulation Process

The formulation of FL118 disclosed in this disclosure is the further to the development of related disclosures. See, PCT/US15/22095 (Use of the FL118 core chemical structure platform to generate FL118 derivatives for treatment of human disease) and PCT/US19/51595 (Matter of composition, synthesis, formulation and application of FL118 platform positions 7 and 9-derived analogues for treatment of human disease). All of which are hereby incorporated by reference in their entirety.

The formulation of FL118 disclosed in this disclosure is in the process of first making a FL118-HP-β-CD formulation complex in the following steps with appropriate organic solvents:

Step 1: Dissolving a type of cyclodextrin (CD) such as HP-β-CD into an appropriate organic solvents including, but may not be limited to, methanol, ethanol, formic acid (FA), acetic acid (AcetA), zinc acetate (ZA), glyoxal, ethylene glycol (EG), propylene glycol (PG), formamide (FAD), (N,N,N',N')-tetramethyl-ethylenediamine (TEMED), ethanolamide (EA) or 2-mercaptoethanol (MercE), respectively, to make a master solution of methanol-HP-β-CD, ethanol-HP-β-CD, FA-HP-β-CD, AcetA-HP-β-CD, ZA-HP-β-CD, glyoxal-HP-β-CD, EG-HP-β-CD, PG-HP-β-CD, FAD-HP-β-CD, TEMED-HP-β-CD, EA-HP-β-CD or -HP-β-CD in an appropriate concentration of HP-β-CD at 10-40% (w/v: 10-40 g/100 mL) for formulating FL118 into a concentration of 10 mg/mL to 40 mg/mL, in turn. In this disclosure, we made the fixed ratio of FL118:HP-β-CD as 1:10 (w/w), which is roughly equivalent to one FL118 molecule to 1.5 molecules of RP-β-CD. Dissolution of HP-β-CD into methanol, ethanol, FA, AcetA, ZA, glyoxal, EG, PG, FAD, TEMED, EA or MercE should be achieved by vortex and/or shaking on an equipment until all HP-β-CD is completely dissolved into methanol, ethanol, FA, AcetA, ZA, glyoxal, EG, PG, FAD, TEMED, EA or MercE, respectively, to become a clear solution of methanol-HP-β-CD, ethanol-HP-β-CD, FA-HP-β-CD, AcetA-HP-β-CD, ZA-HP-β-CD, glyoxal-HP-β-CD, EG-HP-β-CD, PG-HP-β-CD, FAD-HP-β-CD, TEMED-HP-β-CD, EA-HP-β-CD or 2MercE-HP-β-CD, respectively.

Step 2: Dispersing the FL118 API completely into the solution of methanol-HP-β-CD, ethanol-HP-β-CD, FA-HP-β-CD, AcetA-HP-β-CD, ZA-HP-β-CD, glyoxal-HP-β-CD, EG-HP-β-CD, PG-HP-β-CD, FAD-HP-β-CD, TEMED-HP-β-CD, EA-HP-β-CD or 2MercE-HP-β-CD, respectively, by a process of homogenization using a dispersion homogenizer (or other disperse methods such as vortex) to form methanol-HP-β-CD-FL118 complex suspension, ethanol-HP-β-CD-FL118 complex suspension, FA-HP-β-CD-FL118 complex suspension, ZA-HP-β-CD-FL118 complex suspension, glyoxal-HP-β-CD-FL118 complex suspension, PG-HP-β-CD-FL118 complex suspension, FAD-HP-β-CD-FL118 complex suspension, TEMED-HP-β-CD-FL118 complex suspension, EA-HP-β-CD-FL118 complex suspension or 2MercE-HP-β-CD-FL118 complex suspension, respectively.

Step 3: (1) The resultant suspension (solution in the FA case) of methanol-HP-β-CD-FL118 complex, ethanol-HP-β-CD-FL118 complex, FA-HP-β-CD-FL118 complex, AcetA-HP-β-CD-FL118 complex, ZA-HP-β-CD-FL118 complex or glyoxal-HP-β-CD-FL118 complex prefers to go into a spray-dry process to remove methanol, ethanol, FA, AcetA, ZA or glyoxal, respectively, in a closed loop spray drying system with solvent recovery and an inert gas (e.g. nitrogen) to make an inert atmosphere during spray drying process. (2) The resultant suspension of EG-HP-β-CD-FL118 complex, PG-HP-β-CD-FL118 complex, FAD-HP-β-CD-FL118 complex, TEMED-HP β-CD-FL118 complex, EA-HP-β-CD-FL118 complex or MercE-HP-β-CD-FL118 complex should go through a lyophilization process or other approaches to remove the organic solvent of EG, PG, FAD, TEMED, EA or 2MercE, respectively, as many as possible.

Step 4: The HP-β-CD-FL118 complex powder resulted from Step 3(1) may go through a jet milling process, which will depend on the particle size requirement then. Other HP-β-CD-FL118 complex resulted from step3(2) may be unable to go through a jet milling process due to incomplete removing of the organic solvent but can directly go into Step 5 below.

Step 5: The jet-milled or non-jet-milled HP-β-CD-FL118 complex can be then resuspended with clinical saline in the presence of 0-5% propylene glycol (PG) and 0-5% polyethylene glycol 400 (PEG400 in a concentration of FL118 ranging from 0.1 mg/mL to 5 mg/mL for oral administration. The final PG or PEG400 in the FL118 administration suspension in most cases is about 2.5% PG and 2.5% PEG400.

A particular example using methanol (or ethanol) is provided below:

1) Weight 20 g HP-β-CD to be dissolved in 87.3 mL anhydrous methanol to make a 20% methanol-HP-β-CD solution through vortex/shaking until all HP-β-CD is dissolved into methanol (add additional methanol to make a total of 100 mL of final volume if needed).
2) Dissolve 2 g of FL118 into the 100 mL 20% methanol-HP-β-CD solution to make the methanol-HP-β-CD-FL118 complex suspension (i.e. FL118 20 mg/mL) through homogenization using a dispersion homogenizer for 60 min with 5 min on and 5 min off exchanges (real homogenization time is ~30 min) to avoid possibly high temperature-induced FL118 degradation.
3) Using a spray-drying process with the equipment that has a closed loop spray-dry system with solvent recovery and an inert gas (e.g. nitrogen) to make an inert atmosphere during the spray-dry process to remove methanol. Of note, since the methanol-HP-β-CD-FL118 complex is a suspension, the container of the methanol-HP-β-CD-FL118 complex suspension having a magnetic bar inside should be put on a magnetic plate for well suspension during the spray-drying process.

In the next aspect, FL118-HP-β-CD complex powder can be further made into capsule or tablet formats as follows for oral administration.

For making FL118 capsules, FL118-HP-β-CD complex powder can be directly made into capsules without adding additional gradients.

For making FL118 tablets, the FL118-HP-β-CD complex powder (5-25%) is mixture with microcrystalline cellulose (MCC, 30%-80%), corn starch (0%-40%), lactose (10%-25%), colloidal silicone dioxide (0%-3%), dibasic calcium phosphate (1%-10%), and magnesium stearate (0.2%-3%). The excipient mixture will be further milled to let every ingredient be evenly distributed in the powder. This smooth powder is then pressed into tablet by a dry compression process to made the smooth powder into tablets.

The current disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. For example, the solvents of methanol, ethanol, formic acid, or acetic acid can be alone or in an appropriate percentage mixture for dissolving a type of CD (e.g. HP-β-CD) as a strategy for the formulation process. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting. In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

While various aspects and illustrative embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application is specifically and individually incorporated by reference in its entirety for all purposes.

The foregoing summary is illustrative only and is not intended to be in any way limiting. In addition to the illustrative aspects, embodiments, and features described above, further aspects, embodiments, and features will become apparent by reference to the drawings and examples presented in the detailed description in the current disclosure.

What is claimed is:

1. A formulation comprising:
    an FL118 compound,
    at least one cyclodextrin (CD), and,
    an organic solvent or excipient,
    wherein the organic solvent is methanol, ethanol, formic acid, a salt formate, acetic acid, a salt acetate, glyoxal, ethylene glycol, propylene glycol (PG), formamide, (N,N,N',N')-tetramethyl-ethylenediamine, ethanolamide, or 2-mercaptoethanol,
    wherein the FL118 compound forms a complex with the at least one CD resulting in an CD-FL118 complex,
    wherein the CD-FL118 complex has a fixed ratio of FL118:CD (w/w), and
    wherein the CD-FL118 complex is within the range of 5-25% of the formulation.

2. The formulation of claim 1, wherein the salt formate is sodium formate, or the salt acetate is zinc acetate, potassium acetate, or sodium acetate.

3. The formulation of claim 1, wherein the at least one cyclodextrin (CD) is β-cyclodextrin (β-CD), hydroxypropyl-β-cyclodextrin (HP-β-CD), sulfobutylether-β-cyclodextrin (SBE-β-CD), methyl-β-cyclodextrin (me-β-CD), 2-hydroxypropyl-β-cyclodextrin, 4-sulfobutylether-β-cyclodextrin, or methyl-β-cyclodextrin or a combination thereof.

4. The formulation of claim 3, wherein the cyclodextrin is HP-β-CD;
and the HP-β-CD is dissolved into methanol, ethanol, formic acid, a salt formate, acetic acid, a salt acetate, glyoxal, ethylene glycol, propylene glycol, formamide, (N,N,N',N')-tetramethyl-ethylenediamine, ethanolamide or 2-mercaptoethanol to make a solution of methanol-HP-β-CD, ethanol-HP-β-CD, formic acid-HP-β-CD, sodium formate-HP-β-CD, acetic acid-HP-β-CD, zinc acetate-HP-β-CD, glyoxal-HP-βCD, ethylene glycol-HP-β-CD, propylene glycol-HP-β-CD, formamide-HP-β-CD, (N,N,N',N')-tetramethyl-ethylenediamine-HP-β-CD, ethanolamide-HP-β-CD or 2-mercaptoethanol-HP-β-CD; and
wherein the FL118 of the FL118-HP-β-CD complex has a concentration of 10 mg/mL to 40 mg/mL in the formulation.

5. The formulation of claim 4, wherein the ratio of FL118:HP-β-CD is 1:10 (w/w).

6. The formulation of claim 4, wherein FL118 is dispersed into the solution of methanol-HP-β-CD, ethanol-HP-β-CD, formic acid-HP-β-CD, sodium formate-HP-β-CD, acetic acid-HP-β-CD, zinc acetate-HP-β-CD, glyoxal-HP-β-CD, ethylene glycol-HP-β-CD, propylene glycol-HP-β-CD, formamide-HP-β-CD, (N,N,N',N')-tetramethyl-ethylenediamine-HP-β-CD, ethanolamide-HP-β-CD or 2-mercaptoethanol-HP-β-CD to form a suspension of methanol-HP-β-CD-FL118 complex, ethanol-HP-β-CD-FL118 complex, formic acid-HP-β-CD-FL118 complex, sodium formate-HP-β-CD-FL118 complex, acetic acid-HP-β-CD-FL118 complex, zinc acetate-HP-β-CD-FL118 complex, glyoxal-HP-β-CD-FL118 complex, ethylene glycol-HP-β-CD-FL118 complex, propylene glycol-HP-β-CD-FL118 complex, formamide-HP-β-CD, (N,N,N',N')-tetramethyl-ethylenediamine-HP-β-CD-FL118 complex, ethanolamide-HP-β-CD-FL118 complex or 2-mercaptoethanol-HP-β-CD-FL118 complex.

7. The formulation of claim 6, wherein the suspension of methanol-HP-β-CD-FL118 complex, ethanol-HP-β-CD-FL118 complex, formic acid-HP-β-CD-FL118 complex, or acetic acid-HP-β-CD-FL118 complex undergoes a spray-dry process to remove methanol, ethanol, formic acid, or acetic acid to form a HP-β-CD-FL118 complex powder.

8. The formulation of claim 6, wherein the suspension of ethylene glycol-HP-β-CD-FL118 complex, propylene glycol-HP-β-CD-FL118 complex, formamide-HP-β-CD, (N,N,N',N')-tetramethyl-ethylenediamine-HP-β-CD-FL118 complex, ethanolamide-HP-β-CD-FL118 complex or 2-mercaptoethanol-HP-β-CD-FL118 complex goes through a lyophilization process to remove the ethylene glycol, propylene glycol, formamide, (N,N,N',N')-tetramethyl-ethylenediamine, ethanolamide, or 2-mercaptoethanol.

9. The formulation of claim 8, wherein the lyophilized HP-β-CD-FL118 complex is resuspended with saline comprising 0-5% PG and 0-5% PEG400 to achieve an FL118 concentration of 0.1 mg/mL to 5 mg/ml for oral administration.

10. The formulation of claim 9, wherein the saline comprises 2.5% PG and 2.5% PEG400.

11. The formulation of claim 6, wherein the HP-β-CD-FL118 complex is made into a capsule or a tablet for oral administration.

12. The formulation of claim 7, wherein the HP-β-CD-FL118 complex powder within the range of 5-25% is mixed with microcrystalline cellulose within the range of 30%-80%, corn starch within the range of 0%-40%, lactose within the range of 10%-25%, colloidal silicone dioxide within the range of 0%-3%, dibasic calcium phosphate within the range of 1%-10%, and magnesium stearate within the range of 0.2%-3% and pressed into a tablet or made into a capsule.

13. The formulation of claim 1, wherein the formulation further comprises a pharmaceutically acceptable salt, wherein the pharmaceutically acceptable salt is a chloride, phosphate, mesylate, bismesylate, tosylate, lactate, tartrate, malate, bis-acetate, or citrate salt.

14. The formulation of claim 2, wherein the formulation comprises more than one organic solvent.

15. The formulation of claim 1, wherein the FL118 has a crystal status.

* * * * *